US007770584B2

(12) United States Patent
Danek et al.

(10) Patent No.: US 7,770,584 B2
(45) Date of Patent: Aug. 10, 2010

(54) MODIFICATION OF AIRWAYS BY APPLICATION OF MICROWAVE ENERGY

(75) Inventors: Christopher J. Danek, Santa Clara, CA (US); Bryan E. Loomas, Los Gatos, CA (US); Thomas M. Keast, Mountain View, CA (US); Michael D. Laufer, Menlo Park, CA (US)

(73) Assignee: Asthmatx, Inc., Sunnyvale, CA (US)

( * ) Notice: Subject to any disclaimer, the term of this patent is extended or adjusted under 35 U.S.C. 154(b) by 0 days.

(21) Appl. No.: 12/328,596

(22) Filed: Dec. 4, 2008

(65) Prior Publication Data

US 2009/0112203 A1 Apr. 30, 2009

Related U.S. Application Data

(63) Continuation of application No. 11/117,905, filed on Apr. 29, 2005, which is a continuation of application No. 09/999,851, filed on Oct. 25, 2001, now Pat. No. 7,027,869, which is a continuation-in-part of application No. 09/296,040, filed on Apr. 21, 1999, now Pat. No. 6,411,852, which is a continuation-in-part of application No. 09/095,323, filed on Jun. 10, 1998, application No. 11/117,905, which is a continuation-in-part of application No. 09/436,455, filed on Nov. 8, 1999, now Pat. No. 7,425,212, and a continuation-in-part of application No. 10/232,909, filed on Aug. 30, 2002, now Pat. No. 7,556,624, which is a continuation of application No. 09/349,715, filed on Jul. 8, 1999, now Pat. No. 6,488,673, which is a continuation-in-part of application No. 09/260,401, filed on Mar. 1, 1999, now Pat. No. 6,283,988, which is a continuation-in-part of application No. 09/003,750, filed on Jan. 7, 1998, now Pat. No. 5,972,026, which is a continuation-in-part of application No. 08/833,550, filed on Apr. 7, 1997, now Pat. No. 6,273,907, application No. 09/999, 851, which is a continuation-in-part of application No. 09/535,856, filed on Mar. 27, 2000, now Pat. No. 6,634,363.

(51) Int. Cl.
*A61B 19/00* (2006.01)
(52) U.S. Cl. ...................... 128/898; 607/101
(58) Field of Classification Search .................. 607/88, 607/89, 92, 101, 102; 128/898; 606/15
See application file for complete search history.

(56) References Cited

U.S. PATENT DOCUMENTS 1,155,169 A 9/1915 Starkweather (Continued)

FOREIGN PATENT DOCUMENTS

DE 19529634 A1 2/1997

(Continued)

OTHER PUBLICATIONS

An, S S. et al., "Airway smooth muscle dynamics: a common pathway of airway obstruction in asthma", European Respiratory Journal, 2007, pp. 834-860, vol. 29—No. 5.

(Continued)

*Primary Examiner*—Ahmed M Farah
(74) *Attorney, Agent, or Firm*—Perkins Coie LLP

(57) ABSTRACT

Methods of increasing gas exchange performed by the lung by damaging lung cells, damaging tissue, causing trauma, and/or destroying airway smooth muscle tone with an apparatus inserted into an airway of the lung. The damaging of lung cells, damaging tissue, causing trauma, and destroying airway smooth muscle tone with the apparatus may be any one of or combinations of the following: heating the airway; cooling the airway; delivering a liquid to the airway; delivering a gas to the airway; puncturing the airway; tearing the airway; cutting the airway; applying ultrasound to the airway; and applying ionizing radiation to the airway.

2 Claims, 36 Drawing Sheets

U.S. PATENT DOCUMENTS

| | | |
|---|---|---|
| 1,207,479 A | 12/1916 | Bisgaard |
| 2,072,346 A | 3/1937 | Smith |
| 3,568,659 A | 3/1971 | Karnegis |
| 3,667,476 A | 6/1972 | Muller |
| 3,692,029 A | 9/1972 | Adair |
| 3,995,617 A | 12/1976 | Watkins et al. |
| 4,116,589 A | 9/1978 | Rishton |
| 4,129,129 A | 12/1978 | Amrine |
| 4,461,283 A | 7/1984 | Doi |
| 4,502,490 A | 3/1985 | Evans et al. |
| 4,522,212 A | 6/1985 | Gelinas et al. |
| 4,557,272 A | 12/1985 | Carr |
| 4,565,200 A | 1/1986 | Cosman |
| 4,567,882 A | 2/1986 | Heller |
| 4,584,998 A | 4/1986 | McGrail |
| 4,612,934 A | 9/1986 | Borkan |
| 4,621,642 A | 11/1986 | Chen |
| 4,621,882 A | 11/1986 | Krumme |
| 4,625,712 A | 12/1986 | Wampler |
| 4,646,737 A | 3/1987 | Hussein et al. |
| 4,674,497 A | 6/1987 | Ogasawara |
| 4,683,890 A | 8/1987 | Hewson |
| 4,704,121 A | 11/1987 | Moise |
| 4,706,688 A | 11/1987 | Don Michael et al. |
| 4,709,698 A | 12/1987 | Johnston et al. |
| 4,772,112 A | 9/1988 | Zider et al. |
| 4,779,614 A | 10/1988 | Moise |
| 4,790,305 A | 12/1988 | Zoltan et al. |
| 4,799,479 A | 1/1989 | Spears |
| 4,802,492 A | 2/1989 | Grunstein |
| 4,817,586 A | 4/1989 | Wampler |
| 4,825,871 A | 5/1989 | Cansell |
| 4,827,935 A | 5/1989 | Geddes et al. |
| 4,846,152 A | 7/1989 | Wampler et al. |
| 4,862,886 A | 9/1989 | Clarke et al. |
| 4,895,557 A | 1/1990 | Moise et al. |
| 4,906,229 A | 3/1990 | Wampler |
| 4,920,978 A | 5/1990 | Colvin |
| 4,944,722 A | 7/1990 | Carriker et al. |
| 4,955,377 A | 9/1990 | Lennox et al. |
| 4,969,865 A | 11/1990 | Hwang et al. |
| 4,976,709 A | 12/1990 | Sand |
| 4,985,014 A | 1/1991 | Orejola |
| 4,991,603 A | 2/1991 | Cohen et al. |
| 5,009,936 A | 4/1991 | Yamanaka et al. |
| 5,019,075 A | 5/1991 | Spears et al. |
| 5,030,645 A | 7/1991 | Kollonitsch |
| 5,036,848 A | 8/1991 | Hewson |
| 5,053,033 A | 10/1991 | Clarke |
| 5,056,519 A | 10/1991 | Vince |
| 5,074,860 A | 12/1991 | Gregory et al. |
| 5,084,044 A | 1/1992 | Quint |
| 5,096,916 A | 3/1992 | Skupin |
| 5,100,388 A | 3/1992 | Behl et al. |
| 5,100,423 A | 3/1992 | Fearnot |
| 5,103,804 A | 4/1992 | Abele et al. |
| 5,105,826 A | 4/1992 | Smits et al. |
| 5,107,830 A | 4/1992 | Younes |
| 5,116,864 A | 5/1992 | March et al. |
| 5,117,828 A | 6/1992 | Metzger et al. |
| 5,135,517 A | 8/1992 | McCoy |
| 5,152,286 A | 10/1992 | Sitko et al. |
| 5,167,223 A | 12/1992 | Koros et al. |
| 5,170,803 A | 12/1992 | Hewson et al. |
| 5,174,288 A | 12/1992 | Bardy et al. |
| 5,191,883 A | 3/1993 | Lennox et al. |
| 5,213,576 A | 5/1993 | Abiuso et al. |
| 5,215,103 A | 6/1993 | Desai |
| 5,231,996 A | 8/1993 | Bardy et al. |
| 5,232,444 A | 8/1993 | Just et al. |
| 5,234,456 A | 8/1993 | Silvestrini |
| 5,254,088 A | 10/1993 | Lundquist et al. |
| 5,255,678 A | 10/1993 | Deslauriers et al. |
| 5,255,679 A | 10/1993 | Imran |
| 5,265,604 A | 11/1993 | Vince |
| 5,269,758 A | 12/1993 | Taheri |
| 5,281,218 A | 1/1994 | Imran |
| 5,293,869 A | 3/1994 | Edwards et al. |
| 5,309,910 A | 5/1994 | Edwards et al. |
| 5,313,943 A | 5/1994 | Houser et al. |
| 5,345,936 A | 9/1994 | Pomeranz et al. |
| 5,368,591 A | 11/1994 | Lennox et al. |
| 5,370,679 A | 12/1994 | Atlee, III |
| 5,374,287 A | 12/1994 | Rubin |
| 5,383,917 A | 1/1995 | Desai et al. |
| 5,393,207 A | 2/1995 | Maher et al. |
| 5,394,880 A | 3/1995 | Atlee, III |
| 5,396,887 A | 3/1995 | Imran |
| 5,400,778 A | 3/1995 | Jonson et al. |
| 5,400,783 A | 3/1995 | Pomeranz et al. |
| 5,411,025 A | 5/1995 | Webster, Jr. |
| 5,415,166 A | 5/1995 | Imran |
| 5,415,656 A | 5/1995 | Tihon et al. |
| 5,417,687 A | 5/1995 | Nardella et al. |
| 5,423,744 A | 6/1995 | Gencheff et al. |
| 5,423,811 A | 6/1995 | Imran et al. |
| 5,425,811 A | 6/1995 | Mashita |
| 5,431,696 A | 7/1995 | Atlee, III |
| 5,433,730 A | 7/1995 | Alt |
| 5,443,470 A | 8/1995 | Stern et al. |
| 5,454,782 A | 10/1995 | Perkins |
| 5,456,667 A | 10/1995 | Ham et al. |
| 5,458,596 A | 10/1995 | Lax et al. |
| 5,465,717 A | 11/1995 | Imran et al. |
| 5,471,982 A | 12/1995 | Edwards et al. |
| 5,478,309 A | 12/1995 | Sweezer et al. |
| 5,496,311 A | 3/1996 | Abele et al. |
| 5,500,011 A | 3/1996 | Desai |
| 5,505,728 A | 4/1996 | Ellman et al. |
| 5,507,791 A | 4/1996 | Sit'ko |
| 5,509,419 A | 4/1996 | Edwards et al. |
| 5,522,862 A | 6/1996 | Testerman et al. |
| 5,531,779 A | 7/1996 | Dahl et al. |
| 5,540,681 A | 7/1996 | Strul et al. |
| 5,545,161 A | 8/1996 | Imran |
| 5,545,193 A | 8/1996 | Fleischman et al. |
| 5,549,559 A | 8/1996 | Eshel |
| 5,549,655 A | 8/1996 | Erickson |
| RE35,330 E | 9/1996 | Malone et al. |
| 5,558,073 A | 9/1996 | Pomeranz et al. |
| 5,562,608 A | 10/1996 | Sekins et al. |
| 5,571,074 A | 11/1996 | Buckman, Jr. et al. |
| 5,578,072 A | 11/1996 | Barone et al. |
| 5,588,432 A | 12/1996 | Crowley |
| 5,588,812 A | 12/1996 | Taylor et al. |
| 5,595,183 A | 1/1997 | Swanson et al. |
| 5,598,848 A | 2/1997 | Swanson et al. |
| 5,601,088 A | 2/1997 | Swanson et al. |
| 5,605,157 A | 2/1997 | Panescu et al. |
| 5,607,419 A | 3/1997 | Amplatz et al. |
| 5,607,462 A | 3/1997 | Imran |
| 5,620,438 A | 4/1997 | Amplatz et al. |
| 5,624,439 A | 4/1997 | Edwards et al. |
| 5,626,618 A | 5/1997 | Ward et al. |
| 5,630,425 A | 5/1997 | Panescu et al. |
| 5,634,471 A | 6/1997 | Fairfax et al. |
| 5,641,326 A | 6/1997 | Adams |
| 5,647,870 A | 7/1997 | Kordis et al. |
| 5,678,535 A | 10/1997 | DiMarco |
| 5,680,860 A | 10/1997 | Imran |
| 5,681,308 A | 10/1997 | Edwards et al. |
| 5,693,078 A | 12/1997 | Desai et al. |
| 5,699,799 A | 12/1997 | Xu et al. |
| 5,707,218 A | 1/1998 | Maher et al. |

| | | |
|---|---|---|
| 5,707,336 A | 1/1998 | Rubin |
| 5,707,352 A | 1/1998 | Sekins et al. |
| 5,722,401 A | 3/1998 | Pietroski et al. |
| 5,722,403 A | 3/1998 | McGee et al. |
| 5,722,416 A | 3/1998 | Swanson et al. |
| 5,725,525 A | 3/1998 | Kordis |
| 5,727,569 A | 3/1998 | Benetti et al. |
| 5,730,128 A | 3/1998 | Pomeranz et al. |
| 5,730,726 A | 3/1998 | Klingenstein |
| 5,730,741 A | 3/1998 | Horzewski et al. |
| 5,740,808 A | 4/1998 | Panescu et al. |
| 5,741,248 A | 4/1998 | Stern et al. |
| 5,752,518 A | 5/1998 | McGee et al. |
| 5,755,714 A | 5/1998 | Murphy-Chutorian |
| 5,755,753 A | 5/1998 | Knowlton |
| 5,759,158 A | 6/1998 | Swanson |
| 5,765,568 A | 6/1998 | Sweezer, Jr. et al. |
| 5,769,846 A | 6/1998 | Edwards et al. |
| 5,772,590 A | 6/1998 | Webster, Jr. |
| 5,779,698 A | 7/1998 | Clayman et al. |
| 5,782,239 A | 7/1998 | Webster, Jr. |
| 5,782,797 A | 7/1998 | Schweich, Jr. et al. |
| 5,782,848 A | 7/1998 | Lennox |
| 5,782,899 A | 7/1998 | Imran |
| 5,792,064 A | 8/1998 | Panescu et al. |
| 5,795,303 A | 8/1998 | Swanson et al. |
| 5,800,375 A | 9/1998 | Sweezer et al. |
| 5,807,306 A | 9/1998 | Shapland et al. |
| 5,810,757 A | 9/1998 | Sweezer, Jr. et al. |
| 5,810,807 A | 9/1998 | Ganz et al. |
| 5,817,073 A | 10/1998 | Krespi |
| 5,820,554 A | 10/1998 | Davis et al. |
| 5,827,277 A | 10/1998 | Edwards |
| 5,833,651 A | 11/1998 | Donovan et al. |
| 5,836,947 A | 11/1998 | Fleischman et al. |
| 5,843,075 A | 12/1998 | Taylor |
| 5,843,077 A | 12/1998 | Edwards |
| 5,846,238 A | 12/1998 | Jackson et al. |
| 5,848,969 A | 12/1998 | Panescu et al. |
| 5,848,972 A | 12/1998 | Triedman et al. |
| 5,849,026 A | 12/1998 | Zhou et al. |
| 5,855,577 A | 1/1999 | Murphy-Chutorian et al. |
| 5,860,974 A | 1/1999 | Abele |
| 5,863,291 A | 1/1999 | Schaer |
| 5,865,791 A | 2/1999 | Whayne et al. |
| 5,868,740 A | 2/1999 | LeVeen et al. |
| 5,871,443 A | 2/1999 | Edwards et al. |
| 5,871,523 A | 2/1999 | Fleischman et al. |
| 5,873,865 A | 2/1999 | Horzewski et al. |
| 5,881,727 A | 3/1999 | Edwards |
| 5,882,346 A | 3/1999 | Pomeranz et al. |
| 5,891,136 A | 4/1999 | McGee et al. |
| 5,897,554 A | 4/1999 | Chia et al. |
| 5,899,882 A | 5/1999 | Waksman et al. |
| 5,904,651 A | 5/1999 | Swanson et al. |
| 5,904,711 A | 5/1999 | Flom et al. |
| 5,908,445 A | 6/1999 | Whayne et al. |
| 5,908,446 A | 6/1999 | Imran |
| 5,911,218 A | 6/1999 | DiMarco |
| 5,919,172 A | 7/1999 | Golba, Jr. |
| 5,935,079 A | 8/1999 | Swanson et al. |
| 5,941,869 A | 8/1999 | Patterson et al. |
| 5,951,546 A | 9/1999 | Lorentzen |
| 5,954,661 A | 9/1999 | Greenspon et al. |
| 5,954,662 A | 9/1999 | Swanson et al. |
| 5,957,961 A | 9/1999 | Maguire et al. |
| 5,964,753 A | 10/1999 | Edwards |
| 5,964,796 A | 10/1999 | Imran |
| 5,971,983 A | 10/1999 | Lesh |
| 5,972,026 A * | 10/1999 | Laufer et al. ............ 607/96 |
| 5,979,456 A | 11/1999 | Magovern |
| 5,984,917 A | 11/1999 | Fleischman et al. |
| 5,991,650 A | 11/1999 | Swanson et al. |
| 5,992,419 A | 11/1999 | Sterzer et al. |
| 5,993,462 A | 11/1999 | Pomeranz et al. |
| 5,999,855 A | 12/1999 | DiMarco |
| 6,004,269 A | 12/1999 | Crowley et al. |
| 6,009,877 A | 1/2000 | Edwards |
| 6,010,500 A | 1/2000 | Sherman et al. |
| 6,016,437 A | 1/2000 | Tu et al. |
| 6,024,740 A | 2/2000 | Lesh et al. |
| 6,036,687 A | 3/2000 | Laufer et al. |
| 6,045,550 A | 4/2000 | Simpson et al. |
| 6,053,172 A | 4/2000 | Hovda et al. |
| 6,071,280 A | 6/2000 | Edwards et al. |
| 6,071,281 A | 6/2000 | Burnside et al. |
| 6,083,255 A * | 7/2000 | Laufer et al. ............ 607/96 |
| 6,092,528 A | 7/2000 | Edwards |
| 6,142,993 A | 11/2000 | Whayne et al. |
| 6,152,899 A | 11/2000 | Farley et al. |
| 6,198,970 B1 | 3/2001 | Freed et al. |
| 6,200,333 B1 | 3/2001 | Laufer |
| 6,254,598 B1 | 7/2001 | Edwards et al. |
| 6,273,907 B1 | 8/2001 | Laufer |
| 6,283,988 B1 | 9/2001 | Laufer et al. |
| 6,283,989 B1 | 9/2001 | Laufer et al. |
| 6,299,633 B1 | 10/2001 | Laufer |
| 6,338,836 B1 | 1/2002 | Kuth et al. |
| 6,411,852 B1 * | 6/2002 | Danek et al. ............ 607/42 |
| 6,416,740 B1 | 7/2002 | Unger |
| 6,423,105 B1 | 7/2002 | Iijima et al. |
| 6,440,129 B1 | 8/2002 | Simpson |
| 6,488,673 B1 | 12/2002 | Laufer et al. |
| 6,634,363 B1 | 10/2003 | Danek et al. |
| 7,027,869 B2 | 4/2006 | Danek et al. |
| 7,104,987 B2 | 9/2006 | Biggs et al. |
| 7,198,635 B2 * | 4/2007 | Danek et al. ............ 607/96 |
| 7,264,002 B2 | 9/2007 | Danek et al. |
| 7,273,055 B2 | 9/2007 | Danek et al. |
| 7,425,212 B1 * | 9/2008 | Danek et al. ............ 606/47 |
| 2003/0159700 A1 | 8/2003 | Laufer et al. |
| 2005/0010270 A1 | 1/2005 | Laufer |
| 2005/0171396 A1 | 8/2005 | Pankratov et al. |
| 2007/0106296 A1 | 5/2007 | Laufer et al. |

FOREIGN PATENT DOCUMENTS

| | | |
|---|---|---|
| EP | 189329 A3 | 6/1987 |
| EP | 286145 A3 | 10/1990 |
| EP | 282225 B1 | 6/1992 |
| EP | 908713 A1 | 4/1999 |
| EP | 908150 B1 | 5/2003 |
| EP | 768091 B1 | 7/2003 |
| FR | 2659240 B1 | 7/1997 |
| GB | 2233293 | 2/1994 |
| RU | 2053814 C1 | 2/1996 |
| RU | 2091054 C1 | 9/1997 |
| SU | 545358 T | 2/1977 |
| WO | WO-9733715 A1 | 9/1997 |
| WO | WO-9737715 A1 | 10/1997 |
| WO | WO-9844854 A1 | 10/1998 |
| WO | WO-9856234 A1 | 12/1998 |
| WO | WO-9856324 A1 | 12/1998 |
| WO | WO-9903413 A1 | 1/1999 |
| WO | WO-9858681 A3 | 3/1999 |
| WO | WO-9913779 A2 | 3/1999 |
| WO | WO-9934741 A1 | 7/1999 |
| WO | WO-9944506 A1 | 9/1999 |
| WO | WO-9945855 A1 | 9/1999 |
| WO | WO-0051510 A1 | 9/2000 |
| WO | WO-0103642 A1 | 1/2001 |
| WO | WO-0232334 A1 | 4/2002 |

OTHER PUBLICATIONS

Bel et al., "Hot stuff: bronchial thermoplasty for asthma", American Journal of Respiratory and Critical Care Medicine, 2006, pp. 941-943, vol. 173.

Brown, R.H. et al., "Effect of bronchial thermoplasty on airway distensibility", European Respiratory Journal, 2005, pp. 277-282, vol. 26—No. 2.

Brown, R.H. et al., "In vivo evaluation of the effectiveness of bronchial thermoplasty with computed tomography", Journal of Applied Physiology, 2005, pp. 1603-1606, vol. 98.

Chhajed, p. et al., "Will there be a role for bronchoscopic radiofrequency ablation?", J Bronchol, 2005, pp. 184-186, vol. 12 No. 3.

Co-pending U.S. Appl. No. 09/095323.

Co-pending U.S. Appl. No. 09/244173.

Cox, G. et al., "Bronchial Thermoplasty for Asthma", American Journal of Respiratory and Critical Care Medicine, 2006, pp. 965-969, vol. 173.

Cox, G. et al., "Bronchial Thermoplasty: Long-Term Follow-Up and Patient Satisfaction", Chest, 2004, p. 822s, vol. 126 No. 4.

Cox, G. et al., "Bronchial Thermoplasty: One-Year Update", Am J Respir Crit Care Med, 2004, p. A313, vol. 169.

Cox, G. et al., "Development of a Novel Bronchoscopic Therapy for Asthma", Journal of Allergy and Clinical Immunology, 2003, p. S33, vol. 113—Issue 2.

Cox, G. et al., "Early Clinical Experience with Bronchial Thermoplasty for the Treatment of Asthma", American Thoracic Society Annual Meeting, 2002, p. 1068.

Cox, G. et al., "Impact of bronchial thermoplasty on asthma status: interim results from the AIR trial", European Respiratory Society Annual Meeting, 2006, p. 1.

Cox, G. et al., "Radiofrequency ablation of airway smooth muscle for sustained treatment of asthma: preliminary investigations", European Respiratory Journal, 2004, pp. 659-663, vol. 24.

Cox, Gerard et al., "Asthma Control during the Year after Bronchial Thermoplasty", The New England journal of medicine, 2007, pp. 1327-1337, vol. 356 No. 13.

Cox, Gerard et al., "Clinical Experience With Bronchial Thermoplasty for the Treatment of Asthma", Chest, 2003, p. 1068, vol. 124.

Danek, C.J. et al., "Asthma Intervention Research (AIR) Trial Evaluating Bronchial Thermoplasty™: Early Results", American Thoracic Society Annual Meeting, 2002, p. 1.

Danek, C.J. et al., "Bronchial thermoplasty reduces canine airway responsiveness to local methacholine challenge", American Thoracic Society Annual Meeting, 2002, p. 1.

Danek, Christopher J. et al., "Reduction in airway hyperresponsiveness to methacholine by the application of RF energy in dogs", J Appl Physiol, 2004, pp. 1946-1953, vol. 97.

Dierkesmann et al., "Indication and Results of Endobronchial Laser Therapy", Lung, 1990, pp. 1095-1102, vol. 168—No. 1, Springer, New York.

Hogg, James C. et al., "The Pathology of Asthma", APMIS, 1997, pp. 735-745, vol. 105—No. 10.

Ivanyuta, O. M. et al., "Effect of Low-Power Laser Irradiation of Bronchial Mucosa on the State of Systemic and Local Immunity in Patients with Chronic Bronchitis", Problemy Tuberkuleza, 1991, pp. 26-29, vol. 6.

Laviolette et al., "Asthma Intervention Research (Air) Trial: Early Safety Assessment Of Bronchial Thermoplasty", Am J Respir Crit Care Med, 2004, p. A314, vol. 169.

Leff et al., "Bronchial Thermoplasty Alters Airway Smooth Muscle and Reduces Responsiveness in Dogs: A Possible Procedure for the Treatment of Asthma", American Thoracic Society Annual Meeting, 2002, p. 1.

Lim, Erle C.H. et al., "Botulinum toxin: a novel therapeutic option for bronchial asthma?", Medical Hypotheses, 2006, pp. 915-919, vol. 66.

Lombard et al., "Histologic Effects of Bronchial Thermoplasty of Canine and Human Airways", American Thoracic Society Annual Meeting, 2002, p. 1.

Macklem, p. T., "Mechanical Factors Determining Maximum Bronchoconstriction", European Respiratory Journal, 1989, pp. 156s-159s, vol. 6.

Mayse, Martin L. et al., "Clinical Pearls for Bronchial Thermoplasty", J Bronchol, 2007, pp. 115-123, vol. 14—No. 2.

Miller, J.D. et al., "A Prospective Feasibility Study of Bronchial Thermoplasty in the Human Airway", Chest, 2005, pp. 1999-2006, vol. 127 No. 6.

Miller, J.D. et al., "Bronchial Thermoplasty is Well Tolerated by Non-Asthmatic Patients Requiring Lobectomym", American Thoracic Society Annual Meeting, 2002, p. 1.

Netter, F. H., "Respiratory System: a Compilation of Paintings Depicting Anatomy and Embryology, Physiology, Pathology, Pathophysiology, and Clinical Features and Treatment of Diseases", In The CIBA Collection of Medical Illustrations M.B. Divertie, ed., Summit: New Jersey, 1979, pp. 119-135, vol. 7.

Provotorov et al., "The Clinical Efficacy of Treating Patients with Nonspecific Lung Disease by Using Low-energy Laser Irradiation and Intrapulmonary Drug Administration", Terapevticheskii Arkhiv (USSR), 1991, pp. 18-23, vol. 62—No. 12, ISSN: 0040-3660.

Rubin et al., "Bronchial thermoplasty improves asthma status of moderate to severe perisstent asthmatics over and above current standard-of-care", American College of Chest Physicians, 2006, pp. 2.

Shesterina, M. V. et al., "Effect of laser therapy on immunity in patients with bronchial asthma and pulmonary tuberculosis", 1993, pp. 23-26.

Simon, R. Johnson et al., "Synthetic Functions of Airway Smooth Muscle in Asthma", Trends Pharmacol. Sci., 1997, pp. 288-292, vol. 18—No. 8, Elsevier.

Solway, Julian., "Airway Smooth Muscle as a Target for Asthma Therapy", The New England journal of medicine, 2007, pp. 1367-1369, vol. 356 No. 13.

Sterk, Peter J. et al., "Heterogeneity of airway hyperresponsiveness: time for unconventional, but traditional", studies, J Appl Physiol, 2004, pp. 2017-2018, vol. 96.

Toma et al., "Brave new world for interventional bronchoscopy", Thorax, 2005, pp. 180-181, vol. 60.

Trow, Terence K., "Clinical Year in Review I Diagnostic Imaging, Asthma, Lung Transplantation, and Interventional Pulmonology", Proceedings of the American Thoracic Society, 2006, pp. 553-556, vol. 3.

Vasilotta, p. L. et al., "I-R Laser: A new therapy in Rhino-Sino-Nasal bronchial syndrome with asthmatic component", American Society for Laser medicine and Surgery abstracts, p. 74.

Vorotnev et al., "Low energy laser treatment of chronic obstructive bronchitis in a general rehabilitation center", Terapevticheskii Arkhiv, 1997, pp. 17-19, vol. 69—No. 3, ISSN: 0040-3660.

Wiggs, B.R. et al., "On the Mechanism of Mucosal Folding in Normal and Asthmatic Airways", J. Appl. Physiol., 1997, pp. 1814-1821, vol. 83—No. 6.

Wilson, Sandra R. et al., "Global assessment after bronchial thermoplasty: the patient's perspective", Journal of Outcomes Research, 2006, pp. 37-46, vol. 10.

Wizeman et al., "A Computer Model of Thermal Treatment of Airways by Radiofrequency (RF) Energy Delivery", American Thoracic Society Annual Meeting, 2004, p. 1.

* cited by examiner

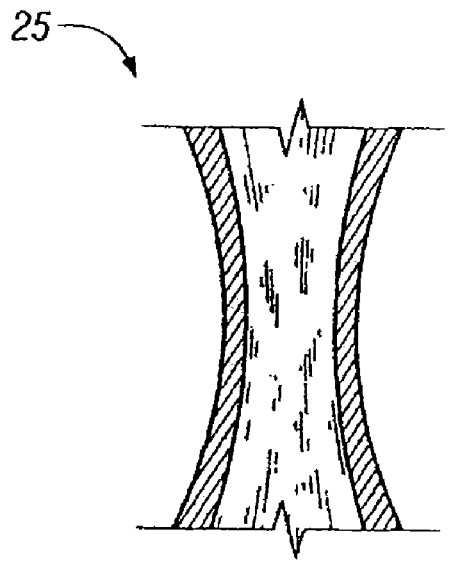 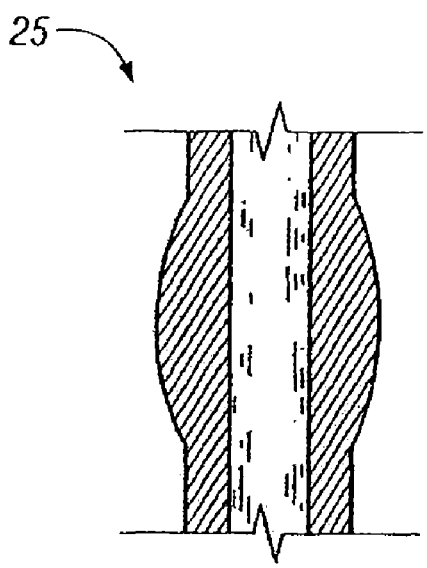
FIG. 6A     FIG. 6B
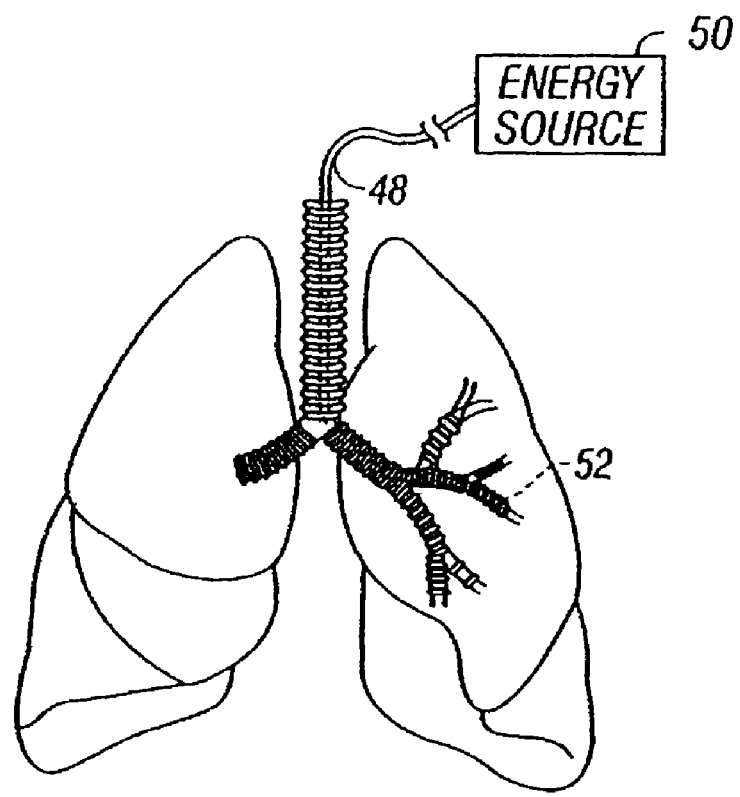
FIG. 7

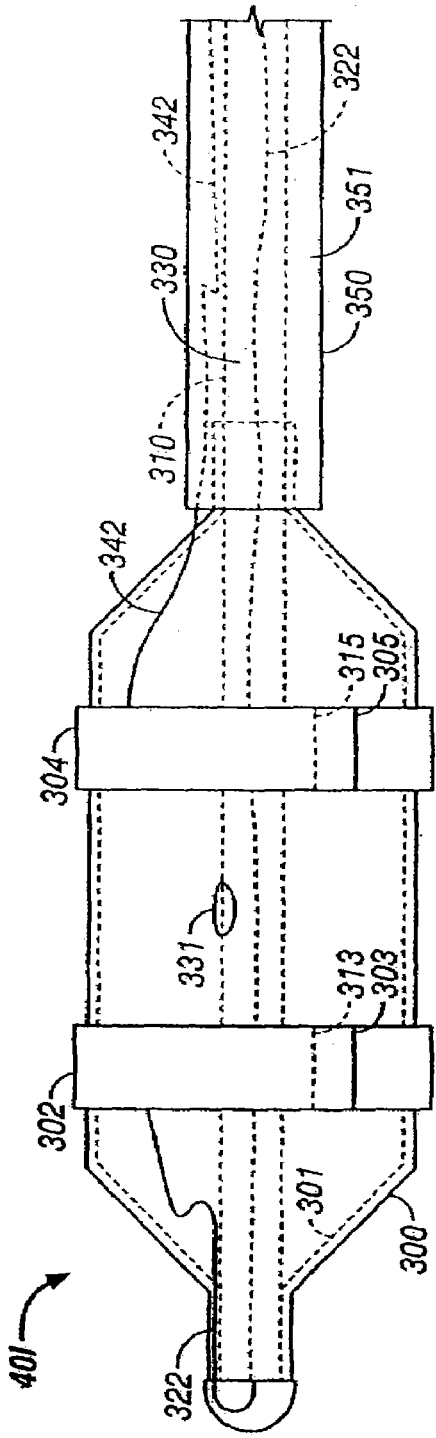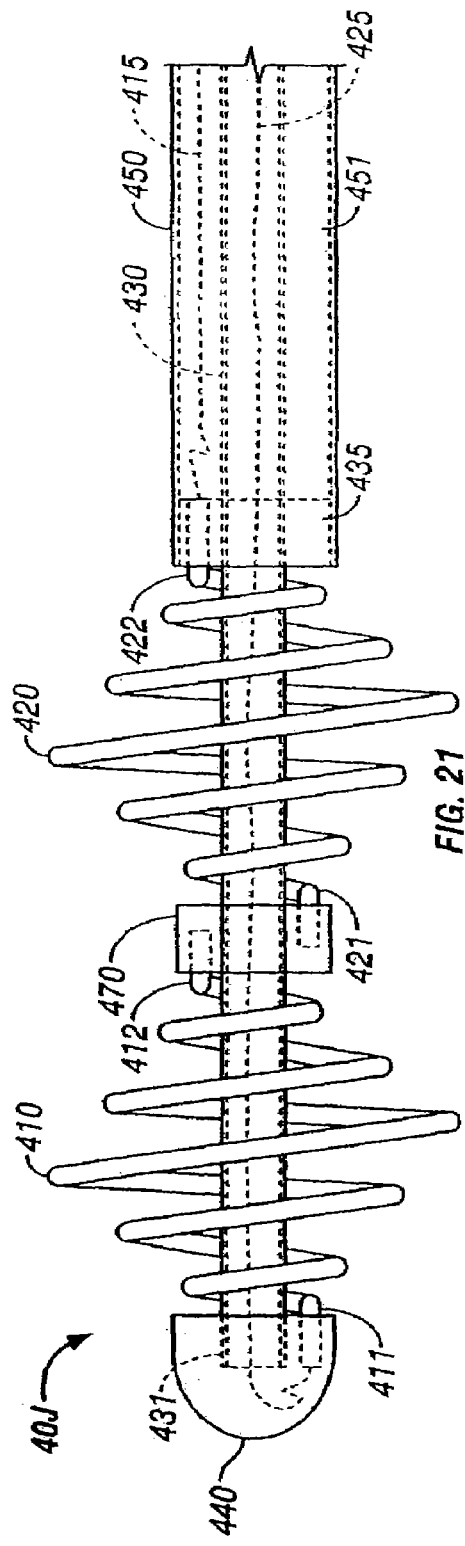

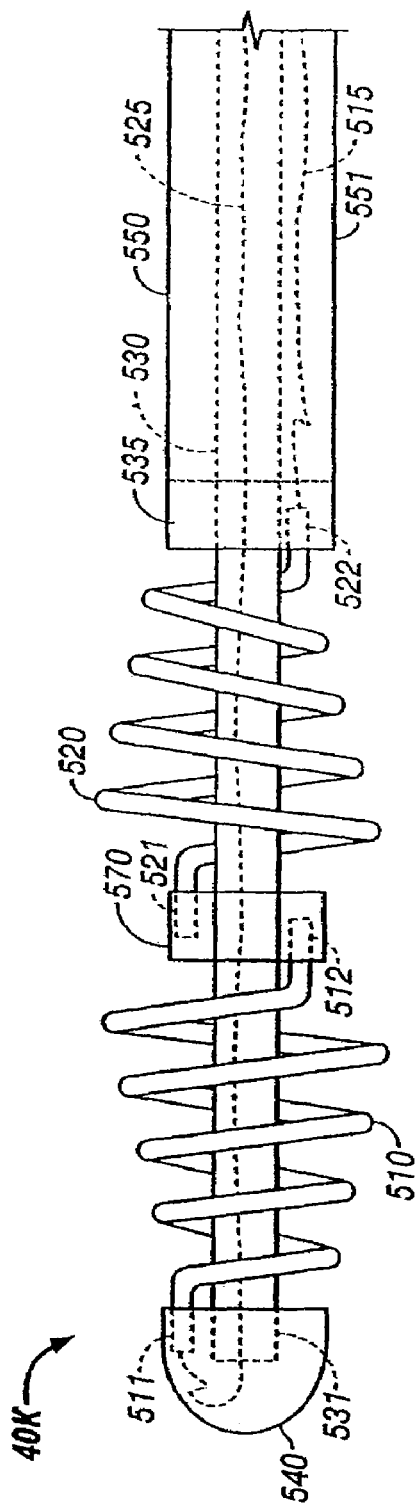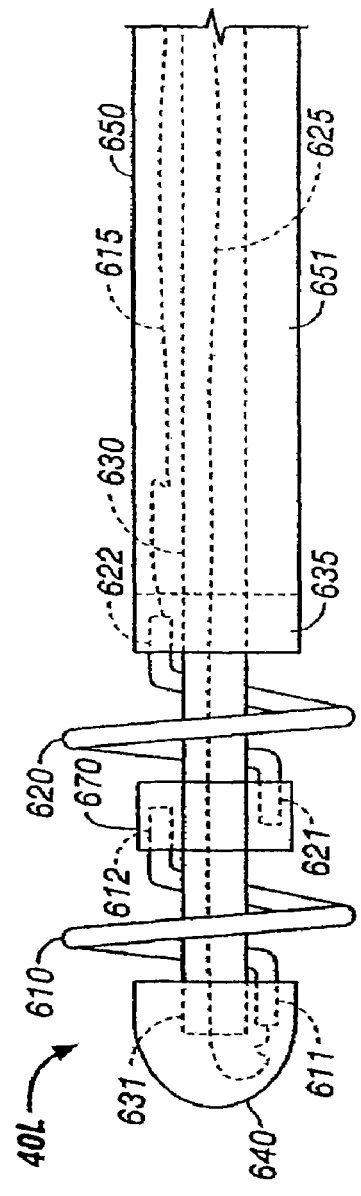

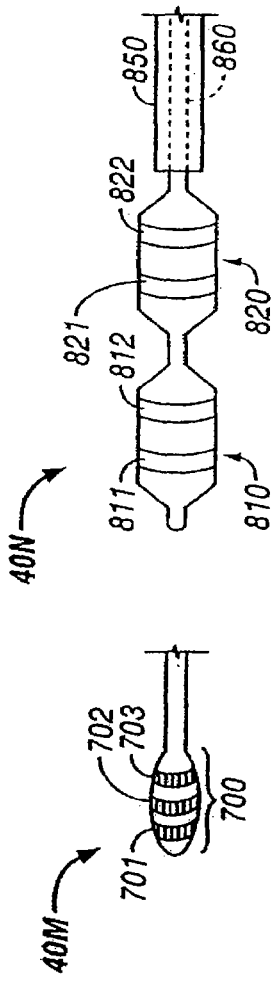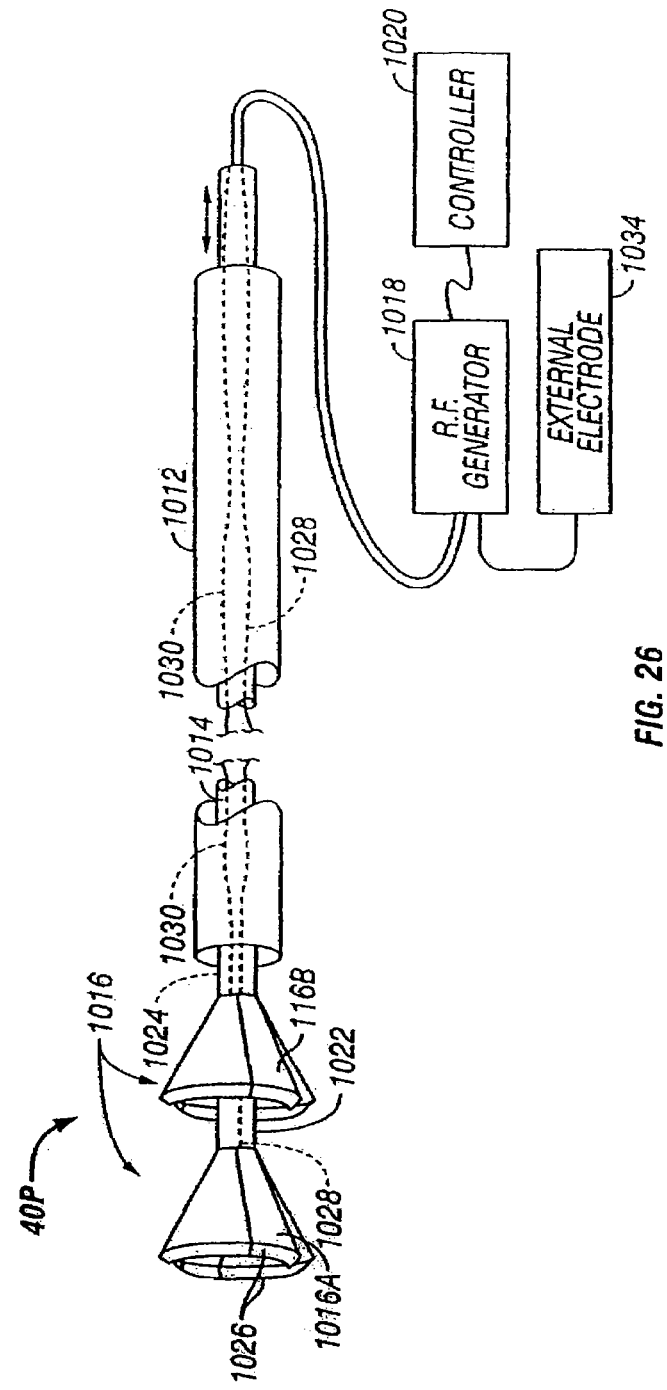
FIG. 24
FIG. 25
FIG. 26

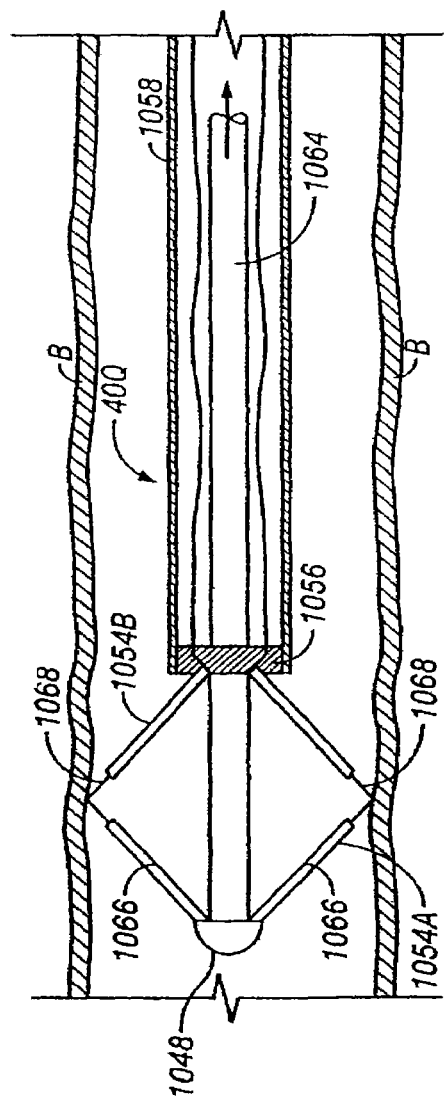
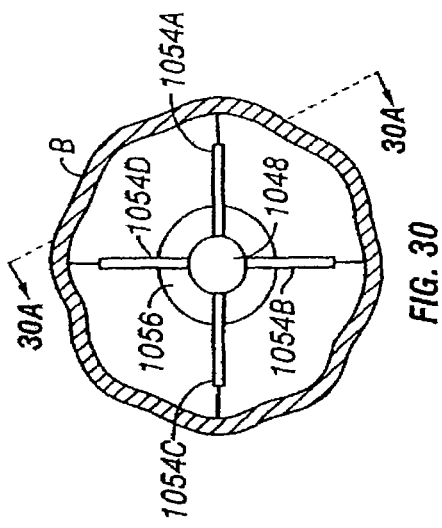
FIG. 29
FIG. 30

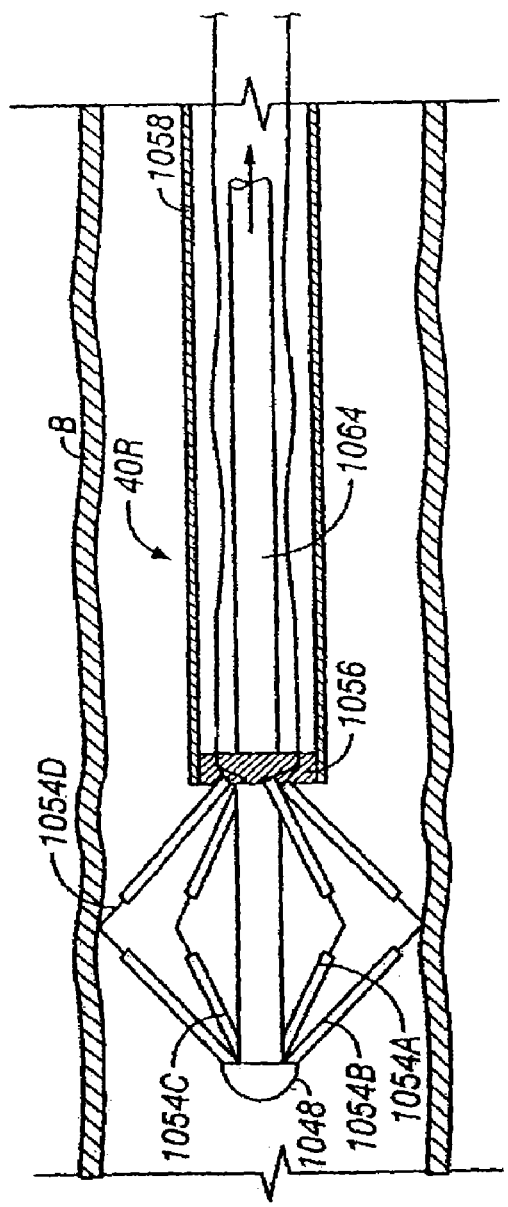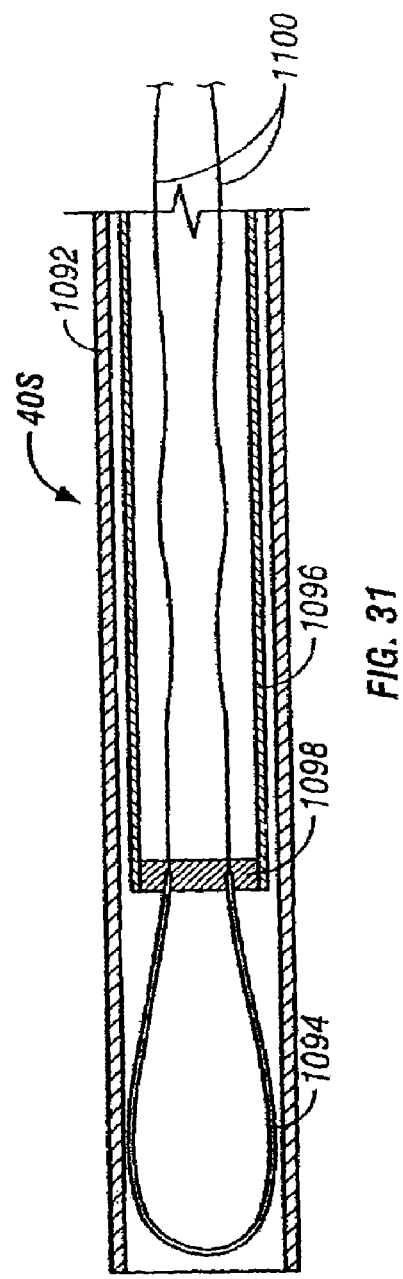

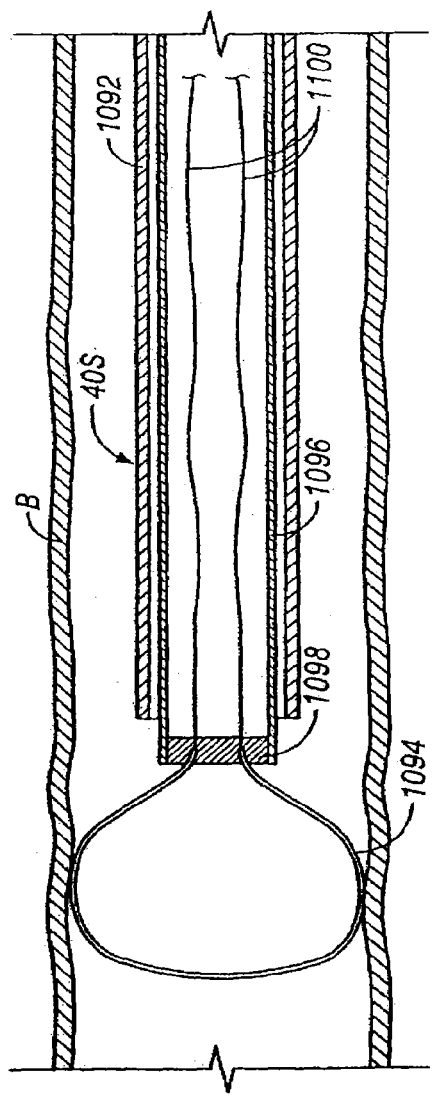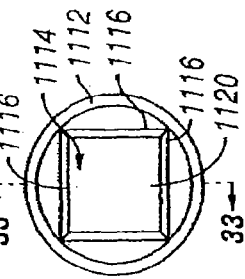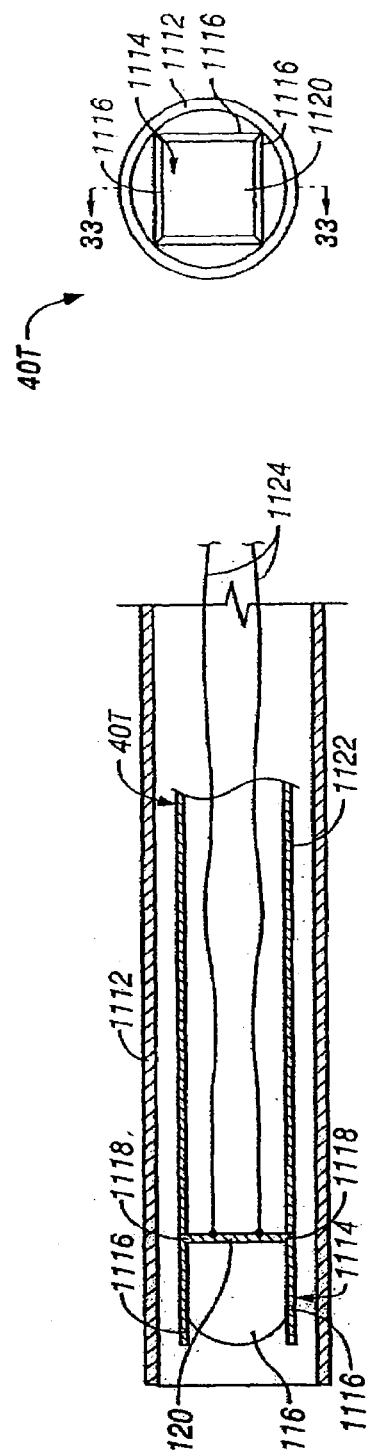

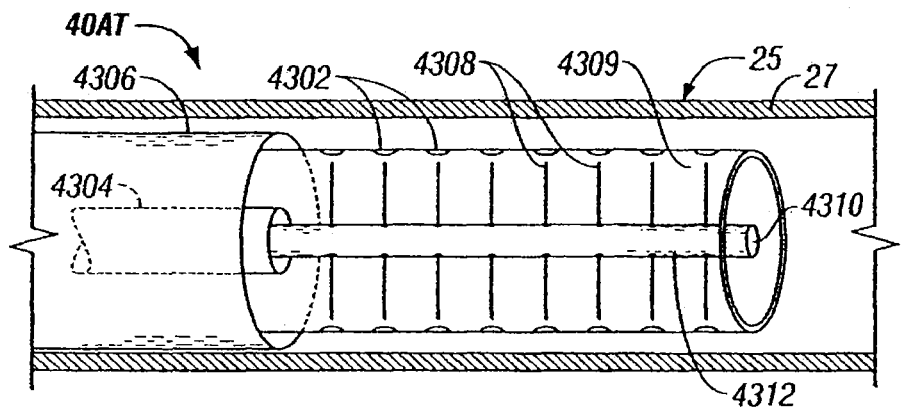
FIG. 63
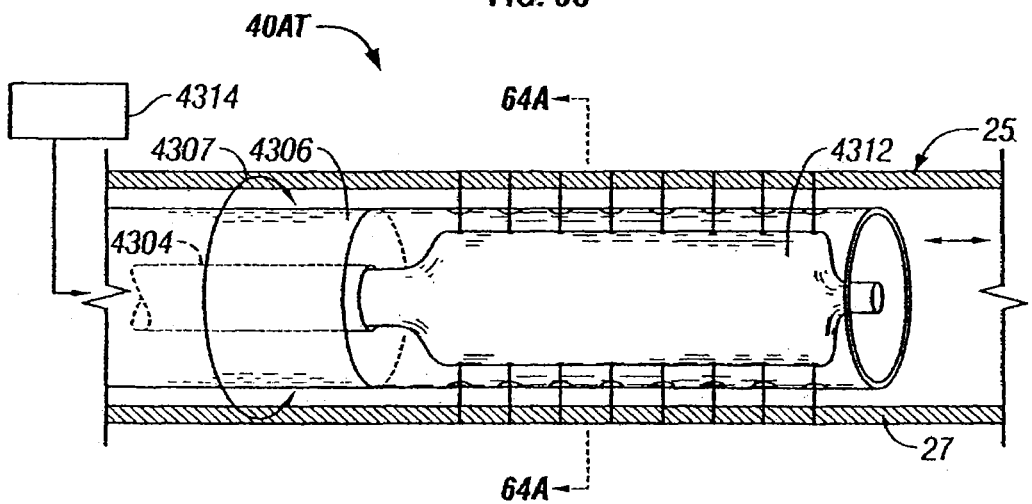
FIG. 64
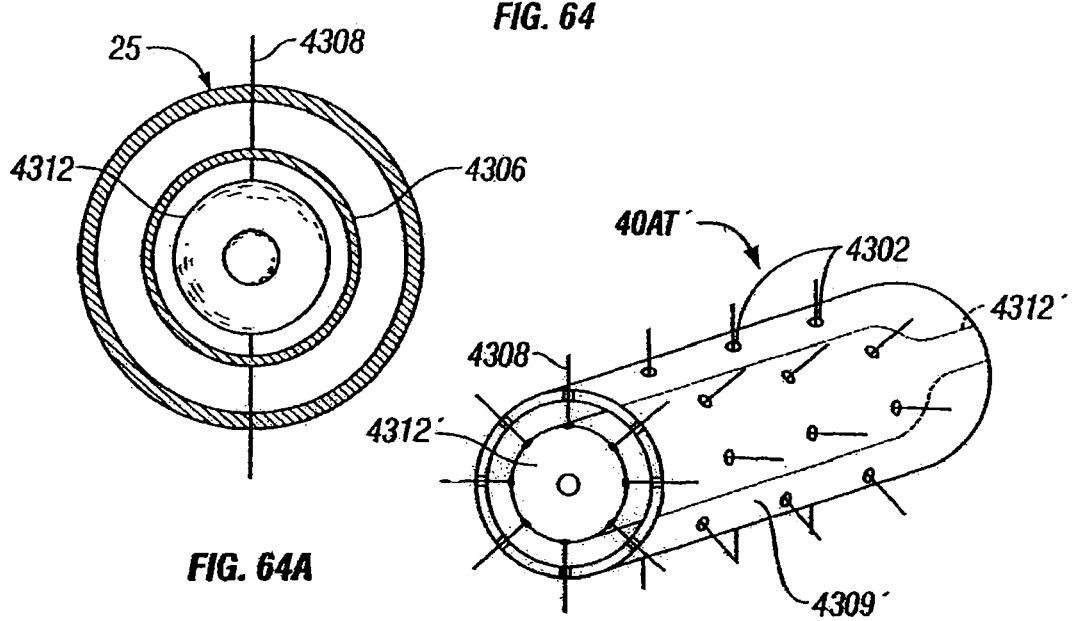
FIG. 64A
FIG. 65

MODIFICATION OF AIRWAYS BY APPLICATION OF MICROWAVE ENERGY

The present application is a continuation of U.S. patent application Ser. No. 11/117,905, filed Apr. 29, 2005, which is:

(a) a continuation application of U.S. application Ser. No. 09/999,851 filed Oct. 25, 2001, now U.S. Pat. No. 7,027,869 B2, which is a continuation-in-part application of U.S. application Ser. No. 09/296,040 filed Apr. 21, 1999, now U.S. Pat. No. 6,411,852 B1, which is a continuation-in-part application of U.S. application Ser. No. 09/095,323 filed Jun. 10, 1998, each of which are herein incorporated by reference in their entirety;

(b) a continuation-in-part application of U.S. application Ser. No. 09/436,455 filed Nov. 8, 1999, now U.S. Pat. No. 7,425,212, which is incorporated by reference herein in its entirety; and (c) a continuation-in-part application of 10/232,909 filed on Aug. 30, 2002, which is a continuation of U.S. application Ser. No. 09/349,715 filed Jul. 8, 1999, now U.S. Pat. No. 6,488,673 B1, which is a continuation-in-part of U.S. application Ser. No. 09/260,401 filed on Mar. 1, 1999, now U.S. Pat. No. 6,283,988, which is a continuation-in-part application of U.S. application Ser. No. 09/003,750 filed Jan. 7, 1998, now U.S. Pat. No. 5,972,026, which is a continuation-in-part application of U.S. application Ser. No. 08/833,550 filed Apr. 7, 1997, now U.S. Pat. No. 6,273,907 B1.

U.S. application Ser. No. 09/999,851, now U.S. Pat. No. 7,027,869 B2, is also a continuation-in-part application of U.S. application Ser. No. 09/535,856 filed on Mar. 27, 2000, and now U.S. Pat. No. 6,634,363, which is also incorporated by reference in its entirety.

BACKGROUND OF THE INVENTION

1. Field of the Invention

The invention relates to a method for treating lung disease, and more particularly, the invention relates to a method of increasing gas exchanging of a lung by stiffening an airway of the lung.

2. Brief Description of the Related Art

The lungs deliver oxygen to the body and remove carbon dioxide. Healthy lung tissue includes a multitude of air passageways which lead to respiratory bronchiole within the lung. These airways eventually lead to small sacs called alveoli, where the oxygen and carbon dioxide are exchanged through the ultra-thin walls of the alveoli. This occurs deep within the lungs, in an area which is accessed by a network of airways, consisting of a series of branching tubes which become narrower, shorter, and more numerous as they penetrate deeper into the lungs. As shown in FIG. 1, tiny air sacks called alveoli 1 surround both alveolar ducts 2 and respiratory bronchiole 3 throughout the lung. The alveoli 1 are small, polyhedral recesses composed of a fibrillated connective tissue and surrounded by a few involuntary muscular and elastic fibers. These alveoli 1 inflate and deflate with air when we breath. The alveoli are generally grouped together in a tightly packed configuration called an alveolar sac. The thin walls of the alveoli 1 perform gas exchange as we inhale and exhale.

During inhalation, as the diaphragm contracts and the ribs are raised, a vacuum is created in the chest, and air is drawn into the lungs. As the diaphragm relaxes, normal lungs act like a stretched balloon and rebound to the normal relaxed state, forcing air out of the lungs. The elasticity of the lungs is maintained by the supportive structure of the alveoli. This network of connective tissue provides strength to the airway walls, as well as elasticity to the lungs, both of which contribute to the lung's ability to function effectively.

Patients with pulmonary disease, such as chronic bronchitis, and emphysema have reduced lung capacity and efficiency, typically due to the breakdown of lung tissue.

In cases of severe chronic pulmonary disease, such as emphysema, lung tissue is destroyed, reducing the strength of the airways. This reduction in strength of the airway walls allows the walls to become "floppy" thereby losing their ability to remain open during exhalation. In the lungs of an emphysema patient, illustrated in FIG. 2, the walls between adjacent alveoli within the alveolar sac deteriorate. This wall deterioration is accelerated by the chemicals in smoke which affect the production of mucus in the lungs. Although the break down of the walls of the alveoli in the lungs occurs over time even in a healthy patient, this deterioration is greatly accelerated in a smoker causing the smoker's lungs to have multiple large spaces 4 with few connecting walls in the place of the much smaller and more dense alveoli spaces 1 in healthy lung tissue.

A cross section of a diseased emphysematous lung will look like Swiss cheese due to the deterioration of the alveoli walls which leaves large spaces in the tissue. In contrast, healthy lung tissue when seen in cross section has no noticeable holes because of the small size of the alveoli. When many of the walls of the alveoli 1 have deteriorated as shown in FIG. 2, the lung has larger open spaces 4 and a larger overall volume, but has less wall tissue to achieve gas exchange.

In this diseased state, the patient suffers from the inability to get the air out of their lungs due to the collapse of the airways during exhalation. Heavily diseased areas of the lung become overinflated. Within the confines of the chest cavity, this overinflation restricts the in-flow of fresh air and the proper function of healthier tissue, resulting in significant breathlessness. Thus, the emphysema patient must take in a greater volume of air to achieve the same amount of gas exchange. When severe emphysema patients take in as much air as their chest cavity can accommodate, they still have insufficient gas exchange because their chest is full of non-functional air filling large cavities in the lungs. Emphysema patients will often look barrel-chested and their shoulders will elevate as they strain to make room for their overinflated lungs to work.

A wide variety of drugs are available for treating the symptoms of pulmonary disease, but none are curative. Chronic bronchitis and emphysema are typically treated with antibiotics and bronchodilators. Unfortunately, a large number of patients are not responsive to these medications or become non-responsive after prolonged periods of treatment.

In severe emphysema cases, lung volume reduction surgery (LVRS) is performed to improve lung efficiency of the patient and allow the patient to regain mobility. In lung volume reduction surgery, a more diseased portion of an emphysematous lung having a large amount of alveolar wall deterioration is surgically removed. LVRS is performed by opening the chest cavity, retracting the ribs, stapling off, and removing the more diseased portion of the lung. This allows the remaining healthier lung tissue to inflate more fully and take greater advantage of the body's ability to inhale and exhale. Because there is more air and more gas exchange in the healthier portion of the lung, lung efficiency is improved.

Lung volume reduction surgery is an extremely invasive procedure requiring the surgical opening of the chest cavity and removal of lung tissue. This surgery has substantial risks of serious post-operative complications, such as pneumothorax, and requires an extended convalescence.

Accordingly, it is desirable to improve air exchange for patients having chronic obstructive pulmonary diseases, such as chronic bronchitis and emphysema. It is especially desirable to achieve improved air exchange of emphysema patients without invasive open chest surgery and the associated complications.

SUMMARY OF THE INVENTION

The present invention pertains to methods of increasing gas exchange of the lungs of a patient. According to the present invention, gas exchange is increased by stiffening, strengthening, or destroying airway smooth muscle tone of at least one airway of a lung.

In accordance with one aspect of the present invention, a method includes: inserting an apparatus into an airway of a lung, and damaging lung cells with the apparatus to cause fibrosis to stiffen the airway so as to increase gas exchange performed by the lung.

In accordance with another aspect of the present invention, a method includes: inserting an apparatus into an airway of a lung; and damaging tissue in the lung with the apparatus to increase gas exchange performed by the lung.

In accordance with a further aspect of the present invention, a method of increasing gas exchange performed by the lung, includes: inserting an apparatus into an airway of a lung; and causing trauma to tissue with the apparatus to cause fibrosis to stiffen the airway. Causing trauma to the tissue with the apparatus includes at least one of: heating the tissue; cooling the tissue; delivering a liquid that cause trauma to the tissue; delivering a gas that cause trauma to the tissue; puncturing the tissue; tearing the tissue; cutting the tissue; applying ultrasound to the tissue; and applying ionizing radiation to the tissue.

Another aspect of the present invention pertains to a method including: inserting an apparatus into an airway of a lung; and destroying airway smooth muscle tone with the apparatus to increase gas exchange performed by the lung.

A further aspect of the present invention pertains to a method of increasing gas exchange performed by a lung. The method includes inserting an apparatus into an airway of a lung, and damaging airway tissue with the apparatus to thicken a wall of the airway.

The present invention provides advantages of a minimally invasive procedure for surgically treating the effects of pulmonary disease, such as chronic pulmonary disease, without the complications associated with conventional surgery.

BRIEF DESCRIPTION OF THE DRAWINGS

The invention will now be described in greater detail with reference to the preferred embodiments illustrated in the accompanying drawings, in which like elements bear like reference numerals, and wherein:

FIG. 6A is a schematic cross-sectional view of the airway of FIG. 6 before treatment taken along the line 6A-6A of FIG. 6;

FIG. 6B is a schematic cross-sectional view of the airway of FIG. 6A after being treated in accordance with one method of the present invention;

FIG. 7 is a schematic side view of lungs being treated with a treatment apparatus in accordance with one embodiment of the present invention;

FIGS. 20A and 20B illustrate an embodiment of a heat treatment apparatus that employs electrodes positioned on the outer surface of a balloon for use with the methods of the present invention;

FIGS. 21, 22, and 23 show embodiments of the heat treatment apparatus that employ diametrically adjustable electrodes for use with the methods of the present invention;

FIG. 24 illustrates a heat treatment apparatus with multiple electrodes for use with the methods of the present invention;

FIG. 25 illustrates a heat treatment apparatus with multiple balloons for use with the methods of the present invention;

FIG. 26 is a schematic side view of one embodiment of a heat treatment apparatus that employs two collapsible and retractable electrodes for use with the methods of the present invention;

FIG. 29 is a side cross-sectional view of the device of FIG. 28 in an enlarged state within a bronchial tube;

FIG. 30 is a side cross-sectional view of an alternative embodiment of a heat treatment apparatus with four electrodes in an enlarged state within a bronchial tube for use with the methods of the present invention;

FIG. 30A is an end view of the device of FIG. 30;

FIG. 31 is a side cross-sectional view of an alternative embodiment of a heat treatment apparatus with a loop shaped electrode in a contracted state for use with the methods of the present invention;

FIG. 32 is a side cross-sectional view of the apparatus of FIG. 31 with the electrode in an expanded state within a bronchial tube for use with the methods of the present invention;

FIG. 33 is a side cross-sectional view of an alternative embodiment of the invention with a plate shape electrode in a contracted state for use with the methods of the present invention;

FIG. 34 is an end view of the apparatus of FIG. 33 in the contracted state;

FIG. 63 illustrates a further embodiment of a treatment apparatus where the treatment apparatus includes a plurality of pins that puncture or penetrate the air way of a lung in accordance with the methods of the present invention;

FIG. 64 illustrates the treatment apparatus of FIG. 63 in a deployed position;

FIG. 64A is a cross-sectional view of the device illustrated in FIG. 64 taken along the line 64A-64A of FIG. 64;

FIG. 65 illustrates an alternative embodiment of the treatment apparatus illustrated in FIGS. 63 and 64 for use with the methods of the present invention;

DETAILED DESCRIPTION OF THE PREFERRED EMBODIMENTS

Figure 1:
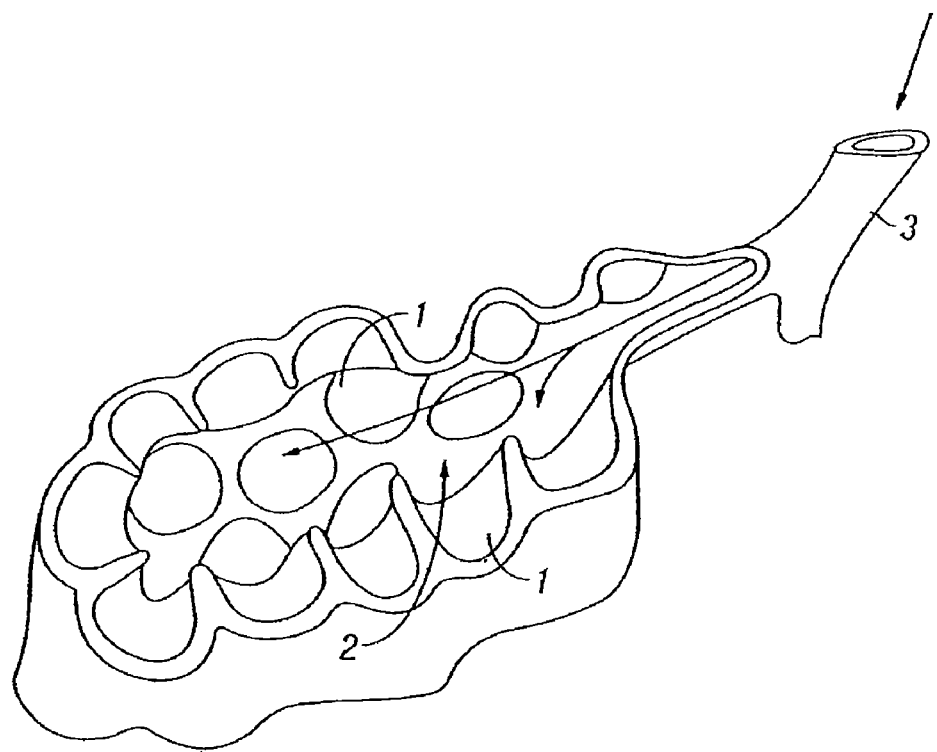
FIG. 1 is a cross-sectional view of an alveolar sack of a healthy lung.
Figure 2:
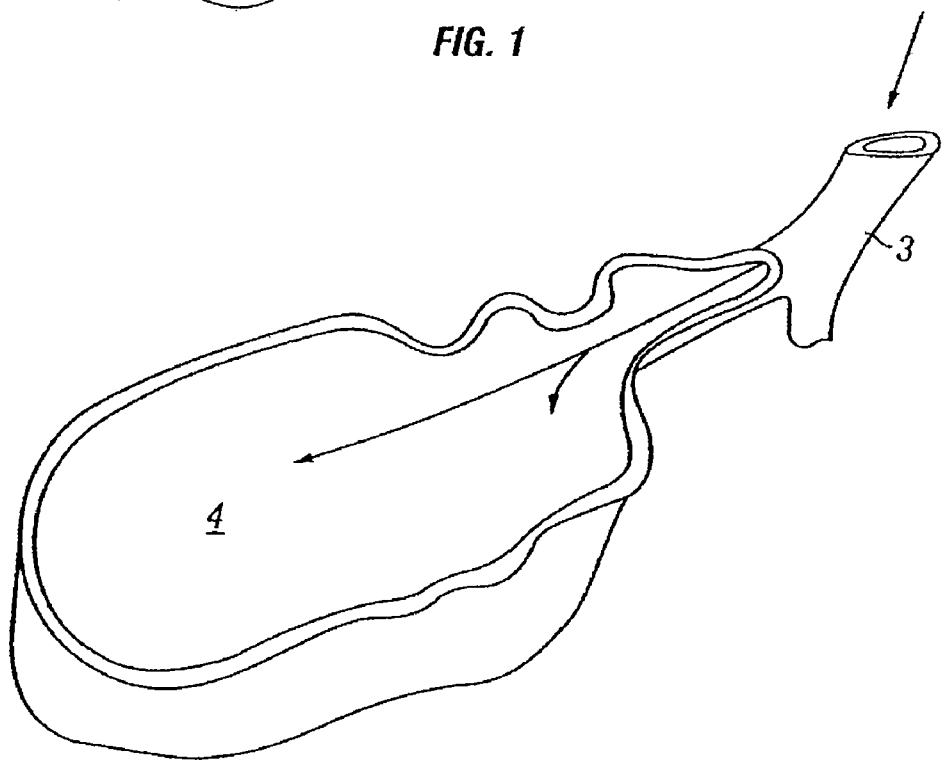
FIG. 2 is a cross-sectional view of an alveolar sack of a diseased lung.

In the following description, like reference numerals refer to like parts.

Figure 3:
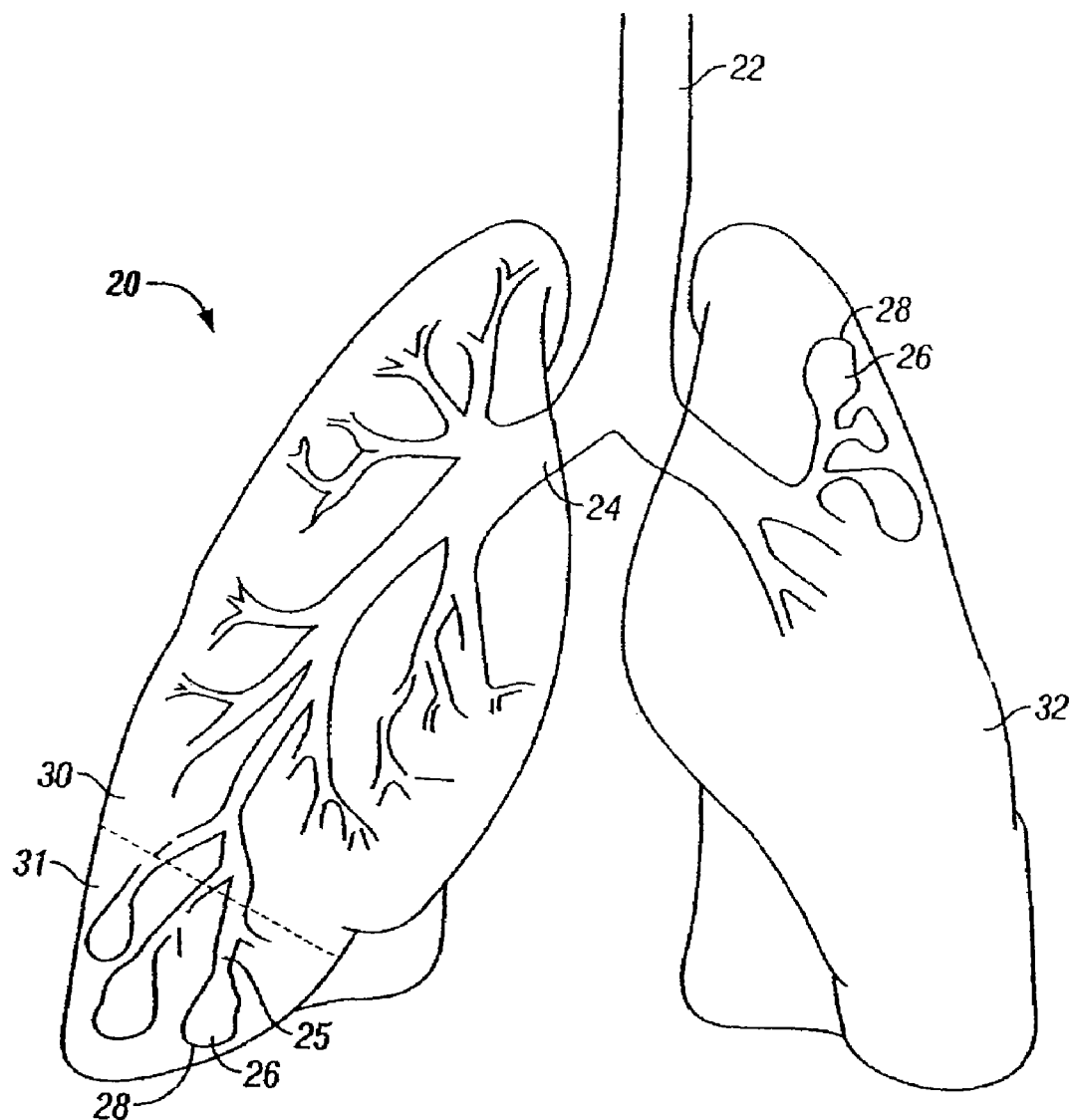
FIG. 3 is an illustration of a lung having a diseased lower portion prior to treatment according to the present invention.

FIG. 3 illustrates human lungs 20 having a left lung 30 and a right lung 32. A diseased portion 31 is located at the lower portion or base of the left lung 30 (indicated by the volume of the lung below the dashed line on the left lung). In some cases, the diseased portions of an unhealthy lung are not generally located in discrete areas. That is, the diseased portions may not be distributed heterogeneously, and are more homogeneous.

As illustrated in FIG. 3, the trachea 22 extends down from the larynx and conveys air to and from the lungs. The trachea 22 divides into right and left main bronchi 24, which in turn form lobar, segmental, and sub-segmental bronchi or bronchial passageways. Eventually, the bronchial tree extends to the terminal bronchiole. At the terminal bronchiole, alveolar sacs 26 contain alveoli 28 that perform gas exchange as humans inhale and exhale.

Figure 4:
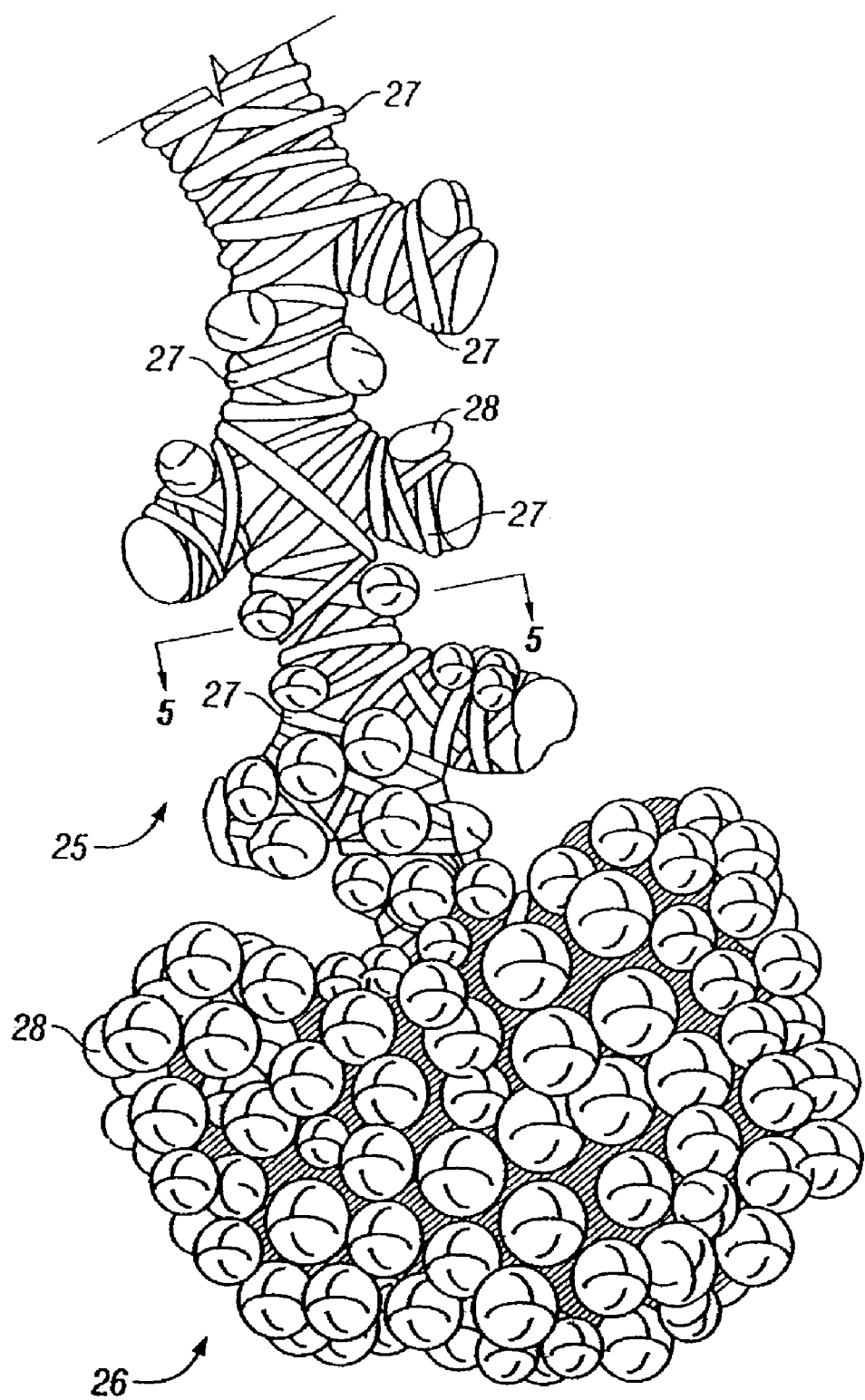
FIG. 4 is a perspective view of the airway of a lung, wherein the smooth muscle tissue, alveolar sacks, and alveoli are illustrated.

FIG. 4 illustrates an airway 25 of the lung 30 in greater detail. The airway 25 is a bronchial tube, air passage, lumen, bronchial airway, or respiratory bronchiole of the lung 30. The airway 25 includes smooth muscle tissue that helically winds around the bronchiole to define a duct of the airway 25 through which air may be inhaled and exhaled during operation of the lung. The smooth muscle tissue is arranged around the airways in a generally helical pattern with pitch angles ranging from about −30 to about +30 degrees. As the airway 25 branches deeper into the lung, more and more alveolar sacs 26 and alveoli 28 appear, as shown in FIGS. 3 and 4.

Figure 5:
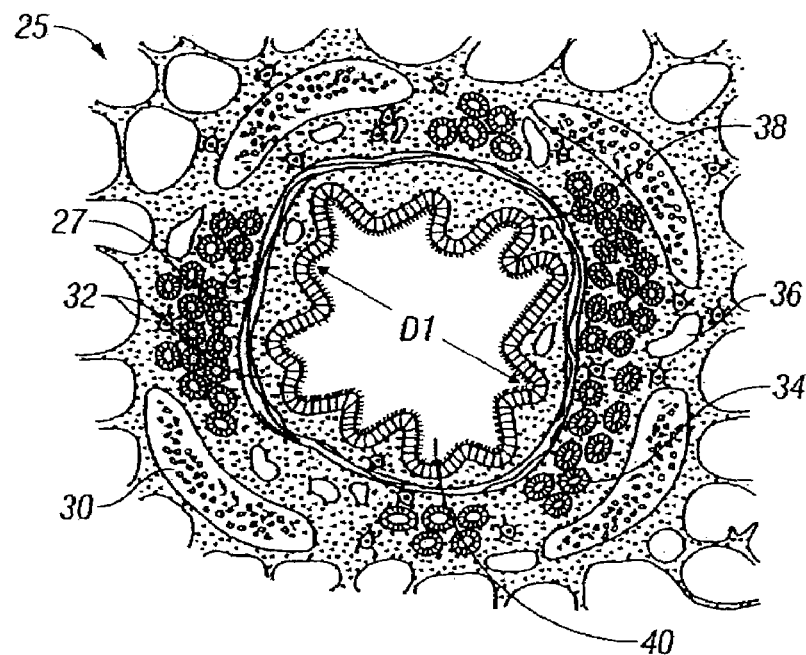
FIG. 5 is a cross-sectional view of the airway of FIG. 4 taken along the line 5-5 of FIG. 4.

FIG. 5 illustrates a light microscopic cross-section of the tissue of the airway 25, which is a collection of cells and intercellular substances that surround the cells, together defining the airway 25. The airway 25 defines an airway duct 40 through which gases are inhaled and exhaled. The airway 25 of FIG. 5 is a medium sized bronchus having an duct diameter DI of about 3 mm. The airway 25 includes a folded inner surface or epithelium 38 surrounded by stroma 32 and the smooth muscle tissue 27. The airway 25 also has mucous glands 34 and cartilage 30 surrounding the smooth muscle tissue. Nerve fibers and blood vessels 36 also surround the airway. Hence, as shown in FIG. 5, the smooth muscle tissue 27 is part of the overall tissue of the airway 25.

Referring again to FIG. 3, the diseased portion 31 of the lung 30 is located at the lower portion or base of the lung. By way of example, it can be considered that this diseased portion 31 has been stricken by emphysema. The emphysematous portion 31 of the lung 30 generally includes sections in which the walls between the adjacent alveoli 28 have deteriorated to a degree that the lung tissue looks like Swiss cheese in cross section. When this occurs, pulmonary function is impaired to a great degree.

The pulmonary system utilizes two simple mechanisms, air exchange into and out of the lungs 30 and gas exchange into and out of the blood. In patients with emphysema, both of these mechanisms are impaired, leading to dyspnea (shortness of breath), limitations in physical activities, and increased incidence of related diseases. To improve their condition, either or both of these impairments need to be improved. One way to address this is by restoring some of the lost air exchanging ability.

Air exchange is created by movement of muscles that increase and decrease the pressures around the lungs. Inspiration occurs when a decrease in pressure around the lungs to below atmospheric pressure expands the lungs, which in turn causes the pressure in the terminal end points of the airways (the alveoli 28) to drop below atmospheric. This pulls the air into the alveoli 28 through the conducting airways 25.

Exhalation is a passive process. Normal exhalation occurs when the muscles relax, allowing the natural elasticity of the lung structure to expel the air from within. In addition to making up the driving force to expel air from the lungs, the elasticity also mechanically helps keep conducting airways from collapsing. It is the loss of elasticity of lung tissue that leads to the condition known as "dynamic airway collapse".

In more detail, airway obstruction in the emphysematous patient has two components, "small airways disease" and dynamic airway collapse of the mid-sized airways. Both contribute to the patient's inability to get adequate amounts of air to and from the alveoli 28, which are the gas exchanging membranes in the lungs. Small airways disease is primarily caused by mucous plugging and inflammation of the small (less than 2 mm in diameter) airways, whereas dynamic airway collapse of the mid-sized airways (3 mm-6 mm) is mechanical in nature.

The mechanics of mid-size airway "patency" are dictated by four forces being in balance with one another. If the balance of those forces shifts, airway collapse will occur. Specifically, these forces are: (1) air pressure inside the airway in question, (2) air pressure in the alveoli directly surrounding that airway, (3)"tethering" of the airway by the surrounding tissue (parenchyma) and (4) stiffness of the airway wall itself. It is inherent in the movement of gases within the lungs that the pressure in the alveoli 28 directly surrounding the airway 25 must be higher than that within the airway itself during exhalation. Otherwise, no air would move from the alveoli 28 to, and through, the airway 25 on its way out of the lung. Since this inherent pressure differential would collapse an airway 25 if that airway were made of a very flexible material, there must be some mechanical strength built into the airway system to oppose this collapse in healthy people. This strength comes from both the stiffness of the airway wall and the tethering action of the surrounding parenchyma.

In patients with emphysema, the number of parenchymal tethers touching each airway is reduced. This in turn reduces the tethering forces that maintain the airway open. With these tethering forces reduced, the only thing keeping the airway open is the stiffness of the airway wall. In an emphysematous lung, this is often not enough, and the airways collapse during exhalation. Embodiments of the present invention aim to increase the strength of the airway walls to keep the airway open, which will increase gas exchange.

By strengthening the airway walls of an emphysematous lung, the balance of forces during exhalation is shifted back toward keeping the airways open. In short, stiffening the airway wall helps prevent airway collapse during exhalation, which will thus result in an increase in airflow and gas exchange.

One way to achieve this stiffening is to thicken the walls themselves. The present invention is based in part on the discovery that the airway 25 is strengthened because of the natural formation of fibrotic tissue, such as scar tissue, in response to trauma or injury. Fibrosis is the formation of fibrous or fibrotic tissue as a reparative or reactive process, i.e., regrowth of tissue after injury. The formation of fibrotic tissue essentially deposits additional tissue to the airway, which strengthens the wall of the airway. This stimulation of additional material will increase the thickness of the airway wall, thus strengthening the airway to help prevent the airway from collapsing during exhalation. The airway 25 is stiffened because the fibrotic tissue is thicker than the previous diseased tissue supporting the airway. As described below, the trauma can be caused by damaging the airway tissue, such as by delivering heat to the airway and/or by mechanical insult to the airway tissue.

By strengthening the airway walls of an emphysematous lung in accordance with the embodiments of the present invention, the balance of forces during exhalation is shifted back toward keeping the airways open. Stiffening airway wall by stimulating the deposition of fibrotic tissue helps prevent airway collapse during exhalation, and will thus result in an increase in airflow. In general, the greater the scarring or injury, the greater the build-up of fibrotic tissue. The thicker the airway wall due to build-up of fibrotic tissue, the less likely that it will collapse as it may have prior to treatment according to the present invention.

If the airway tissue is injured to such an extent that the airway wall thickens, it is preferable not to create so much fibrotic tissue that the airway closes. That is, it is preferable that the formation of fibrotic tissue does not cause stenosis. Stenosis may be prevented by controlling the extent of injury or damage to the airways of the lung. It is also preferable not to ablate or vaporize large amounts of airway tissue such that the airway loses its structure. Hence, it is preferable to damage enough airway tissue to cause fibrotic tissue to develop and stiffen the existing airway wall, rather than completely destroying the existing airway wall to define a new cavity, and rather than destroying so much tissue that a mass of scar tissue blocks the airway.

The gas exchange of the lung 30 can also be increased in accordance with the embodiments of the present invention by destroying the airway smooth muscle tone. Smooth muscle tone refers to ability of the smooth muscle of the airway to respond to signals that trigger the airway smooth muscle to continually and partially contract. By destroying the smooth muscle or disrupting the smooth muscle's ability to respond to such signals, the contraction force is removed and the airway will become larger.

When one inhales, the pressure in the airway is higher than the alviolar pressure that acts on the outside of the airway. This being the case, a "floppy" or diseased airway will remain open on inspiration. However, as described above, upon expiration, the alviolar pressure builds and at some point exceeds the air pressure in the airway. In this state, a floppy airway will be more prone to collapse and inhibit the flow of air out of the alveoli. The smooth muscle tone may further restrict the airway diameter. Hence, the removal or destruction of at least some of the smooth muscle tone will beneficially increase gas exchange during the expiration cycle.

Thus, the present invention strives to relieve the effects of emphysema and other forms of pulmonary disease by increasing the efficiency of gas exchange in the lung 30. Generally speaking, this may be achieved by inserting an apparatus into an airway of the lung through the trachea 22, and then damaging tissue of the airway 25 to cause fibrosis to strengthen the airway and/or to destroy smooth muscle tone of the airway.

The following description of the treatment apparatus for use with the embodiments of the present invention can be employed to treat a bronchial tube regardless of whether the tube lumen has collapsed or not. Specifically, the devices can be used to treat bronchial tubes that have not collapsed, are partially collapsed, or are fully collapsed. Moreover, bronchial tubes may exhibit different degrees of closure depending on the state of respiration. For example, a bronchial tube may have a fully expanded lumen during inhalation but partially or completely closed during exhalation.

Figure 6:
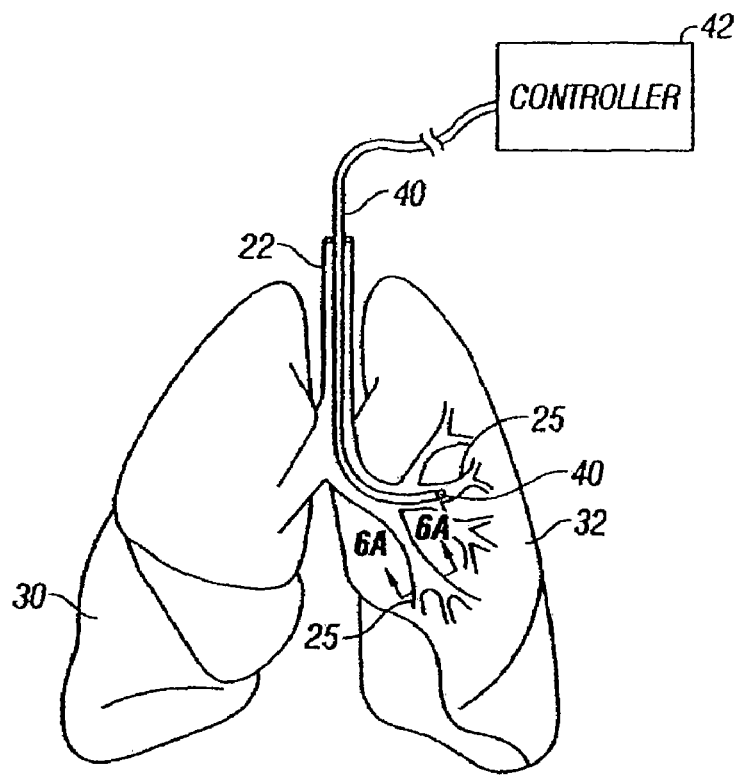
FIG. 6 is a schematic side view of lungs being treated with the treatment apparatus in accordance with one embodiment of the present invention.

FIG. 6 is a schematic view of the lung 32 being treated with a treatment apparatus 40 in accordance with a method of the present invention. The preferred apparatus 40 is an elongated member that may be electronically or manually controlled by a surgeon or controller 42 to damage lung cells to cause fibrosis to stiffen the airway and/or to destroy smooth muscle tone of the airway so as to increase gas exchange performed by the lung. As described further below, the damaging of cells of airway tissue and/or destruction of smooth muscle tone of the airway with the apparatus 40 may be accomplished by any one of, or combinations of, the following:

(1) heating the tissue;
(2) cooling the tissue;
(3) delivering a liquid that damages the tissue;
(4) delivering a gas that damages the tissue;
(5) puncturing the tissue;
(6) tearing the tissue;
(7) cutting the tissue;
(8) applying ultrasound to the tissue;
(9) applying ionizing radiation to the tissue;
(10) other methods that cause trauma to lung cells to cause fibrosis to stiffen the airway so as to increase gas exchange performed by the lung; and
(11) other methods that destroy smooth muscle tone of the airway so as to increase gas exchange performed by the lung. A more detailed description of the methods of stiffening the airway 25 and destroying the airway smooth muscle tone to increase gas exchange follows.

FIG. 6A is a representational cross-sectional view of the airway 25 of the lung 32 during expiration before it has been treated with the apparatus 40, while FIG. 6B is a representational cross-sectional view of the airway 25 during expiration after it has been treated with the apparatus 40 in accordance with a preferred method of the present invention FIG. 6B.

As illustrated in FIG. 6A, the airway 25 is partially collapsed due to pulmonary disease, such as described earlier. In this state, air exchange is adversely affected. In FIG. 6B, the treatment apparatus 40 has damaged the tissue of the airway 25 so as increase the thickness of the airway wall. More particularly, the airway 25 has been strengthened because of the natural formation of fibrotic tissue in response to trauma or injury. The formation of the fibrotic tissue has deposited additional tissue to the airway, which strengthens the wall of the airway. Thus, the airway wall shown in FIG. 6B is thicker than the airway wall shown in FIG. 6A. This increased thickness of the airway wall strengthens the airway to help prevent the airway from collapsing during exhalation. Accordingly, the airway illustrated in FIG. 6B is not collapsed to the same extent as the untreated airway illustrated in FIG. 6B. Hence, if the lung 32 is stricken with emphysema, the previously described balance of forces during exhalation is shifted back toward keeping the airway 25 open, which helps prevent airway collapse during exhalation, and will thus result in an increased airflow and gas exchange.

Figure 70:
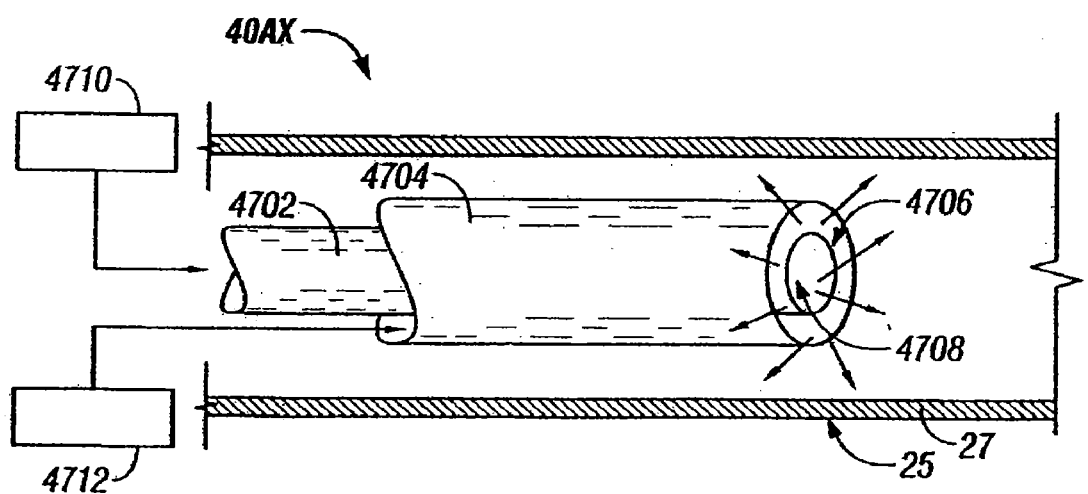

FIGS. 7-70 illustrate embodiments of treatment apparatus or devices 40A-40AX that can be used to destroy airway smooth muscle tone and/or damage airway tissue to induce fibrosis according to the present invention. These are just some of the examples of the type of treatment apparatus which may be used to perform the methods according to the present invention. It should be recognized that each of the treatment apparatus described below can be modified to deliver or remove energy in different patterns, depending on the treatment to be performed. The treatment apparatus may be actuated continuously for a predetermined period while stationary, may be pulsed, may be actuated multiple times as they are moved along an airway, may be operated continuously while moving the treatment apparatus in an airway to achieve a "painting" of the airway, or may be actuated in a combination of any of these techniques. The particular energy application pattern desired can be achieved by configuring the treatment apparatus itself or by moving the treatment apparatus to different desired treatment locations in the airway.

FIG. 7 is a schematic side view of lungs being treated with a treatment apparatus 40A in accordance with one embodiment of the present invention. The treatment apparatus 40A is an elongated member for delivery of energy from an energy source 50 to a treatment site 52 at an airway of the lungs. The energy may be delivered by the treatment apparatus 40A in a variety of treatment patterns to achieve a desired response. Examples of patterns are discussed in further detail below. The energy which is delivered by the treatment apparatus 40A may be any of a variety of types of energy including, but not limited to, radiant, laser, radio frequency, microwave, heat energy, or mechanical energy (such as in the form of cutting or mechanical dilation). In addition, the delivery of laser or light energy may be in conjunction with the delivery of a photodynamic agent, where the laser or light energy stimulates the photodynamic agent and initiates a cytotoxic, or cell damaging chemical reaction.

The airway smooth muscle tone can be destroyed and the cells of the airway tissue of the airway 25 can be damaged by exposing the tissue 27 to energy. The damaging of the airway tissue by energy will induce fibrosis so as to strengthen the airway. A pattern for treatment can be chosen from a variety of patterns including longitudinal stripes, circumferential bands, helical stripes, and the like as well as spot patterns having rectangular, elliptical, circular or other shapes. The size, number, and spacing of the treatment bands, stripes, or spots are chosen to provide a desired clinical effect of strengthening the airway wall or destroying the smooth muscle tone of the airway without completely destroying the airway or obstructing the airway.

Figure 8:
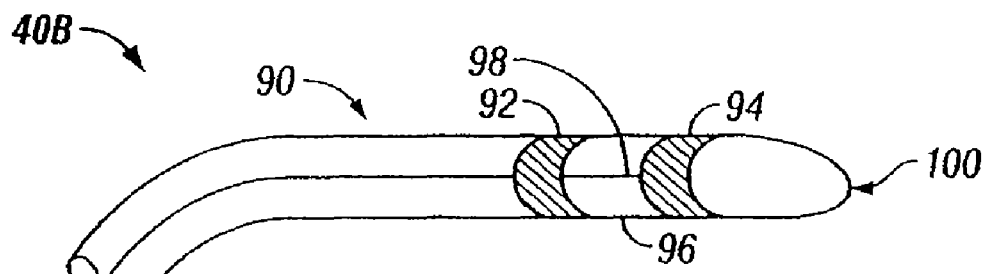
FIGS. 8, 9, 10A, 10B, 11A and 11B are perspective views of heat treatment apparatus for use with the methods of the present invention.

FIG. 8 illustrates another treatment apparatus 40B for use with one embodiment of the present invention. The treatment apparatus 40B includes an elongated, cylindrical member 90 having a heating element that has a plurality of electrodes designated 92 and 94 located on the outer surface of the member. The electrodes are electrically connected to a source of RF energy via connector 98. Preferably each electrode is configured as a band as shown that has a width of about 0.2 mm to about 3 mm, and preferably each electrode band is separate from the next by a distance of about 0.5 mm to 10 mm. The heating element may include one or more electrode bands. The treatment apparatus 40B has a distal end 100 that is rounded to reduce the amount of resistance encountered when the apparatus is advanced into the airway 25.

The apparatus 40B has an outer diameter that is approximately equal to (or can be expandable to equal) the desired final inner diameter of the lumen of an air passage to be treated. Typically, the outer diameter ranges from about 1.3 mm to about 7 mm. When the heating element comprises a plurality of electrode bands, the distance between each band is preferably less than about three times the outer diameter of the apparatus. The effect will be that the patency bands formed on the wall of the lumen by the electrodes 92, 94 will be separated from each other by no more than a distance equal to about three times the length of the outer diameter of the lumen. The patency bands so configured will provide good support for the airway 25 to prevent the lumen from collapsing.

The treatment apparatus 40B applies a sufficient amount of energy to the walls of collapsible air passages 25 to destroy airway smooth muscle tone and damage cells of the airway tissue to induce fibrosis and create a more rigid wall that can support a non-collapsed lumen. In this embodiment, energy emanates from the electrode bands 92, 94, so that following treatment with this particular apparatus, the walls of the air passage 25 will develop patency bands corresponding to locations along the walls. The contours of the patency bands should substantially match those of the electrode bands. As is apparent, the number and width of each electrode band are not critical. In the case where there is only one electrode band, it may be necessary to move the apparatus and heat more than one area of the lumen wall in order to damage sufficient amounts of the airway wall to induce enough fibrosis to increase the strength of the airway wall such that it is no longer collapsed, i.e., the lumen remains substantially open during normal breathing.

When the treatment apparatus 40B is positioned at the treatment site, an RF generator is activated to provide suitable RF energy, preferably at a selected frequency in the range of 10 MHZ to 1000 MHZ. The emitted energy is converted within the tissue into heat in the range of about 40° C. to about 95° C.

RF energy is no longer applied after there has been damage to the tissue to induce a healing response. Preferably, the RF energy is applied for a length of time in the range of about 1 seconds to about 120 seconds. Suitable RF power sources are commercially available and well known to those skilled in the art. In one embodiment the RF generator employed has a single channel, delivering approximately 1 to 25 watts of RF energy and possessing continuous flow capability. The rate of transformation can be controlled by varying the energy delivered to the heating element.

Besides using RF energy for energizing the heating element, it is to be understood that other forms of energy such as alternating current, microwaves, ultrasound, and light (either coherent (e.g., laser) or incoherent (e.g., light emitting diode or tungsten filament) can be used), and that the thermal energy generated from a resistive coil, a hot fluid element (e.g., circulating liquids, gases, combinations of liquids and gases, etc.), a curie point element, or similar elements can be used as well. The hot fluid element may comprise, for example, an elongated member similar to the one illustrated in FIG. 8 that includes a conduit system whereby heated fluid is transported through the center of the member and then channeled outward toward the inner surface of the member. In one embodiment the heated fluid is diverted to contact the inner surface of the elongated member so that energy radiates from selected areas on the outer surface of the member corresponding to areas 92 and 94 in FIG. 8. Regardless of the source, energy delivered to the lumen wall of the obstructed airway passage should be such that all of the airway tissue is not completely ablated.

The heating element, as shown in FIG. 8, operates as a unipolar, internal electrode in the patient's body. An outer electrode (not shown) having a much larger surface area than that of the electrode bands is placed on the outer surface of the patient's body. For example, an external metal mesh or solid plate is placed on the skin with conductive gel. Both electrodes are connected to an RF generator which produces an electric field at a high frequency within the patient's body. Because the collective surface area of the electrode bands is much smaller than that of the outer electrode, the density of the high frequency electric field is much higher around the electrode bands. The electric field reaches its highest density between the two electrodes in the region near the heating element. The increased density of the field around the electrode bands produces localized heating of the tissue of the lumen wall.

A heating element comprising a bipolar electrode can also be used. Referring to FIG. 8, in a bipolar arrangement electrode band 92 would be a first conductive element and electrode band 94 would be a second conductive element.

Figure 9:
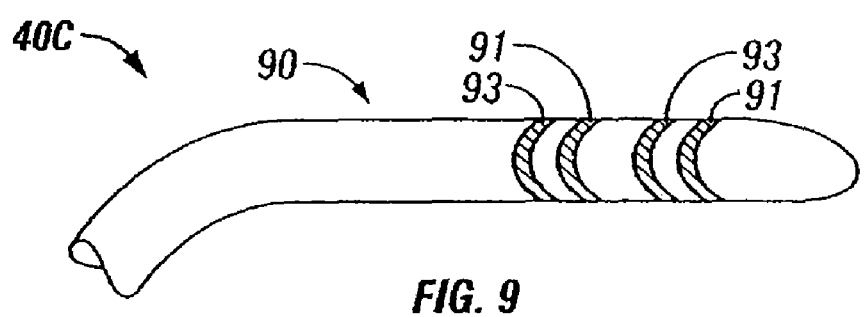

The electrode bands emit RF energy with the first conductive element acting as the active electrode and the second conductive element acting as the return electrode, or vice versa. One electrode would be connected to the positive electrode of the generator and the other would be connected to the negative electrode. An insulator 96 is located between the conductive elements. FIG. 9 illustrates another treatment apparatus 40C for use with another embodiment of the present invention. The treatment apparatus 40C includes a heating element having multiple, i.e., double, bipolar electrode bands. Bands 91 are connected to the positive electrode of the RF generator and bands 93 are connected to the negative electrode. The material between the conductive elements are electrically insulated.

While the heating elements have been shown as electrode bands, other configurations can be used such as, for example, spiral, ring and grid patterns. These elements will create corresponding patterns on the lumen wall.

Figure 10A:
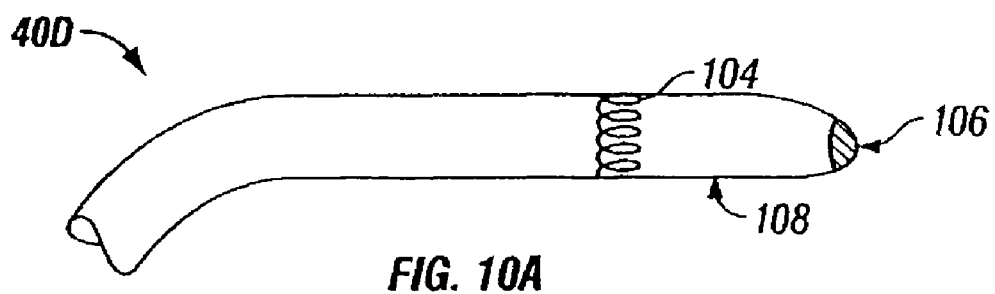

FIG. 10A illustrates another embodiment of the treatment apparatus 40D for use with another embodiment of the present invention. The treatment apparatus 40D includes an elongated, cylindrical member having a heating element that comprises electrodes 106 and 104 located on the other surface of the member. Preferably, the heating element comprises a bipolar electrode wherein one of the electrodes is the active electrode and the other electrode is the return electrode, or vice-versa. One electrode is connected to the RF positive electrode of the generator and the other is connected to the negative electrode. Segment 108 of the member situated between the electrodes is made of electrically insulating material.

Figure 10B:
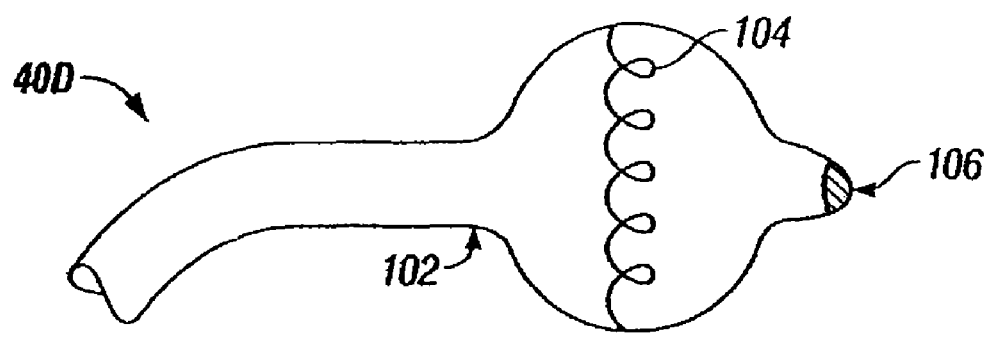
Figure 11A:
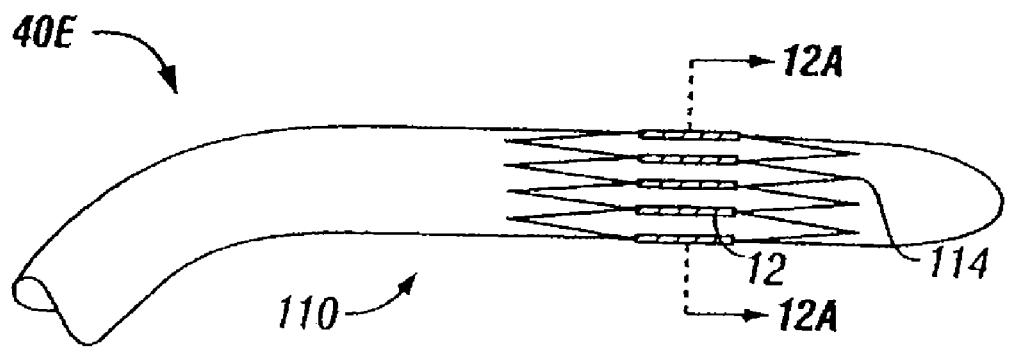
Figure 11B:
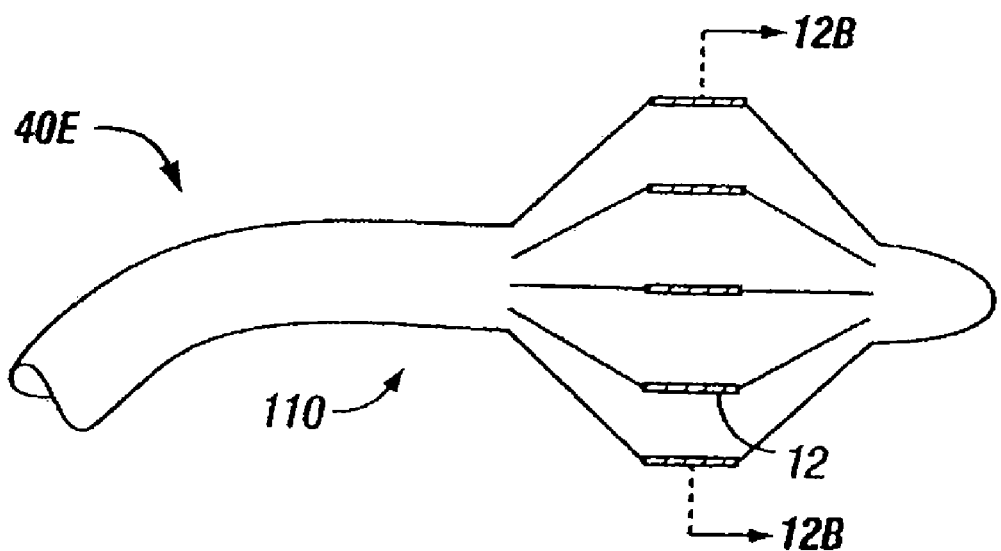

The segment of elongated member in and around electrode 104 is fabricated of material that is expandable and substantially impervious to air or other suitable gases for causing the elongated member to balloon. In this fashion, this section of the elongated member is radially expandable and deformable in response to compressed gas or any other suitable force or material that is applied into the interior region of the elongated member. Moreover, the elongated member will substantially return to its original, non-expanded form when the internal force is deactivated or the material is withdrawn. FIG. 10B illustrates the elongated member in the expanded position. The degree of expansion or distance that the member expands will depend on, among other things, the pressure applied and the elasticity of the member wall. In this embodiment, material between position 102 on the elongated member to the base of electrode 106 is fabricated from expandable material such as latex or polyethylene. The material selected preferably does not melt at the temperature ranges used in the treatment. Radial expansion causes electrode 104 to come into thermal or electrical contact with tissue of the air passage 25 to be treated. Electrode 104 is preferably a spring coil. The treatment apparatus 40D may comprise more than one such coil electrode, which may be positioned along the length of the elongated member so that a plurality of locations along a bronchial tube can be treated simultaneously.

Figure 12A:
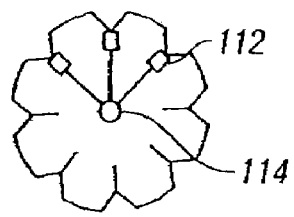
FIGS. 12A and 12B are cross-sectional views of heat treatment apparatus for use with the methods of the present invention.
Figure 12B:
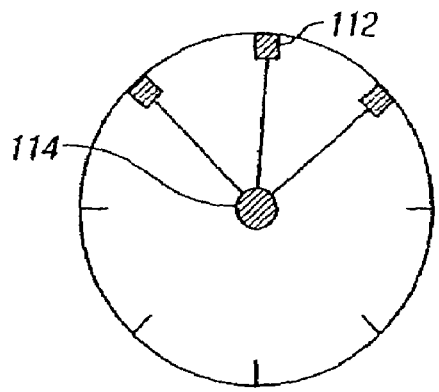

FIGS. 11A, 11B, 12A and 12B illustrate a further embodiment of the treatment apparatus 40E for use with an embodiment of the present invention. The treatment apparatus 40E includes an elongated, cylindrical member 110 having one or more electrodes 112 situated on the outer surface of the elongated member. Preferably, a plurality of these electrodes form a number of rows of electrodes that are positioned along the length of the elongated member. As shown in cross sectional view FIG. 12A, the segment of surface of the elongated member at and around the electrodes is arranged in pleats 114. By being folded in this manner, the surface can expand radially when an outward force is applied from the interior of the cylindrical member as shown in FIGS. 12A and 12B. In this embodiment, the electrodes comprise non-ferrous (e.g., aluminum) strips and an electromagnet 114 which is positioned in the interior of the elongated member. When the electromagnet is energized with alternating current the magnetic field will cause the non-ferrous electrodes to repel from the electromagnet. In addition, the temperature of the electrode will rise due to Joule heating. The treatment apparatus may comprise a plurality of rows of the electrodes.

Figure 13A:
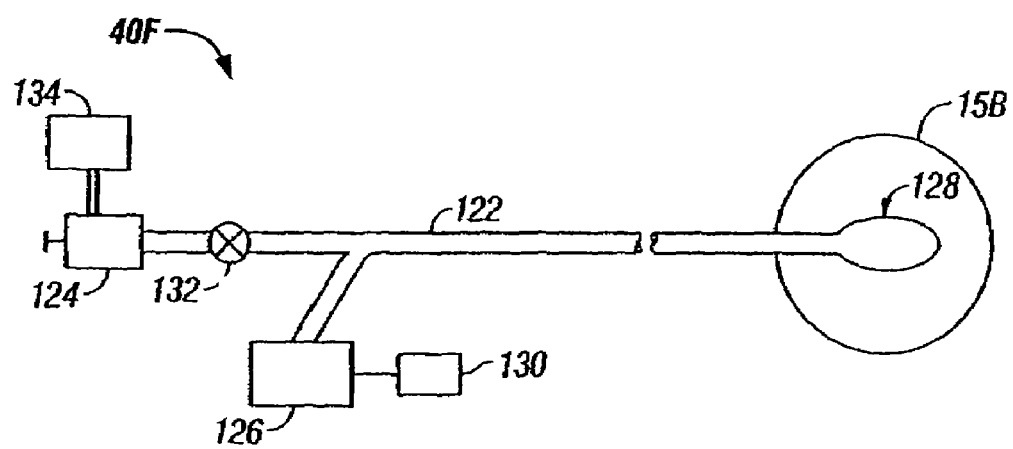
FIG. 13A is a schematic view of an embodiment of the treatment apparatus for use with the methods of the present invention.
Figure 13B:
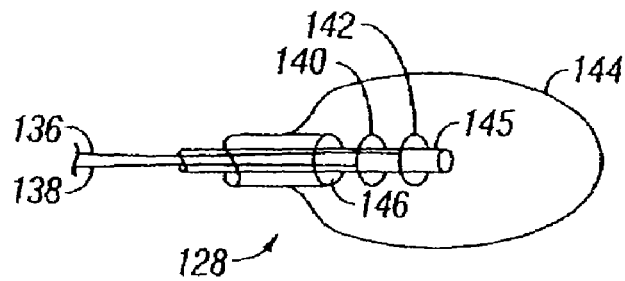
FIG. 13B is an enlarged view of the circled portion of FIG. 13A.

FIG. 13A illustrates another embodiment of a treatment apparatus 40F for use with another embodiment of the present invention. The treatment apparatus 40F includes a balloon 128 placed at the distal end of a catheter shaft 122. The catheter shaft is connected to syringe 124 located at the proximal end and is connected to an RF generator 126 in between the syringe and balloon. As shown in FIG. 13B which is an enlarged, cut away view of the device, the balloon 128, which is illustrated in the non-inflated state, is constructed of an elastomeric material 144. A preferred elastomeric material is silicone. Extending from lumen 146 of the shaft and into the interior of the balloon are electrodes 140 and 142 which are spaced apart and supported by rod 145. In this embodiment, each electrode is configured as a loop or ring around the rod. Catheter shafts suitable for use in the present invention are substantially any of the catheter shafts in current clinical use for surgical procedures. Balloons suitable for the present invention may be of similar material and design as those currently being used in percutaneous transluminal angioplasty. For a review of the state of the art, see U.S. Pat. Nos. 4,807,620; 5,057,106; 5,190,517; 5,281,218; 5,314,466; 5,370,677; 5,370,678; 5,405,346; 5,431,649; 5,437,664; 5,447,529; and 5,454,809, the disclosures of which are all incorporated herein by reference. The inventive heat treatment apparatus will be described using balloons that are fabricated from an elastomeric material such as, for instance, silicone, natural latex, and polyethylene. The material selected preferably does not melt at the temperature ranges used in the treatment and is preferably impervious to the fluid used to inflate the balloon. With balloons that are made of elastomeric materials, the degree of expansion is proportional to the amount of force introduced into the interior of the balloon. Moreover, the balloon preferably will substantially return to its original, non-expanded form when the internal force is deactivated. When the balloon is fully expanded, its diameter will preferably be about 1 mm to 30 mm depending on the site to be treated. The balloon is typically attached to the catheter tip and the balloon material is folded or collapsed so that when it is fully inflated the balloon diameter has a fixed dimension. It is understood however that other balloon structures can be employed. For example, balloons made of non-elastic materials such as, for example, polyester (e.g., MYLAR) and polyethylene, can also be used. As is apparent, the balloon serves as a vessel or reservoir for medium that is heated. In the case where the electrodes are bipolar electrodes, the fluid (e.g., saline) between the poles acts as a resistive heating medium or resistive element. In addition, the balloon upon being inflated serves as structural support for the bronchial tubes.

Referring to FIGS. 13A and 13B, electrodes 140 and 142 are connected via cables 136 and 138, through the wall of the balloon 128, and through the catheter shaft 122 to a radio frequency (RF) generator 126 with controls 130. The catheter shaft 122 is also connected to the syringe 124 or other similar device for forcing a non-compressible fluid, such as saline, from source 134 through valve 132 to inflate the balloon with the fluid as the operating surgeon deems appropriate.

The frequency range of RF radiation useful in the present invention is typically about 10 KHZ to about 100 MHZ and preferably in the range of about 10 KHZ to about 800 KHZ. However, frequencies outside this range may be used at the discretion of the operating surgeon. Alternatively, microwave radiation typically in the frequency range of about 1,000

MHZ to about 2,000 MHZ, preferably in the range of about 1,100 MHZ to about 1,500 MHZ, may be used in place of RF radiation. However, as above, frequencies outside this range may be used at the discretion of the operating surgeon. The RF generator 126 may be replaced with a microwave generator, and the cables 136 and 138 replaced with a waveguide. Other modifications familiar to those skilled in the art may also be required. In addition, alternating current can be employed.

In use, when the operating surgeon has placed the treatment apparatus with the collapsed balloon within the lumen of a bronchial tube to be treated, the balloon is inflated through the catheter shaft 122 with fluid from the syringe 124 located conveniently for the surgeon. In the case where the lumen of the bronchial tube has collapsed or is partially collapsed, the balloon is preferably inflated until the lumen has expanded to its normal diameter with the balloon in substantial contact with the inner surface of the lumen. Alternatively, in the case where the lumen has not collapsed, the balloon is preferably inflated until it is in substantial contact with the inner surface of the lumen. Indeed, inflation of the balloon is not necessary in treating a non-collapsed bronchial lumen which has a diameter that is about equal to, or less than that of the outer surface of the uninflated balloon. As is apparent, even if the balloon does not have to be inflated, the balloon interior has fluid, e.g., electrically conductive saline, present which becomes heated by the application of RF energy.

Preferably, the exact amount of inflation is determined by the operating surgeon who monitors the balloon expansion by means of endoscopy, or other suitable imaging methods of the art. Generally, the heat required is induced in the tissue of the bronchial tube wall by the RF or microwave radiation emitting from the balloon tip.

FIGS. 14A, 14B, 15A, 15B, 16A, 16B, 17A, and 17B illustrate other embodiments of the electrode configurations which can be employed with the treatment apparatus 40F shown in FIG. 13A. In these figures, the balloons are shown in the inflated state containing fluid 151. The arrows depict the path of the electric field between the two electrodes or probes that serve as RF poles in the manners described above.

Figure 14A:
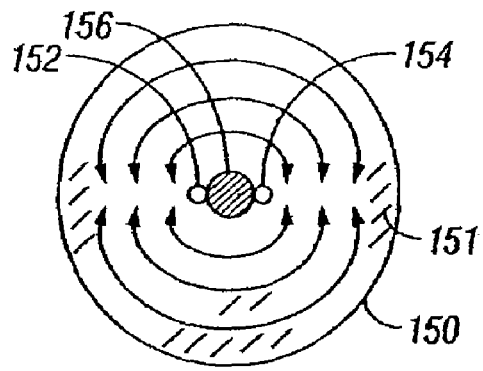
FIGS. 14A, 14B, 15A, 15B, 16A, 16B, 17A, and 17B illustrate additional embodiments of the heat treatment apparatus which employ RF energy for use with the methods of the present invention.
Figure 14B:
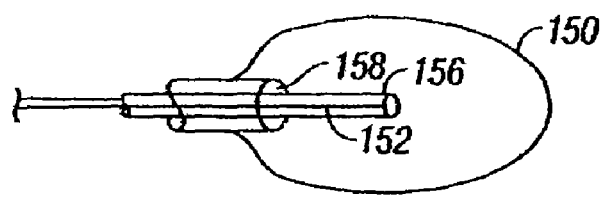

In FIG. 14A, which is a cross-sectional view of balloon 150, electrodes 152 and 154 are configured as elongated wires that are attached at opposite sides of nonconductive rod 156. FIG. 14B is a side view of the balloon with the electrodes inside the interior of the balloon which is sealed except for conduit 158 through which fluid 151 (e.g., saline) is introduced and removed.

Figure 15A:
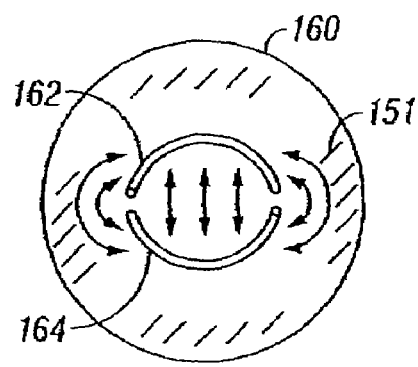
Figure 15B:
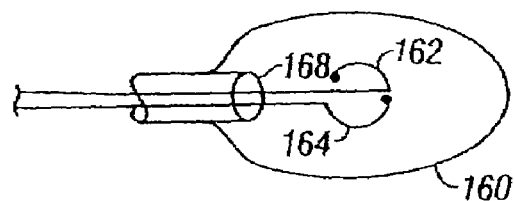

In FIG. 15A, which is a cross-sectional view of the balloon 160, electrodes 162 and 164 are wires each configured as a semi-circle and positioned at opposite sides of each other to form a circle. The electrodes have opposite polarities and are electrically insulated from each other. FIG. 15B is a side view of the balloon with the electrodes inside the interior of the balloon which is sealed except for conduit 168 through which fluid 151 is introduced and removed.

Figure 16A:
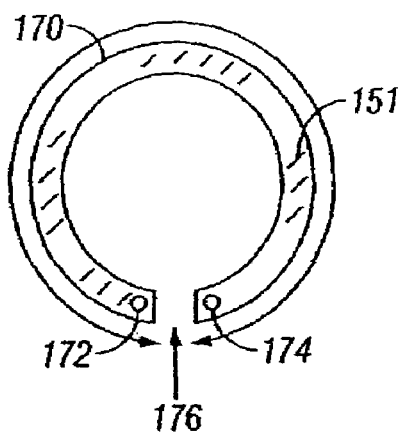
Figure 16B:
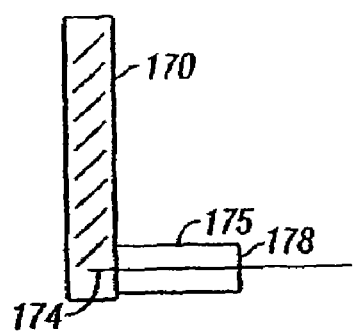

In FIG. 16A, which is cross-sectional view of the balloon 170, electrodes 172 and 174 are wires with tips that protrude into the interior region of the balloon which has a hollow disk or horse shoe configuration with partition 176 separating the two halves of the disk. Fluid 151 is introduced and removed from the balloon through conduit 178 in support member 175. The electrodes remain stationary in the solid regions of support member 175 as shown in side view FIG. 16B.

Figure 17A:
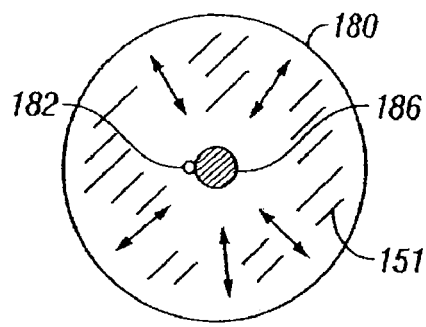
Figure 17B:
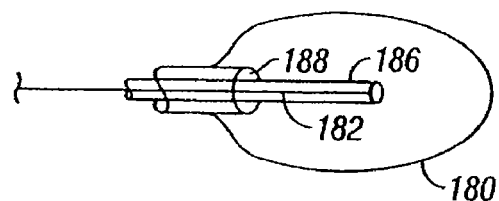

FIGS. 17A and 17B illustrate another embodiment in which the balloon 180 is fabricated of an electrically conductive material and therefore also serves as an electrode. In this fashion, one of the electrodes is an integral part of the balloon itself. The second electrode 182 is attached to non-conducting rod 186. FIG. 17B is a perspective view of the balloon with electrode 182 in the interior of the balloon which is sealed except for conduit 188 through which fluid 151 is introduced and removed. Suitable electrically conductive materials for fabricating the balloon in this case include, for example, a polyester film (e.g. MYLAR) that is coated with gold, silver, or platinum.

Figure 18:
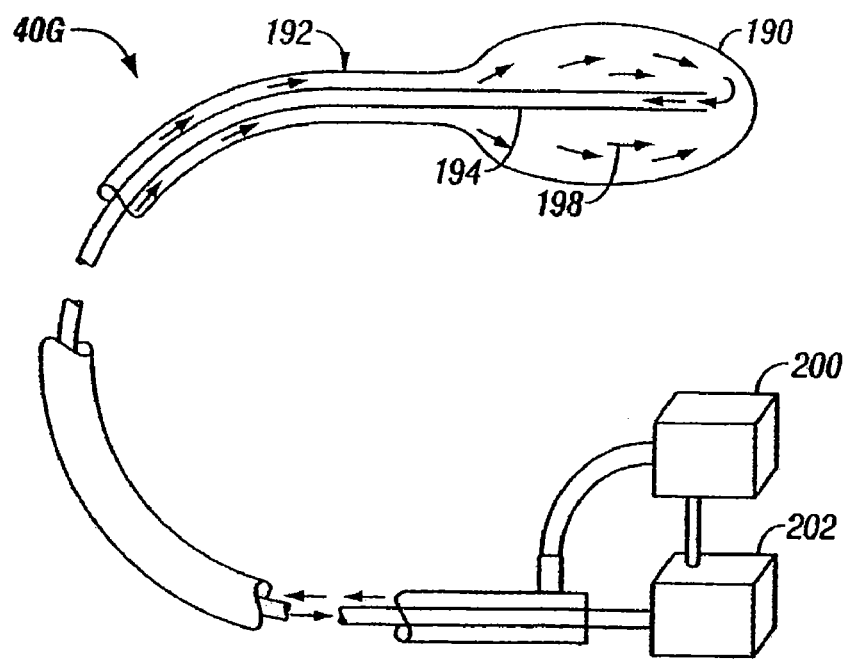
FIG. 18 illustrates an embodiment of the heat treatment apparatus which employs circulating heated fluid for use with the methods of the present invention.

FIG. 18 illustrates another embodiment of the treatment apparatus 40G for use with one embodiment of the present invention. With the treatment apparatus 40G, the heat generated to heat the fluid in the balloon is supplied by a circulating, hot fluid. Referring to FIG. 18, a balloon 190 (substantially the same as balloon 128 of the embodiment shown in FIG. 13A) is attached to a catheter 192 containing a smaller, coaxial catheter 194 (coaxial catheter 194 is substantially the same as catheter 192, differing only in size.) A heated fluid 198, which may be a liquid, such as water or physiologically compatibly saline solution, is pumped by a metering, circulating pump 202, through a heating unit 200, then through the outer catheter 192 to the balloon. The fluid heats the surface of the balloon and exits through the inner coaxial catheter 194 to return to the pump. A positive pressure is maintained within the system to keep the balloon at the proper inflation. This embodiment is employed in substantially the same manner as the other embodiments described above regarding its use to heat the airway tissue to induce fibrosis and strengthen the airway and destroy smooth muscle tone. The choice of the temperature of the circulating liquid is at the discretion of the operating surgeon, but will usually be in the range of about 60° C. to about 95° C.

Figure 19:
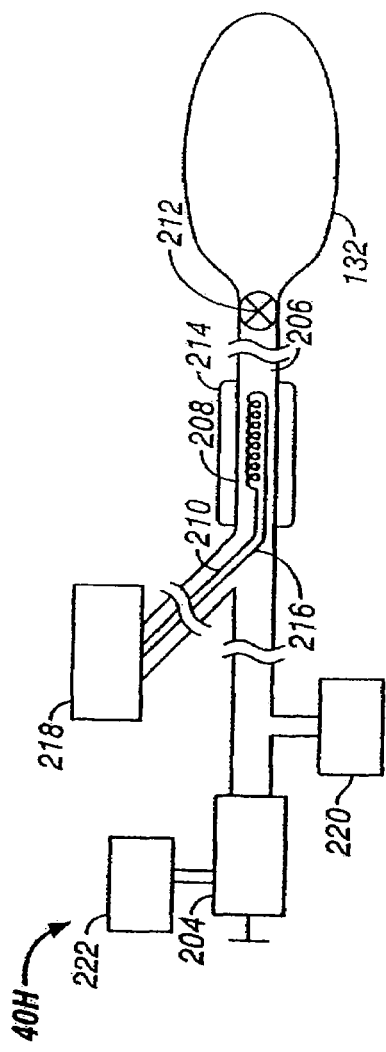
FIG. 19 illustrates an embodiment of the heat treatment apparatus that has both resistive heating and inductive heating for use with the methods of the present invention.

The treatment apparatus 40H shown in FIG. 19 represents another embodiment of the treatment apparatus for performing another embodiment of the present invention, wherein the heat generated to heat the fluid in the balloon is supplied by a hot fluid that is injected into the balloon. The catheter 208 includes electrodes 210 and 216 positioned in lumen 206 of the catheter. The electrodes are connected to AC generator 218 although an RF generator can also be used. The channel or lumen 206 also serves as a reservoir for liquid which is introduced from source 222 through syringe 204. Once the fluid is heated to the desired temperature, it can be injected into the interior of the balloon. As is apparent, the fluid serves both to inflate the balloon as well as to supply the heat treatment of the bronchial tube. A positive pressure is maintained within the system to keep the balloon at the proper inflation. Instead of using resistive heating, the fluid can be heated with heat exchanger 208.

Preferably, the RF energy is applied for a length of time in the range of about 1 second to about 600 seconds and preferably about 5 to about 120 seconds. Suitable RF power sources are commercially available and well known to those skilled in the art. In one embodiment the RF generator employed has a single channel that is capable of delivering approximately 1 to 100 watts and preferably 1 to 25 watts of RF energy and possesses continuous flow capability. Regardless of the source of energy used during treatment, the lumen or the bronchial tube is maintained at a temperature of at least about 60° C. and typically between 70° C. to 95° C. and preferably between 70° C. to 85° C.

Figure 13C:
FIG. 13C illustrates another embodiment of a treatment apparatus for use with the methods of the present invention.

The treatment apparatus of the present invention may include more than one balloon and attendant bipolar electrodes which are positioned along the length of the elongated member so that a plurality of locations along a bronchial tube can be treated simultaneously. FIG. 13C illustrates an alternative embodiment of the treatment apparatus of FIG. 13A described above, which includes two balloons 148A, 148B that are spaced apart. Each balloon 148A, 148B includes a suitable set of bipolar electrodes as described previously. The balloons can be connected to separate sources of fluid or they can share a common source.

Figure 20A:
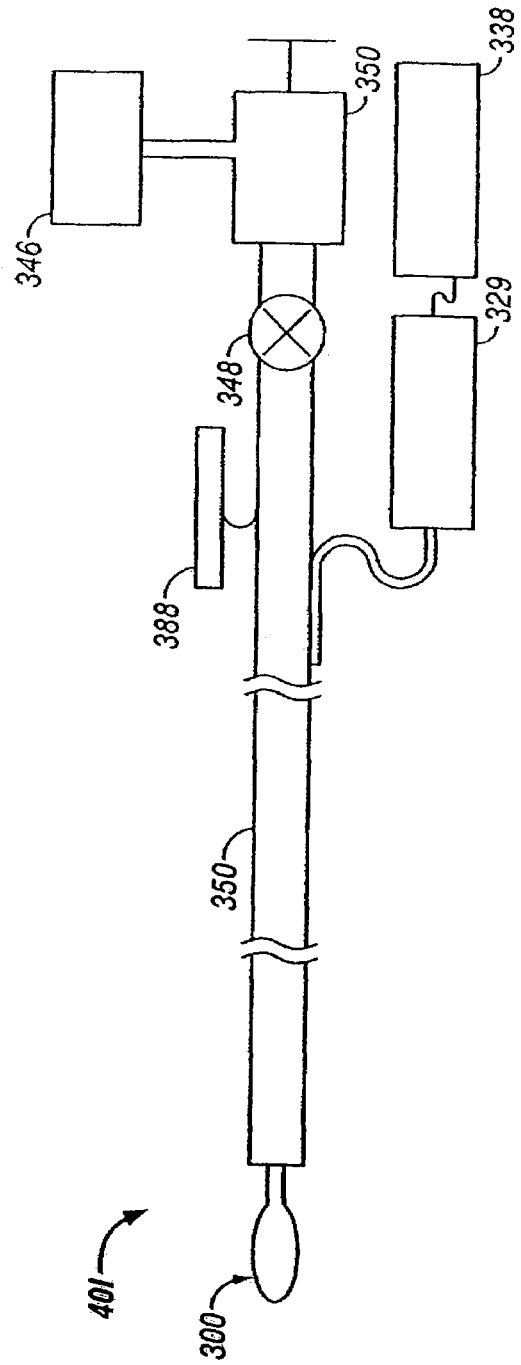

FIGS. 20A and 20B show a further embodiment of the treatment apparatus 40I for use with another embodiment of the present invention. The treatment apparatus 40I includes a balloon 300, similar to the balloons described earlier, that is positioned at or near the distal end of elongated rod 310 which is positioned within the lumen or aperture 351 of catheter sheath 350. It is understood that the term "rod" also encompasses tubes which have hollow channels. As shown, the balloon with inner surface 301 is in the inflated state having been inflated with an appropriate fluid such as air or saline that is injected from conduit 330 and into the interior of the balloon through aperture 331 in the rod. The apparatus includes electrodes 302 and 304, similar to those described earlier, which are spaced apart along the outer perimeter of the inflated balloon. It is understood that the number of electrodes and their configurations on the outer surface of the balloon can be varied. These electrodes come into contact with the wall of the airway 25 when the balloon is inflated. The electrodes employed in the present invention can have different configurations. For example, the electrodes can be conventional coil wires with round cross sections, or they can have a non-round configuration, such as, for example, a thin, foil or band with a rectangular cross section. For the device shown in FIG. 20B, electrodes 302 and 304 are preferably flat bands each extending around the circumference of the balloon. To permit expansion of the balloon, each band is positioned around the outer surface of the balloon with the two ends overlapping each other. As shown the FIG. 20B, electrode 302 is a band having ends 303 and 313 with a portion of the band adjacent to end 303 overlapping a portion of the band adjacent to end 313. Similarly, electrode 304 is a band having overlapping ends 305 and 315.

The balloon of the treatment apparatus 40I is preferably constructed of non-elastic material that is initially folded and/or collapsed. In this non-inflated state, the diameter of the balloon is small enough that the balloon can be positioned inside an aperture or working channel of a bronchoscope. In use, the bronchoscope first is positioned at the treatment site before the balloon is exposed and then inflated. Heat treatment is then commenced to damage airway tissue to induce fibrosis and/or destroy smooth muscle tone.

FIGS. 20A and 20B show that electrodes 302 and 304 are connected via cables 322 and 342, respectively, to a radio frequency (RF) generator 329 with controls 338, such as described earlier. Rod 310 is also connected to syringe 350 which is employed to inject a fluid from source 346 through valve 348 into the balloon.

FIG. 21 illustrates another embodiment of the treatment apparatus 40J for use with another method of the present invention which includes a pair of electrode coils 410 and 420 that are positioned in tandem. The number of electrode coils is not critical. The apparatus also includes an elongated rod 430 which has a distal end 431 that is connected to a tip or knob 440 and has a proximal end which is at least partially slidably positioned inside aperture 451 of catheter sheath 450 that includes end coupler 435. Coil 410 has two ends, the first end 411 being attached to knob 440 and the second end 412 is attached to rotatable or floating coupler 470. Similarly, coil 420 has two ends, the first end 421 is attached to rotatable coupler 470 and the second end 422 is attached to end coupler 435.

As shown in FIG. 21, the coils are in the relaxed state which is meant that no torque is being applied to either coil. In this state, each coil has a "barrel" configuration so that the diameter of the outer contour formed by each coil is largest at its center and smallest at its two ends. A number of preferred methods can be employed to change the diameters of the contour. One method is to compress or expand the coils along the axis. For example, by pushing rod 430 outward so that knob 440 extends away from catheter sheath 450, the coil diameters will decrease. Another method of changing the diameter is to apply torque to the coils. Torque can be applied by rotating the rod in a clockwise or counterclockwise direction while keeping end coupler 435 stationary, e.g., attached to the inner surface of catheter sheath. Torque can also be applied by keeping rod 430 stationary while rotating end coupler 435. Alternatively, torque can be applied by rotating the rod in one direction while rotation end coupler 435 in the opposite direction. During the rotation process, rotatable coupler 470 will also rotate to thereby transfer torque from one coil to the other.

In practice, applying torque to adjust the radial diameters of the coils is preferred over compressing or pulling the coils lengthwise since applying torque creates less of a gradient in the diameter of each coil. According, preferably, the treatment apparatus is constructed so that end coupler 435 remains stationary. Torque is preferably applied by manually rotating rod 430. When more than one coil is employed, a rotatable coupler is required to connect adjacent coils. Multiple coil configurations are preferred over one with a single coil that has the same length (in the relaxed state) as the sum of the lengths of the smaller coils since the diameters of the smaller coils will tend to be more uniform and in contact with the wall of the bronchial tube being treated. Each coil in the embodiment shown in FIG. 21 is connected to an appropriate source of energy. For example, coils 410 and 420 can be connected by lines 415 and 425 to a radio frequency generator 430 as described above. In operation, the heat treatment apparatus 40J is positioned at the treatment site before the diameters of the coils are adjusted by applying torque. Energy is then applied to the coils.

FIGS. 22 and 23 show embodiments of the heat treatment apparatus 40K, 40L for use with further methods of the present invention, which are similar to that of FIG. 21. The apparatus of FIG. 22 includes a pair of electrode coils 510 and 520 that are positioned in tandem. The apparatus also includes an elongated rod 530 which has a distal end 531 that is connected to a tip or knob 540 and has a proximal end which is at least partially slidably positioned inside aperture 551 of catheter sheath 550 that includes end coupler 535. Coil 510 has two ends, the first end 511 being attached to knob 540 and the second end 512 is attached to rotatable coupler 570. Similarly, coil 520 has two ends, the first end 521 is attached to rotatable coupler 570 and the second end 522 is attached to end coupler 535. As is apparent, each electrode has a cone-shaped contour and comprises a coil that is wound about and along the axis of the rod 530 and which in the relaxed state has a large diameter at one end and a small diameter at the other end.

The treatment apparatus 40L of FIG. 23 includes a pair of electrode coils 610 and 620 that are positioned in tandem. The apparatus also includes an elongated rod 630 which has a distal end 631 that is connected to a tip or knob 640 and has a proximal end which is at least partially slidably positioned inside aperture 651 of catheter sheath 650 that includes end coupler 635. Coil 610 has two ends, the first end 611 being attached to knob 640 and the second end 612 is attached to rotatable coupler 670. Similarly, coil 620 has two ends, the first end 621 is attached to rotatable coupler 670 and the second end 622 is attached to end coupler 635. As is apparent, each electrode has a single loop configuration that comprises a coil that is wound once about the rod 630. In this configuration, the two electrodes when in the relaxed state preferably form loops having the same diameter.

The devices 40K, 40L of FIGS. 22 and 23 operate in essentially the same manner as the device 40J of FIG. 21. Specifically, the same methods can be employed to adjust the radial diameter of the coils by compressing or pulling the coils or by applying torque to the coils. In addition, each coil is connected to an appropriate source of energy. For example, coils 610 and 620 can be connected by lines 615 and 625 to a radio frequency generator 330 as shown in FIG. 20A.

The electrodes may be constructed of a suitable current conducting metal or alloys such as, for example, copper, steel, and platinum. The electrodes can also be constructed of a shape memory alloy which is capable of assuming a predetermined, i.e., programmed, shape upon reaching a predetermined, i.e., activation, temperature. Such metals are well known in the art as described, for example, in U.S. Pat. Nos. 4,621,882 and 4,772,112 which are incorporated herein. For the present invention, the shape memory metal used should have the characteristic of assuming a deflection away (i.e., expands) from the elongated rod when activated, i.e., heated in excess of the normal body temperature and preferably between 60° C. and 95° C. A preferred shape memory alloy is available as NITINOL from Raychem Corp., Menlo Park, Calif. For the heat treatment apparatuses that employ coils as shown in FIGS. 20-23, preferably the electrodes are constructed of NITINOL in a predetermined shape and in the alloy's super elastic phase which can withstand very large deflections without plastic deformation.

Alternatively, the heat treatment apparatuses employing a unipolar electrode can also be employed. For instance, in the case of the embodiment shown in FIGS. 20A and 20B, the heating device can have one or more inner electrodes 302 and/or 304 on the balloon surface and an outer or external electrode 388 that has a much larger surface area than that of the internal electrode(s) and that is placed on the outer surface of the patient's body. For example, the external electrode can be an external metal mesh or solid plate that is placed on the skin with conductive gel. Both the internal and external electrodes are connected to an RF generator which produces an electric field at a high frequency within the balloon. Because the collective surface area of the internal electrode(s) is much smaller than that of the outer electrode, the density of the high frequency electric field is much higher around the internal electrode(s). The electric field reaches its highest density in the region near the internal electrode(s). The increased density of the field around the internal electrode(s) produces localized heating of the tissue to destroy smooth muscle tone and damage tissue to cause fibrosis, which stiffens the airway 25 so as to increase gas exchange performed by the lung.

As is apparent, the heat treatment apparatus can have more than one electrode that is positioned at or near the distal end of the elongated rod. For example, FIG. 24 depicts schematically the distal end 700 of a treatment apparatus 40M which comprises electrodes 701, 702, and 703. In this configuration, if the device operates in the bipolar mode, two of the three electrodes (e.g., 701 and 702) are connected to one pole of the RF generator and the other electrode (702) is connected to the other pole. Heat will be generated in the tissue adjacent the region between electrodes 701 and 702 and the region between electrodes 702 and 703. These electrodes 701, 702, and 703 can be attached to the exterior surface of a balloon, alternatively they represent adjustable coils in embodiments that do not require a balloon.

When the treatment apparatus 40M includes multiple electrodes, not all the electrodes need to be activated at the same time, that is, different combinations of electrodes can be employed sequentially. For example, in the case of the above described bipolar embodiment with three electrodes, electrodes 701 and 702 can be first activated to heat a section of the bronchial tube wall. During the heat treatment, electrode 703 can also be activated so that a second section of the bronchial tube wall is heat treated simultaneously. Alternatively, electrode 701 is disconnected to the RF generator before electrode 703 is activated so that the second section is treated subsequent to treatment of the first section.

In addition, when a treatment apparatus 40M includes multiple electrodes, the device can operate in the monopolar, bipolar mode, or both modes at the same time. For instance, electrodes 701 and 702 can be designed to operate in the bipolar mode while electrode 703 is designed to operate in the monopolar mode. As a further variation, the electrodes can be constructed of different materials and/or constructed to have different configurations. For example, electrode 701 can be made of a shape memory alloy and/or it can be a coil while each of the other electrodes 702 and 703 can be made of a non-shape memory material and/or it can be a band with a rectangular cross section.

The treatment apparatus can comprise more than one balloon that is attached to the elongated rod. For example, FIG. 25 depicts schematically the distal end of a treatment apparatus 40N for use with embodiments of the present invention, which comprises balloons 810 and 820. Electrodes 811 and 812 are attached to the exterior surface of balloon 810 and electrodes 821 and 822 are attached to the exterior surface balloon 820. The treatment apparatus 40N includes an elongated rod 860 which is positioned with the lumen of catheter sheath 850. The treatment apparatus 40N is preferably constructed in the same manner as the device shown in FIG. 20B except for the additional balloon. Operation of the device 40N is also similar although the surgeon has the choice of activating both sets of electrode simultaneously or one set at a time.

FIG. 26 illustrates another embodiment of a treatment apparatus 40P for use with the methods of the present invention. The treatment apparatus 40P is introduced through a catheter, bronchoscope, or other tubular introducer member 1012. The heat treatment apparatus includes a shaft 1014 and one or more electrodes 1016. Electrically connected to the electrodes 1016 is an RF generator 1018 or other energy source. The RF generator is controlled by a controller 1020. Although the invention will be described as employing an RF generator, other energy sources, such as alternating current and microwave may also be used.

In accordance with the embodiment of FIG. 26, the electrodes include a first conical electrode 1016A connected to an inner shaft 1022 and a second conical electrode 1016B connected to an outer shaft 1024. The conical electrodes 1016A, 1016B are positioned with their axes aligned and may be fixed or movable with respect to each other. Each of the conical electrodes 1016A, 1016B, includes at least two overlapping sections 1026. The sections 1026 are flexible and overlap one another to allow the electrodes 1016A, 1016B to be compressed within the lumen of the catheter 1012 for insertion into the bronchial tube of a patient. Once the catheter 1012 is positioned with a distal end at a desired treatment location within the bronchial tubes, the shaft 1014 is used to push the electrodes 1016A, 1016B out of the distal end of the catheter. Once deployed from the catheter 1012, the electrodes 1016A, 1016B expand radially outwardly until the distal ends of the electrodes contact the walls of the bronchial tube.

The electrodes 1016A, 1016B are electrically connected to the RF generator 1018 by electrical cables 1028, 1030. When the treatment apparatus 40P employs two electrodes 1016A, 1016B the two electrodes are preferably oppositely charged with one of the electrodes connected to a negative output of the RF generator and the other electrode connected to a positive output of the RF generator. Alternatively, both the electrodes 1016A, 1016B or a single electrode 1016 may be connected to the same output of the RF generator and an external electrode 1034 may be used. The external electrode 1034 is connected to an output of the RF generator 1018 having an opposite polarity of the output connected to the internal electrode 1016.

Figure 27:
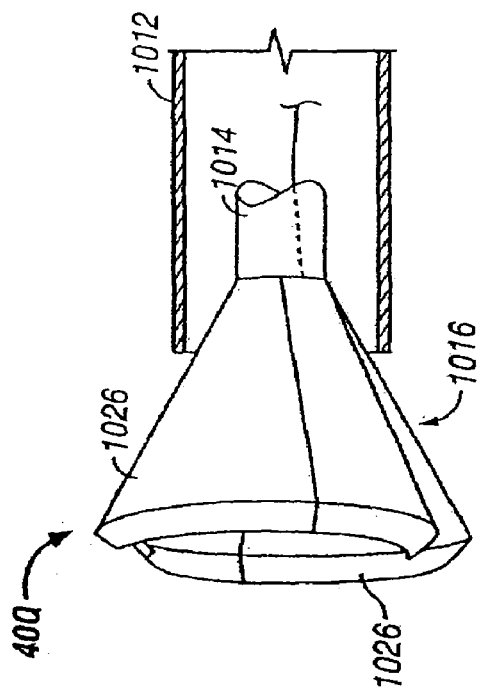
FIG. 27 is an enlarged partial cross-sectional view of a distal end of another embodiment of a heat treatment apparatus having one collapsible electrode for use with the methods of the present invention.

FIG. 27 illustrates an alternative embodiment of a heat treatment apparatus 1040 having a single electrode 1016 positioned on a shaft 1014. The electrode 1016 is shown as it is deployed from the distal end of a catheter 1012 for heat treatment of the lumen of bronchial tubes.

The electrodes 1016 of the embodiment of FIGS. 26 and 27 are formed of a suitable conductive material such as metal, plastic with a metal coating, or the like. The two or more sections 1026 of each of the cone shaped electrodes is fixed to the shaft 1014 and biased outwardly so that the sections expand or unfold to an enlarged diameter upon release from the distal end of the catheter 1012. The electrodes 1016 preferably have an enlarged diameter which is equal to or slightly greater than an interior diameter of the bronchial tube to be treated. As shown most clearly in FIG. 27, the sides of the sections 1026 overlap one another even in the expanded state.

In operation of the embodiments of FIGS. 26 and 27, the distal end of the catheter 1012 is first positioned at the treatment site by known catheter tracking methods. The catheter 1012 is then retracted over the heat treatment apparatus to expose and expand the electrodes 1016. Each electrode 1016 of the energy emitting apparatus 40P expands radially outward upon retraction of the catheter 1012 until the electrodes come into contact with the wall of the bronchial tube. In the embodiment of FIG. 27, the distance between the two energy emitting electrodes 1016A, 1016B may be fixed or may be changeable by sliding the inner shaft 1022 within the outer shaft 1024. When treatment is completed the heat treatment apparatus 40P is retracted back inside the catheter 1012 by sliding the catheter over the electrodes. As the heat treatment apparatus 40P is retracted the sides of the sections 1026 of the electrode 1016 slide over each other upon coming into contact with a distal edge of the catheter 1012.

Figure 28:
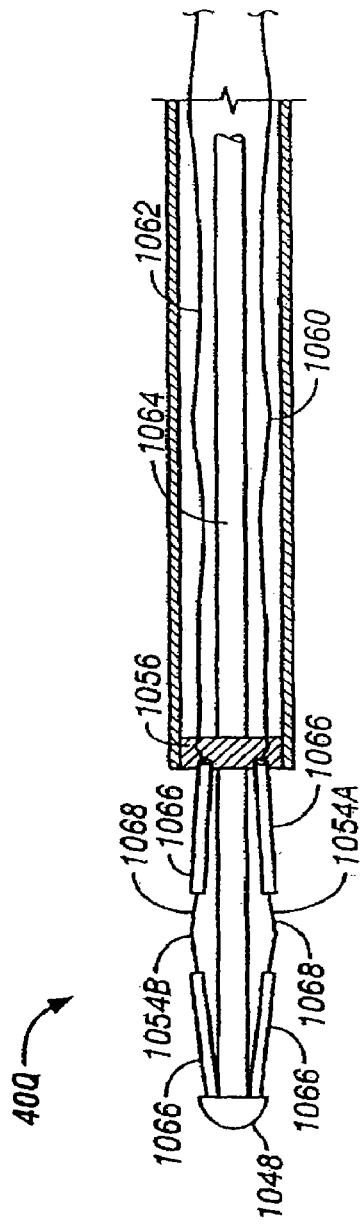
FIG. 28 is a side cross-sectional view of an alternative embodiment of a heat treatment apparatus having two wire shaped electrodes for use with the methods of the present invention.

FIGS. 28 and 29 illustrate an alternative embodiment of a treatment apparatus 40Q for use with the methods of the present invention. The treatment apparatus 40Q may be delivered to a treatment site in a collapsed configuration illustrated in FIG. 28. The treatment apparatus 40Q includes two leaf spring or wire shaped electrodes 1054A and 1054B. The electrodes 1054A, 1054B are connected to an insulating end cap 1056 of a hollow shaft 1058. The electrodes 1054A, 1054B are electrically connected to the RF generator or other energy source by electric cables 1060, 1062. The heat treatment apparatus 1050 is provided with a central shaft 1064 which is slidable within the hollow shaft 1058. The central shaft 1064 has a shaft tip 1048 which is connected to a distal end of each of the electrodes 1054A, 1054B.

Each of the electrodes 1054A, 1054B is preferably insulated with an insulating sleeve 1066 except for an exposed contact section 1068. The treatment apparatus 40Q is delivered to the lumen of a bronchial tube to be treated either alone or through a catheter, bronchoscope, or other channel. The electrodes 1054A, 1054B are expanded radially outwardly by moving the central shaft 1064 proximally with respect to the hollow shaft 1058 of the treatment apparatus 40Q. Upon expansion, the exposed contact sections 1068 of the electrodes 1054A, 1054B come into contact with the walls of the airway or bronchial tube B, shown in FIG. 29. The electrodes 1054A, 1054B may be configured to bend at a predetermined location forming a sharp bend as shown in FIG. 29. Alternatively, the electrodes 1054A, 1054B may form a more gradual curve in the expanded configuration. The electrodes 1054A, 1054B are preferably connected to opposite poles of the energy source. Alternatively, both of the electrodes 1054A, 1054B may be connected to the same lead of the energy source and the external electrode 1034 may be used. Upon completion of the treatment process the electrodes 1054 are retracted back into the catheter for removal or moving to a subsequent treatment site.

FIGS. 30 and 30A illustrate another embodiment of the treatment apparatus 40R for use with embodiments of the present invention. The treatment apparatus 40R includes four electrodes 1054A, 1054B, 1054C, 1054D. The four electrode embodiment of FIGS. 30 and 30A operates in the same manner as the embodiments of FIGS. 28 and 29 with a slidable central shaft 1064 employed to move the electrodes from a compressed configuration to the expanded configuration illustrated in FIGS. 30 and 30A. Each electrode 1054A-1054D is connected at a proximal end to the insulating end cap 1056 of the hollow shaft 1058 and at a distal end to the central shaft 1064. Relative motion of the hollow shaft 1058 with respect to the central shaft 1064 moves the electrodes 1054 from the collapsed to the expanded position.

FIGS. 31 and 32 illustrate a further embodiment of a heat treatment apparatus 40S employing one or more wire or leaf spring shaped loop electrodes 1094. As in the previous embodiments, the loop electrode 1094 expands from a contracted positioned within a catheter 1092 as illustrated in FIG. 31 to an expanded position illustrated in FIG. 32. In the expanded position, the loop shaped electrode 1094 comes into contact with the walls of the airway or bronchial tube B. Although the embodiment of FIGS. 31 and 32 has been illustrated with a single loop shaped electrode 1094, it should be understood that multiple loop shaped electrodes may also be use. The loop shaped electrode 1092 is connected to the shaft 1096 of the heat treatment apparatus 40S by an end cap 1098 and is electrically connected to the energy source by the electric cables 1100.

FIGS. 33-36 illustrate an alternative embodiment of a treatment apparatus 40T for use with the embodiments of the present invention. The treatment apparatus 40T includes a flexible plate shaped electrode 1114. The flexible plate shaped electrode 1114 is substantially flower shaped in plan having a plurality of petals 1116 with curved distal ends extending from a central section 1120. The petals 1116 flex along a hinge line 1118 to the compressed insertion configuration illustrated in FIG. 33 in which the petals 1116 extend substantially perpendicularly from the central section 1120 of the flexible plate shaped electrode 1114.

Figure 35:
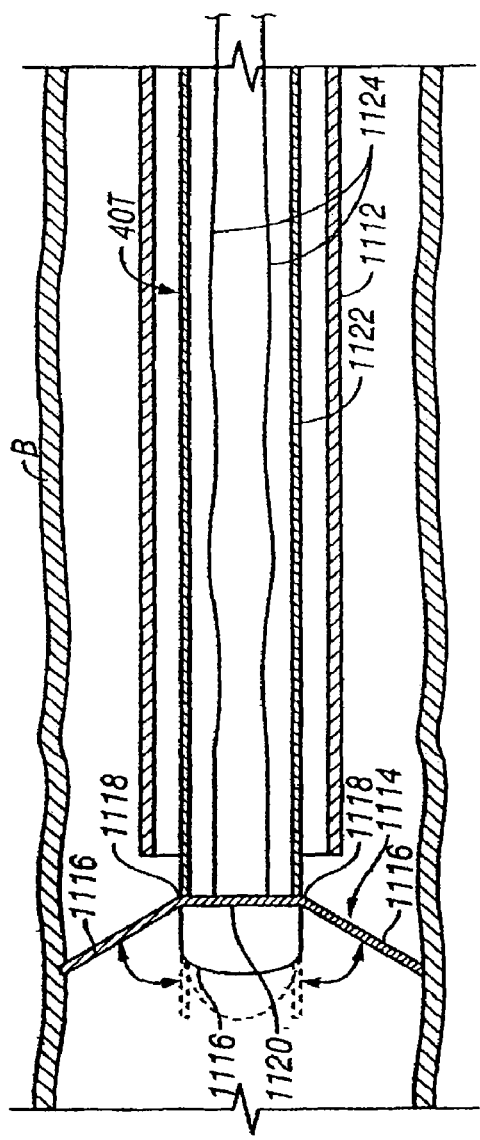
FIG. 35 is a side cross-sectional view of the apparatus of FIG. 33 with the plate shaped electrodes in an expanded configuration.
Figure 36:
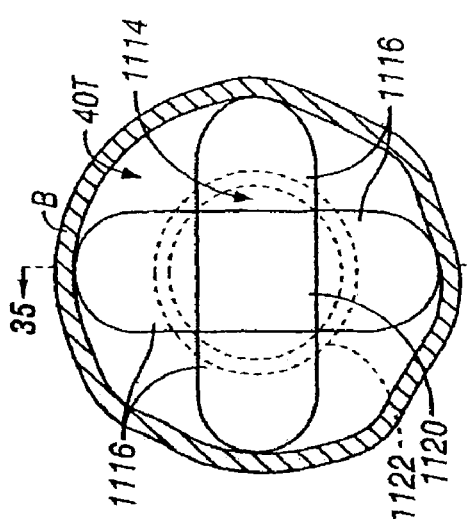
FIG. 36 is an end view of the expanded apparatus of FIG. 35 for use with the methods of the present invention.

As illustrated in FIGS. 35 and 36, when the treatment apparatus 40T is moved distally with respect to the catheter 1112 to deploy the electrode 1114 the petals 1116 move outwardly until the petal tips come into contact with the walls of the bronchial tube B. The flexible plate shaped electrode 1114 is preferably formed of a conductive material and fixed to the end of a shaft 1122. Electric cables 1124 connect the plate shaped electrode 1114 to the energy source.

The electrodes in each of the forgoing embodiments may be fabricated of any material which when compressed will return to an expanded configuration upon release of the compression forces. For example, one method of controlling the expansion of the electrodes is the use of shape memory alloy electrodes. With a shape memory alloy, the constraint of the electrodes within a catheter may not be necessary. The shape memory alloy electrodes may be formed to expand to an expanded energy delivery configuration upon heating to body temperature within the body. The expansion of the electrodes is limited by the size of the bronchial tube in which the electrode is positioned.

As described above, the heat treatment apparatus may be employed in a bipolar mode in which two different expandable electrodes are connected to two different outputs of the RF generator 1018 having opposite polarities. For example, the electrodes 1016A, 1016B may be connected by the electrical cables 1028, 1030 to different terminals of the RF generator 1018. Alternatively, when more than two electrodes 16 are employed, multiple electrodes may be connected to one terminal of the RF generator. In each of the embodiments of the heat treatment apparatus, the oppositely charged electrodes are separated by an insulating material. For example, in the embodiment of FIG. 36, the inner shaft 1022 and outer shaft 1024 are formed of an insulating material. Further, in the embodiments of FIGS. 28-30 the end cap 1056 and central shaft distal tip are formed of insulating materials.

In the case where the apparatus includes only one electrode 1016 as shown in FIG. 27, the electrode will be connected to the positive or negative terminal of the RF generator 1018 and the opposite terminal of the RF generator will be connected to the external electrode 1032.

The frequency range of RF radiation useful in the present invention is typically about 10 KHz to about 100 MHZ, preferably in the range of about 200 KHz to about 800 KHz. However, frequencies outside this range may be used at the discretion of the operating surgeon. Typically, the amount of power employed will be from about 0.01 to 100 watts and preferably in the range of about 1 to 25 watts for about 1 to 60 seconds. Alternatively, alternating current or microwave radiation typically in the frequency range of about 1,000 MHZ to about 2,000 MHZ and preferably from about 1,100 MHZ to about 1,500 MHZ may be used in place of RF radiation. In the latter case, the RF generator 1018 is replaced with a microwave generator, and the electric cables 1028, 1030 are replaced with waveguides.

When the heat treatment apparatus with the bipolar electrodes is positioned inside the lumen of a bronchial tube, activation of the RF generator 1018 causes tissue in the lumen wall to increase in temperature. The heating may be caused by resistance heating of the electrodes themselves and/or power losses through the tissue of the bronchial wall. The particular heat pattern in the tissue will depend on the path of the electric field created by the positioning and configuration of the electrodes.

In the monopolar mode, the external electrode 1034, shown in FIG. 26, having a much larger surface area than the inner electrodes is placed on the outer surface of the patient's body. For example, the external electrode 1034 can be an external metal mesh or a solid plate that is placed on the skin with conductive gel. Both the internal and external electrodes are connected to the RF generator 1018 which produces an electric field at a high frequency. Because the collective surface area of the internal electrodes is much smaller than that of the outer electrode 1034, the density of the high frequency electric field is much higher around the internal electrodes. The electric field reaches its highest density in the region near the internal electrodes. The increased density of the field around the internal electrodes produces localized heating of the tissue around the bronchial tube without causing significant heating of the body tissue between the bronchial tube and the external electrode.

In use, after the operating surgeon has placed the heat treatment apparatus within the lumen of a bronchial tube to be treated, if necessary, the catheter is retracted to expose the electrodes. In the case where the lumen of the bronchial tube has collapsed or is partially collapsed, the size of the energy emitting device is designed so that expansion of the electrodes causes the lumen to expand to its normal or non-collapsed diameter due to contact of the electrodes with the inner surface of the lumen. Alternatively, in the case where the lumen has not collapsed, the device is designed so that upon expansion the electrodes are in substantial contact with the inner surface of the lumen. Indeed, only minimum expansion may be necessary in treating a non-collapsed bronchial lumen.

The degree of expansion of the electrodes of the heat treatment apparatus can be monitored by means of endoscopy, fluoroscopy, or by other suitable imaging methods of the art. Generally, the heat required is induced in the tissue of the bronchial tube wall by the RF or microwave radiation emitting from the electrodes. The RF or microwave energy is applied while observing the tissue for changes via simultaneous endoscopy, or other suitable imaging methods of the art.

The electrodes employed in the heat treatment apparatus are constructed of a suitable current conducting metal or alloys such as, for example, copper, steel, platinum, and the like or of a plastic material with a conductive metal insert. The electrodes can also be constructed of a shape memory alloy which is capable of assuming a predetermined, i.e., programmed, shape upon reaching a predetermined, i.e., activation, temperature. Such metals are well known in the art as described, for example, in U.S. Pat. Nos. 4,621,882 and 4,772,112 which are incorporated herein by reference. For the present invention, the shape memory metal used should have the characteristic of assuming a deflection away (i.e., expands) from the elongated rod when activated, i.e., heated in excess of the normal body temperature and preferably between 60° C. and 95° C. A preferred shape memory alloy is available as NITINOL from Raychem Corp., Menlo Park, Calif. In one embodiment, the electrodes are constructed of NITINOL in a predetermined shape and in the alloy's super elastic phase which can withstand very large deflections without plastic deformation.

Substantial tissue transformation may be achieved very rapidly, depending upon the specific treatment conditions. Because the transformation can proceed at a rather rapid rate, the RF energy should be applied at low power levels. Preferably, the RF energy is applied for a length of time in the range of about 0.1 second to about 600 seconds, and preferably about 1 to about 60 seconds. Suitable RF power sources are commercially available and well known to those skilled in the art. In one embodiment the RF generator 18 employed has a single channel, delivering approximately 1 to 100 watts, preferably 1 to 25 watts and possessing continuous flow capability. The rate of tissue damage to induce fibrosis can be controlled by varying the energy delivered to the heat treatment apparatus. Regardless of the source of energy used during treatment, the lumen or the bronchial tube is maintained at a temperature of at least about 45° C., preferably between 60° C. and 95° C.

When the heat treatment apparatus includes multiple energy emitting devices, not all the electrodes need to be activated at the same time. That is, different combinations of electrodes can be employed sequentially. For example, in the case of the embodiment shown in FIG. 26, with two electrodes 1016A, 1016B, the electrodes can be activated simultaneously or sequentially.

In addition, when a heat treatment apparatus includes multiple energy emitting devices, the apparatus can operate in the monopolar, bipolar mode, or both modes at the same time. For instance, one of the electrodes can be designed to operate in the bipolar mode while another electrode operates in the monopolar mode.

When treating a person with obstructed air passages, a preliminary diagnosis is made to identify the air passages or bronchial tube that can be treated. In treating a particular site, excessive fluid is first removed from the obstructed air passage by conventional means such as with a suction catheter. Thereafter, the heat treatment apparatus is maneuvered to the treatment site. Depending on the diameter of the lumen of the bronchial tube, the device can be positioned directly at the treatment site or it can be positioned into place with a bronchoscope. The elongated shafts 1022, 1024 and outer catheter 1012 are preferably made of a flexible material so that the catheter can be maneuvered through a bronchoscope. A bronchoscope is a modified catheter which includes an illuminating and visualization instrument for monitoring the treatment site and a channel for passing instruments (e.g., the treatment apparatus) into the bronchial tubes.

In operation, the bronchoscope is advanced from the person's nasal or oral cavity, through the trachea, main stem bronchus, and into an obstructed air passage. The heat treatment apparatus is advanced forward through the bronchoscope to expose the tip of the heat treatment apparatus before the heat treatment apparatus is energized. Depending on the size of the treatment apparatus, the treatment apparatus can be moved to another position for further heat treatment of the air passage. This process can be repeated as many times as necessary to form a series of patency bands supporting an air passage. This procedure is applied to a sufficient number of air passages until the physician determines that he is finished. As is apparent, the procedure can be completed in one treatment or multiple treatments. After completion of the treatment, energy is discontinued and the heat treatment apparatus is removed from the patient.

Temperature monitoring and impedance monitoring can be utilized in a system which provides feedback to the user in the form of sounds, lights, other displays or a mechanism which shuts down the application of energy from the heating element to the treatment site when sufficient tissue transformation is detected and to avoid burning of the treatment site. The amount of energy applied can be decreased or eliminated manually or automatically under certain conditions. For example, the temperature of the wall of the air passage, or of the heating element can be monitored and the energy being applied adjusted accordingly. The surgeon can, if desired, override the feedback control system. A microprocessor can be included and incorporated into the feedback control system to switch the power on and off, as well as to modulate the power. The microprocessor can serve as a controller to monitor the temperature and modulate the power.

The invention is also directed to the demonstration or instruction of the inventive surgical techniques including, but not limited to, written instructions, actual instructions involving patients, audio-visual presentations, animal demonstrations, and the like.

Figure 37:
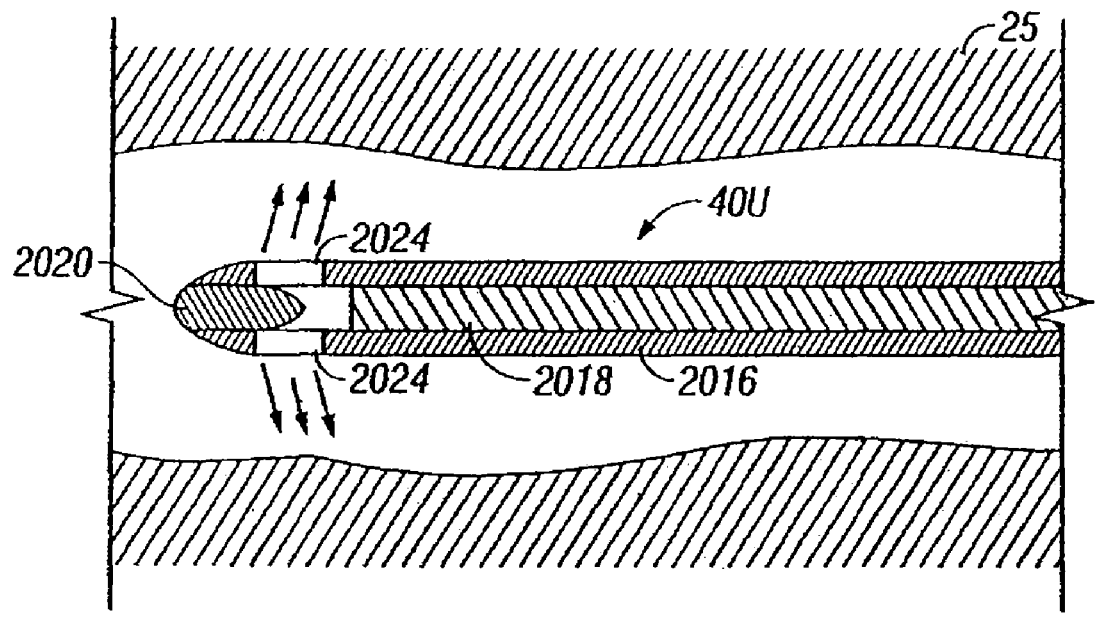
FIG. 37 is a side cross-sectional view of a body conduit and an apparatus for treating the body conduit according to the present invention.

As described above, the apparatus 40 of the present invention may damage cells of the airway to cause fibrosis to stiffen the airway 25 in other manners besides those described above. For example, FIG. 37 illustrates another treatment apparatus 40U that delivers light to the walls of the airway 25. The light delivery device 40U includes an outer catheter or sheath 2016 surrounding a light transmitting fiber 2018. A light directing member 2020 is positioned at a distal end of the light delivery device 2010 for directing the light to the conduit walls.

The light delivery device 40U is used to irradiate the smooth muscle surrounding the airways to induce fibrosis and/or destroy smooth muscle tone of the airway.

Figure 38:
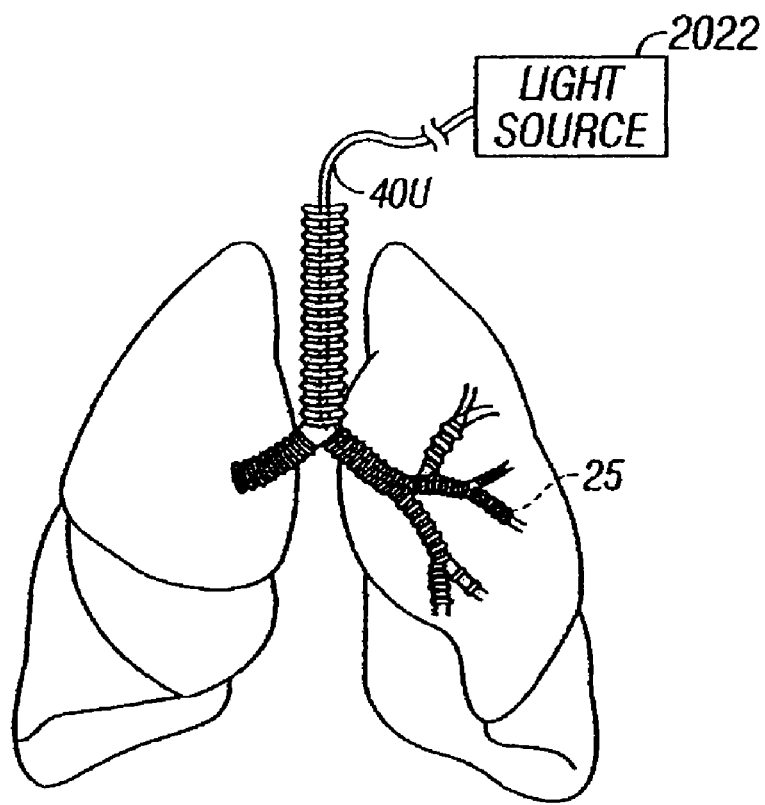
FIG. 38 is a schematic side view of lungs being treated with a treatment apparatus in accordance with one aspect of the present invention.

As shown in FIG. 38, the light delivery device 40U is an elongated device such as a catheter containing a fiber optic. The light delivery device 40U is connected by a conventional optical connection to a light source 2022. The treatment of an airway with the light delivery device 40U involves placing a visualization system such as an endoscope or bronchoscope into the airways. The light delivery device 40U is then inserted through or next to the bronchoscope or endoscope while visualizing the airways. The light delivery device 40U which has been positioned with a distal end within an airway to be treated is energized so that radiant energy is emitted in a generally radially direction from a distal end of the light delivery device. The distal end of the light delivery device 40U is moved through the airway in a uniform painting like motion to expose the entire length of an airway to be treated to the light. The light delivery device 40U may be passed along the airway one or more times to achieve adequate treatment. The painting like motion used to exposed the entire length of an airway to the light may be performed by moving the entire light delivery device from the proximal end either manually or by motor.

The light used may be coherent or incoherent light in the range of infrared, visible, or ultraviolet. The light source 2022 may be any known source, such as a UV laser source. Preferably the light is ultraviolet light having a wavelength of about 240-350 nm or visible light in the red visible range. The intensity of the light may vary depending on the application. The light intensity should be bright enough to damage the cells of the tissue to induce fibrosis and/or to destroy the smooth muscle tone or the airway. The light intensity may vary depending on the wavelength used, the application, the thickness of the smooth muscle, and other factors.

Figure 39:
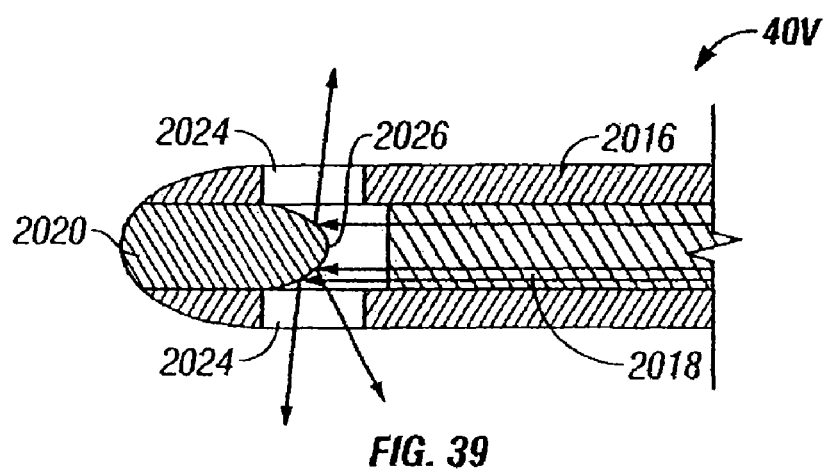
FIG. 39 is a side cross-sectional view of a distal end of an embodiment of a treatment apparatus for use with the methods of the present invention.

FIGS. 39-42 illustrate different exemplary embodiments of the distal tip of the light delivery device for irradiating the airway walls. In FIG. 39, a light delivery device 40V includes a sheath 2016 having a plurality of windows 2024 which allow the light which has been redirected by the light directing member 2020 to pass substantially radially out of the sheath. The light directing member 2020 is fitted into the distal end of the sheath 2016. The light directing member 2020 is a parabolic diffusing mirror having a reflective surface 2026 which is substantially parabolic in cross section. The light passes from the light source along the light transmitting fiber 2018 and is reflected by the reflective surface 2026 of the light directing member 2020 through the windows 2024. The windows 2024 are preferably a plurality of light transmitting sections spaced around the distal end of the sheath. The windows 2024 may be open bores extending through the sheath 2016. Alternatively, the windows 2024 may be formed of a transparent material which allows the light to pass out of the sheath 2016.

Figure 40:
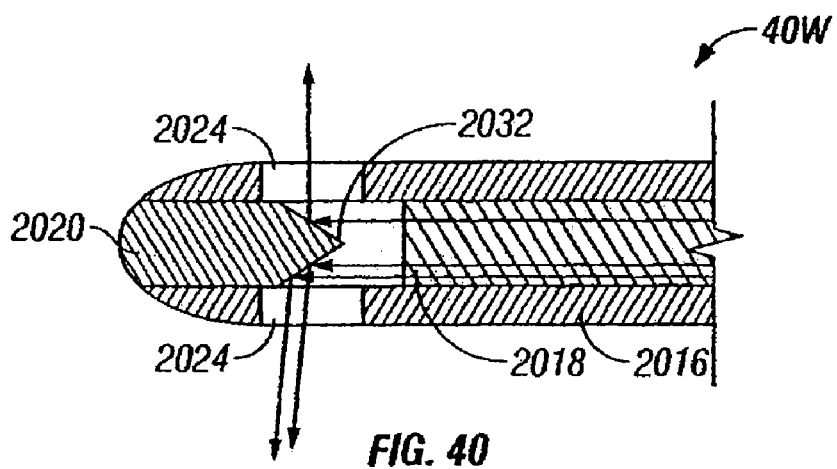
FIG. 40 is a side cross-sectional view of a distal end of another embodiment of a treatment apparatus for use with the methods of the present invention.

FIG. 40 illustrates an alternative embodiment of a light delivery device 40W in which the light directing member 2020 has a conical shaped reflective surface 2032. This conical shaped reflective surface may be formed at any desired angle which directs the light transmitted by the light transmitting fiber 2018 radially out of the sheath 2016. The use of a conical reflective surface 2032 creates a light delivery pattern in which the light rays are directed in a generally coherent radial pattern which is at a generally fixed angle with respect to a longitudinal axis of the light delivery device. In contrast, the light delivery device of FIG. 39 with the parabolic reflective surface 2026 directs light in a diverging radial pattern which will illuminate a larger area of the airway walls.

Figure 41:
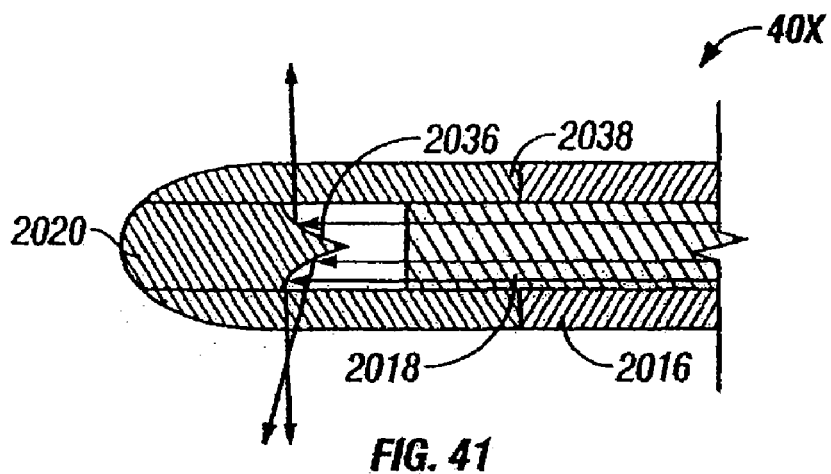
FIG. 41 is a side cross-sectional view of a distal end of a further embodiment of a treatment apparatus for use with the methods of the present invention.

FIG. 41 illustrates a further alternative embodiment of a light delivery device 40X in which the light directing member 2020 is a substantially conical member including concave reflective surfaces 2036. These concave reflective surfaces 2036 direct the light which passes in a generally parallel arrangement through the light transmitting fiber 2018 out of the sheath 2016 in a converging or crossing pattern. In addition, in the embodiment of FIG. 41, the windows have been replaced by a transparent tip 2038 of the sheath 2016.

The light directing members 2020 having a reflective surface as illustrated in FIGS. 39-41 may be formed in any of the known manners, such as by coating a molded member with a reflective coating, such as aluminum.

Figure 42:
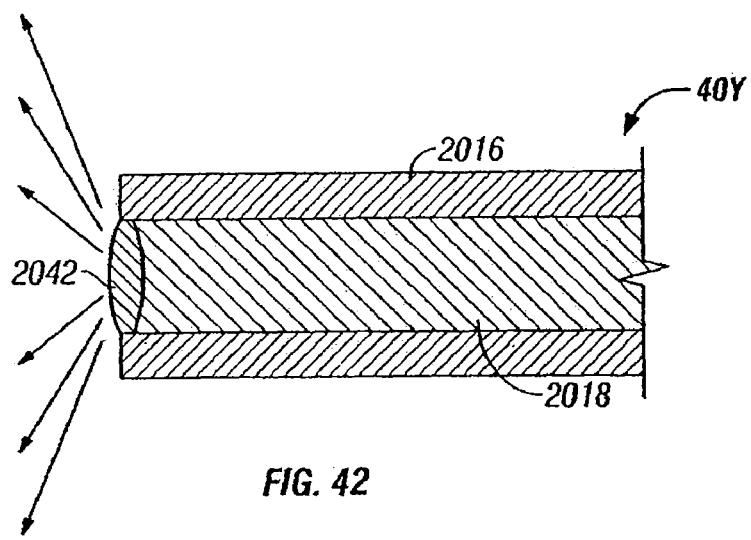
FIG. 42 is a side cross-sectional view of another embodiment of a treatment apparatus for use with the methods of the present invention.

As an alternative to the reflective light directing members of FIGS. 39-41, treatment apparatus 40Y includes a diffusing lens 2042, such as a Teflon lens, that may be positioned at the end of the light transmitting fiber 2018 as illustrated schematically in FIG. 42. The diffusing lens 2042 may direct the light from the light transmitting fiber 2018 in a generally conical pattern as shown in FIG. 42. Alternatively, the diffusing lens 2042 may direct the light in a more radially oriented pattern with the light rays being prevented from exiting the lens in a direction substantially parallel with the longitudinal axis of the light transmitting fiber 2018 by a reflective or blocking member. In the embodiment of FIG. 42, the sheath 2016 surrounding the light transmitting fiber 2018 and the diffusing lens 2042 may be eliminated entirely and the lens may be affixed directly to the end of the fiber.

According to one alternative embodiment, the light delivery devices 40U, 40V, 40W, 40X, 40Y can be used in conjunction with photo activatable substances such as those known as psoralens. These light activatable compounds, when activated, enhance the ability of visible light to destroy tissue. The psoralens may by injected intravenously. The light delivered by the light delivery devices is matched to the absorption spectrum of the chosen psoralens such that the light exposure activates the compound. When such light activatable substances are employed, a lower light intensity may be used to cause trauma to the tissue than the light intensity required to achieve destruction without the light activatable compounds.

Figure 54:
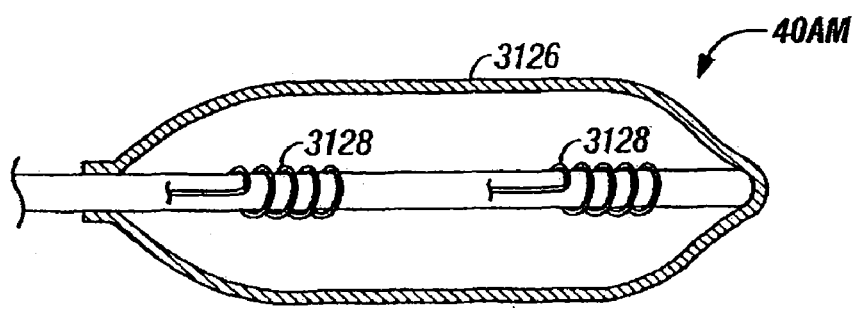
FIG. 54 is a schematic side view of an embodiment of a treatment apparatus with a balloon for heating of tissue for use with the methods of the present invention.
Figure 55:
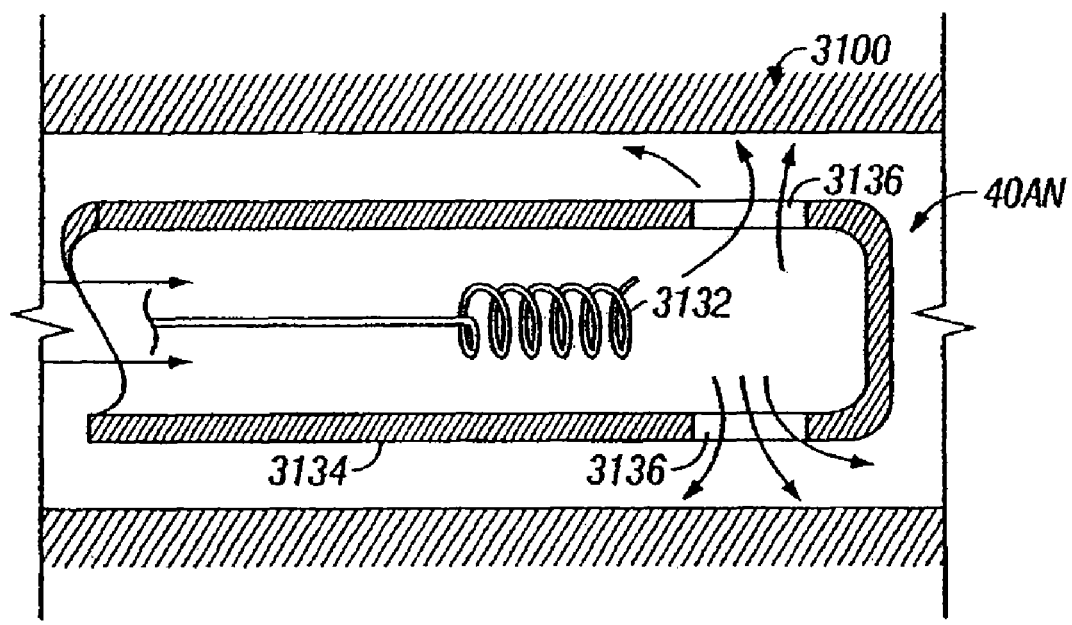
FIG. 55 is a side cross-sectional view of another embodiment of a treatment apparatus for treatment with heated fluid.
Figure 56:
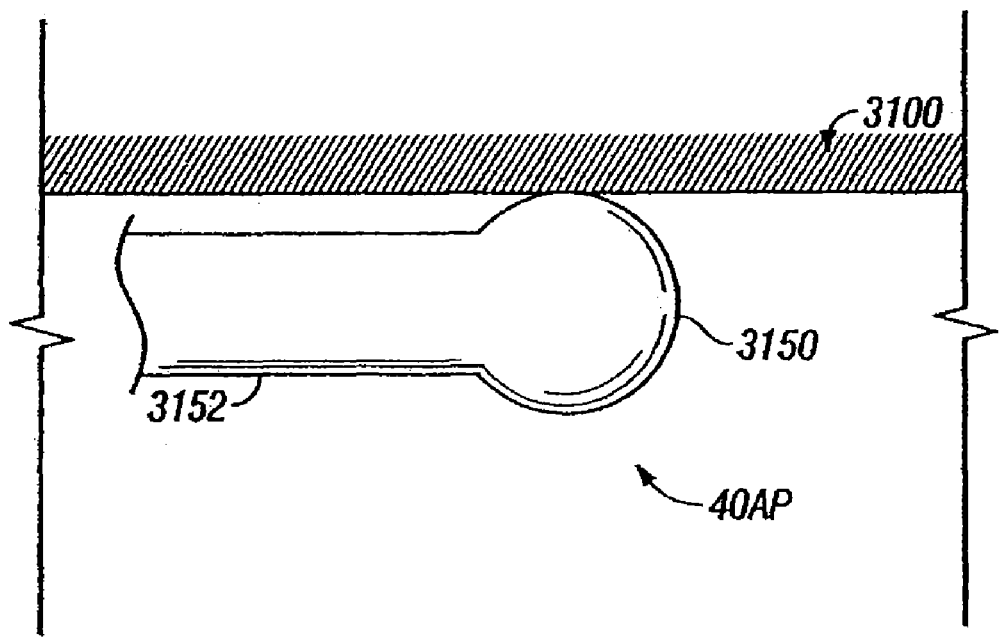
FIG. 56 is a side view of a treatment apparatus having a cryoprobe for use with the methods of the present invention.

FIGS. 43-56 illustrate further embodiments of treatment apparatus that may be used with the methods of the present invention. The treatment apparatus of FIGS. 43-53 include tissue contacting electrodes configured to be placed within the airway. These apparatus can be used for delivering radio frequency in either a monopolar or a bipolar manner or for delivering other energy to the tissue, such as conducted heat energy from resistively heated electrodes, similar to the previously described treatment apparatus. For monopolar energy delivery, one or more electrodes of the treatment apparatus are connected to a single pole of the energy source 3032 and an optional external electrode 3044 is connected to an opposite pole of the energy source. For bipolar energy delivery, multiple electrodes are connected to opposite poles of the energy source 3032 and the external electrode 3044 is omitted. The number and arrangement of the electrodes may vary depending on the pattern of energy delivery desired. The treatment apparatus of FIGS. 54 and 55 are used to deliver radiant or heat energy to the airway. The treatment apparatus of FIG. 54 can also deliver indirect radio frequency or microwave energy to the tissue. Finally, the treatment apparatus of FIG. 56 is used to remove heat energy from the tissue.

Figure 43A:
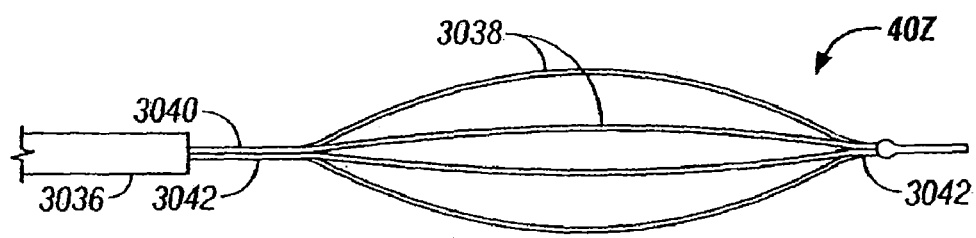
FIGS. 43A and 43B are side views of two variations of an embodiment of a treatment apparatus having a plurality of wire shaped electrodes for use with the methods of the present invention.

The treatment apparatus 40Z of FIG. 43A includes a catheter 3036 for delivering a shaft 3040 having a plurality of electrodes 3038 to a treatment site. The electrodes 3038 are formed from a plurality of wires which are soldered or otherwise connected together at two connection areas 3042. The electrodes 3038 between the connection areas 3042 are formed into a basket shape so that arch shaped portions of the wires will contact the walls of an airway. The wires may be coated with an insulating material except at the tissue contact points. Alternatively, the wires of the basket may be exposed while the connection areas 3042 and shaft 3040 are insulated. Preferably, the electrodes 3038 are formed of a resilient material which will allow the distal end of the treatment apparatus to be retracted into the catheter 3036 for delivery of the catheter to the treatment site and will allow the electrodes to return to their original basket shape upon deployment. The treatment apparatus 40Z is preferably configured such that the electrodes 3038 have sufficient resilience to come into contact with the airway walls for treatment.

Figure 43B:
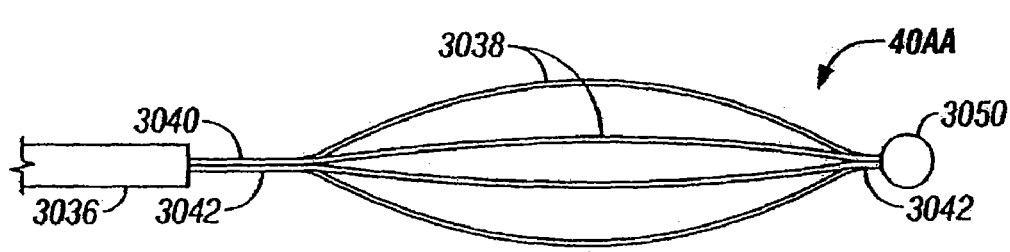
Figure 43C:
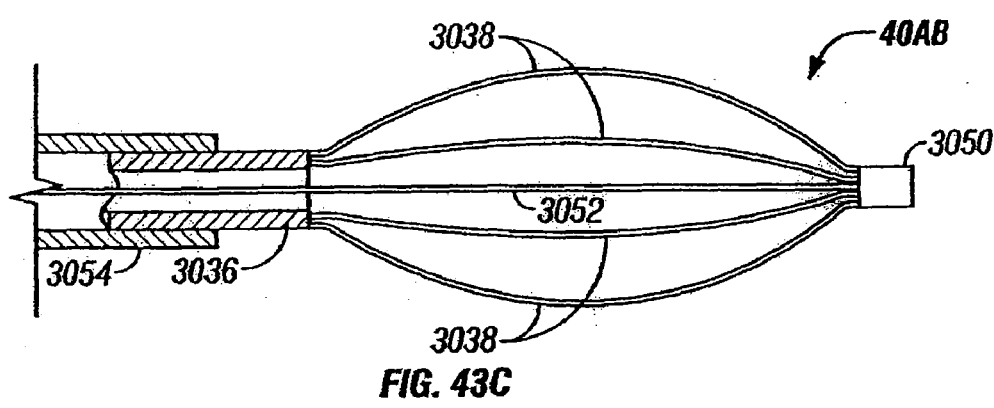
FIG. 43C is a cross-sectional side view of another variation of a treatment apparatus having a plurality of wire shaped electrodes for use with the methods of the present invention.

FIG. 43B illustrates a treatment apparatus 40AA in which the distal end of the device is provided with a ball shaped member 3050 for easily inserting the device to a treatment site without causing trauma to surrounding tissue. FIG. 43C illustrates a treatment apparatus 40AB having electrodes 3038 connected to the distal end of the catheter 3036 and forming a basket shape. The basket shape may be expanded radially during use to insure contact between the electrodes 3038 and the airway walls by pulling on a center pull wire 3052 which is connected to a distal end 3050 of the device and extends through a lumen of the catheter 3036. The treatment apparatus 40A may be delivered to a treatment site through a delivery catheter or sheath 3054 and may be drawn along the airway to treat the airway in a pattern of longitudinal or helical stripes.

Figure 44:
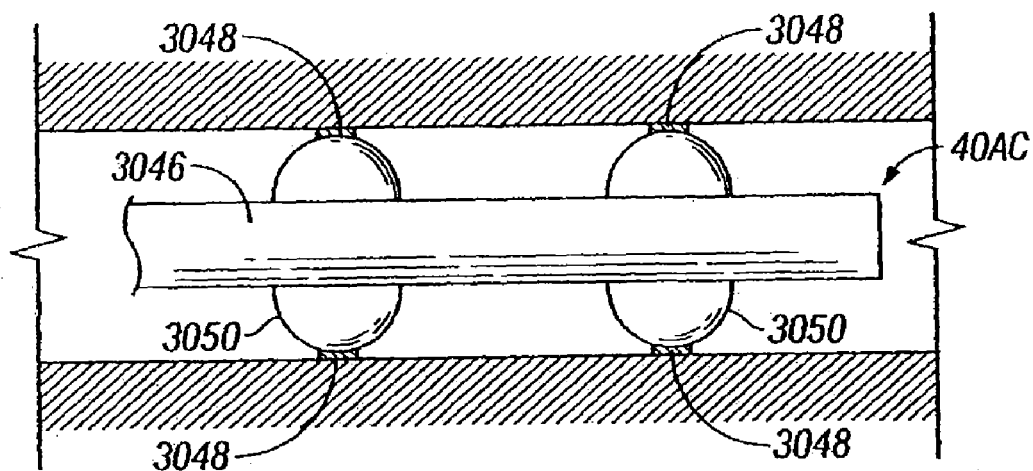
FIG. 44 is a side view of another embodiment of a treatment apparatus with electrodes positioned on expandable balloons for use with the methods of the present invention.

FIG. 44 illustrates a treatment apparatus 40AC in which a catheter shaft 3046 is provided with a plurality of electrodes 3048 positioned on inflatable balloons 3050. The balloons 3050 are inflated through the catheter shaft 3046 to cause the electrodes 3048 come into contact with the airway walls 3100. The electrodes 3048 are preferably connected to the energy source 3032 by conductive wires (not shown) which extend from the electrodes through or along the balloons 3050 and through the catheter shaft 3046 to the energy source. The electrodes may be used in a bipolar mode without an external electrode. Alternatively, the treatment apparatus 40C may be operated in a monopolar mode with an external electrode 3044. The electrodes 3048 may be continuous circular electrodes or may be spaced around the balloons 3050.

Figure 45:
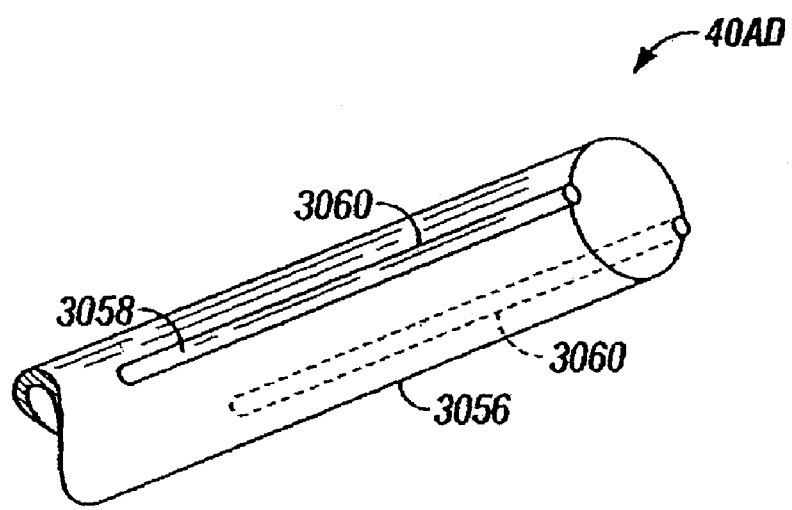
FIG. 45 is a perspective view of an embodiment of a treatment apparatus with electrodes positioned in grooves for use with the methods of the present invention.

An alternative apparatus device 40AD of FIG. 45 includes a catheter 3056 having one or more grooves 3060 in an exterior surface. Positioned within the grooves 3060 are electrodes 3058 for delivery of energy to the airway walls. Although the grooves 3060 have been illustrated in a longitudinal pattern, the grooves may be easily configured in any desired pattern. Preferably, the treatment apparatus 40D of FIG. 45 includes a biasing member (not shown) for biasing the catheter 3056 against the airway wall such that the electrodes 3058 contact the tissue. The biasing member may be a spring element, an off axis pull wire, an inflatable balloon element, or other biasing member. Alternatively, the biasing function may be performed by providing a preformed curve in the catheter 3056 which causes the catheter to curve into contact with the airway wall when extended from a delivery catheter.

Figure 46:
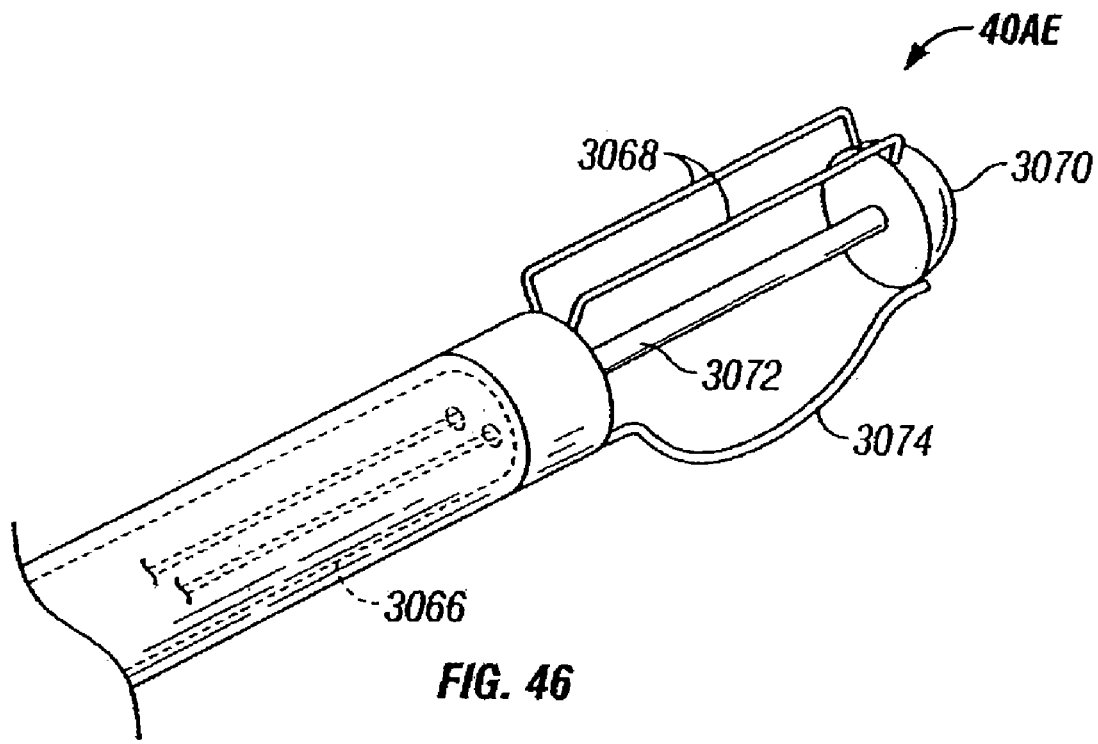
FIG. 46 is a perspective view of an embodiment of a treatment apparatus with electrodes in a biasing element for use with the methods of the present invention.

FIG. 46 illustrates a treatment apparatus 40AE having one or more electrodes 3068 connected to a distal end of a catheter 3066. The electrodes 3068 are supported between the distal end of the catheter 3066 and a device tip 3070. A connecting shaft 3072 supports the tip 3070. Also connected between the distal end of the catheter 3066 and the tip 3070 is a spring element 3074 for biasing the electrodes 3068 against a wall of the airway. The spring element 3074 may have one end which slides in a track or groove in the catheter 3066 such that the spring can flex to a variety of different positions depending on an internal diameter of the airway to be treated.

Figure 47:
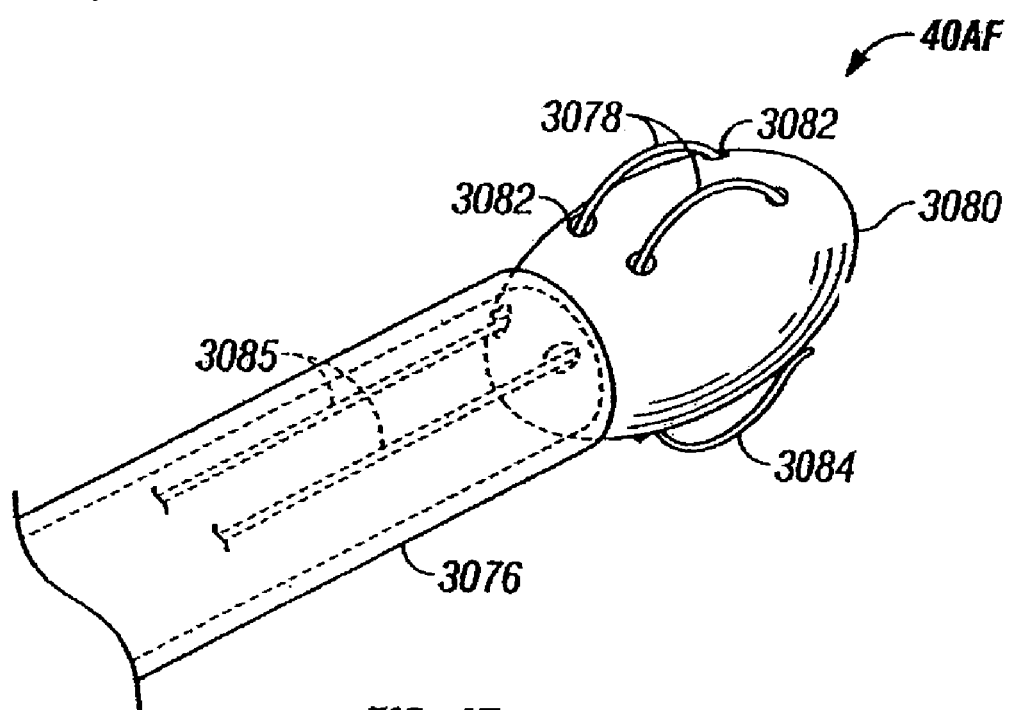
FIG. 47 is a perspective view of an embodiment of a treatment apparatus with electrodes and a biasing element for use with the methods of the present invention.

FIG. 47 illustrates an alternative treatment apparatus 40AF in which the one or more electrodes 3078 are positioned on a body 80 secured to an end of a catheter 3076. In the FIG. 47 embodiment, the body 3080 is illustrated as egg shaped, however, other body shapes may also be used. The electrodes 3078 extend through holes 3082 in the body 3080 and along the body surface. A biasing member such as the spring element 3084 is preferably provided on the body 3080 for biasing the body with the electrodes against the airway walls. Leads 3085 are connected to the electrodes and extend through the catheter 3076 to the energy source 3032.

Figure 48:
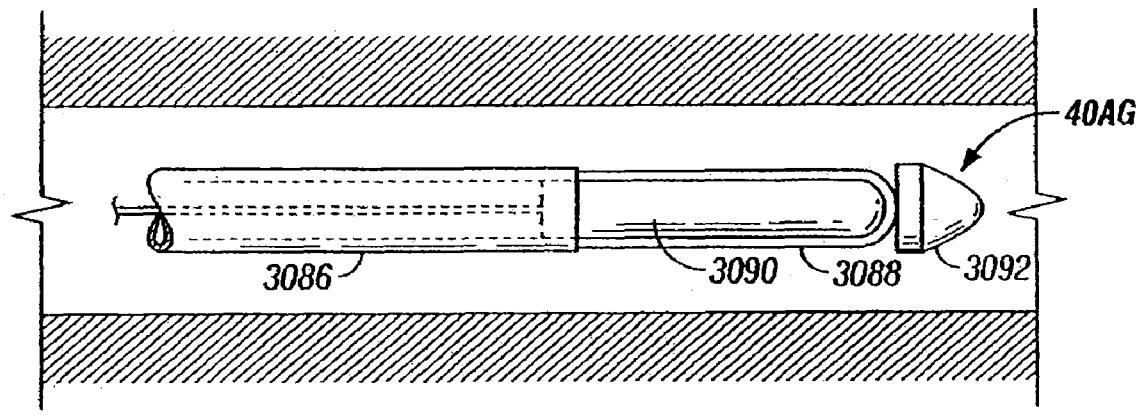
FIG. 48 is a side view of an embodiment of a treatment apparatus in an unexpanded position for use with the methods of the present invention.
Figure 49:
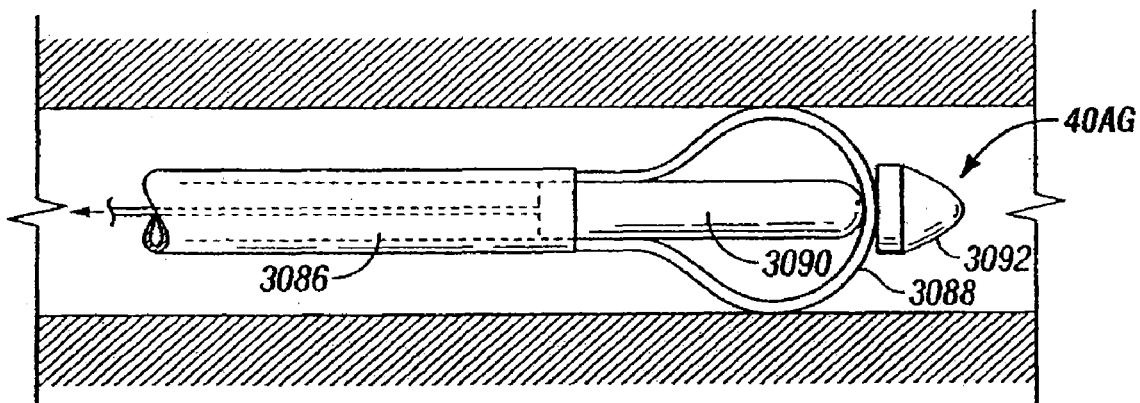
FIG. 49 is a side view of the treatment apparatus of FIG. 48 in an expanded position.

FIGS. 48 and 49 illustrate a further treatment apparatus 40AG having one or more loop shaped electrodes 3088 connected to a catheter shaft 3086. In the unexpanded position shown in FIG. 48, the loop of the electrode 3088 lies along the sides of a central core 3090. A distal end of the loop electrode 3088 is secured to the core 3090 and to an optional tip member 3092. The core 3090 is slidable in a lumen of the catheter 3086. Once the treatment apparatus 40AG has been positioned with the distal end in the airway to be treated, the electrode is expanded by pulling the core 3090 proximally with respect to the catheter 3086, as shown in FIG. 49. Alternatively, the electrode 3088 or the core 3090 may be spring biased to return to the configuration of FIG. 49 when a constraining force is removed. This constraining force may be applied by a delivery catheter or bronchoscope through which the treatment apparatus 40AG is inserted or by a releasable catch.

Figure 50:
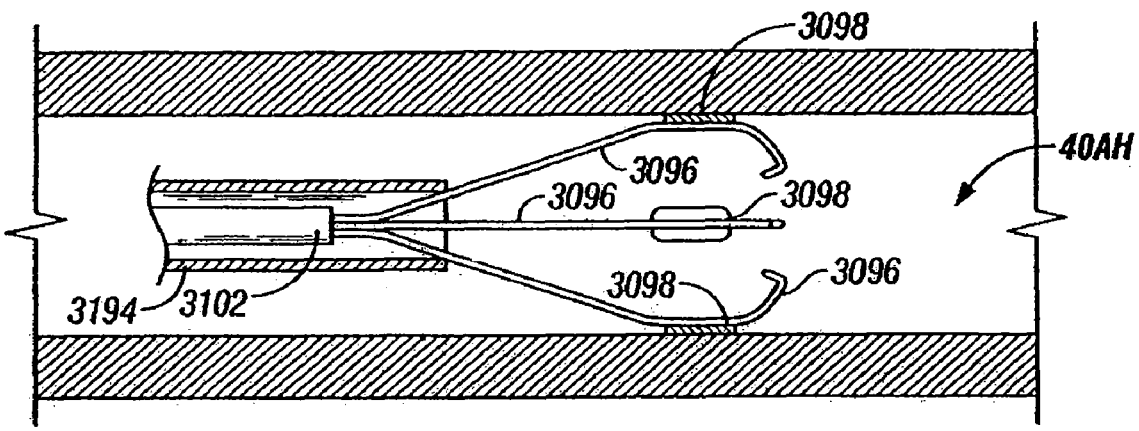
FIG. 50 is a side view of an embodiment of a treatment apparatus in an expanded position for use with the methods of the present invention.

The treatment apparatus 40AH of FIG. 50 includes a plurality electrodes 3098 positioned on leaf springs 3096 which are outwardly biased. The leaf springs 3096 are connected to a shaft 3102 which is positioned within a delivery catheter 3094. The leaf springs 3096 and electrodes 3098 are delivered through the delivery catheter 3094 to a treatment site within the airways. When the leaf springs 3096 exit the distal end of the delivery catheter 3094, the leaf springs bend outward until the electrodes 3098 come into contact with the airway walls for application of energy to the airway walls.

Figure 51:
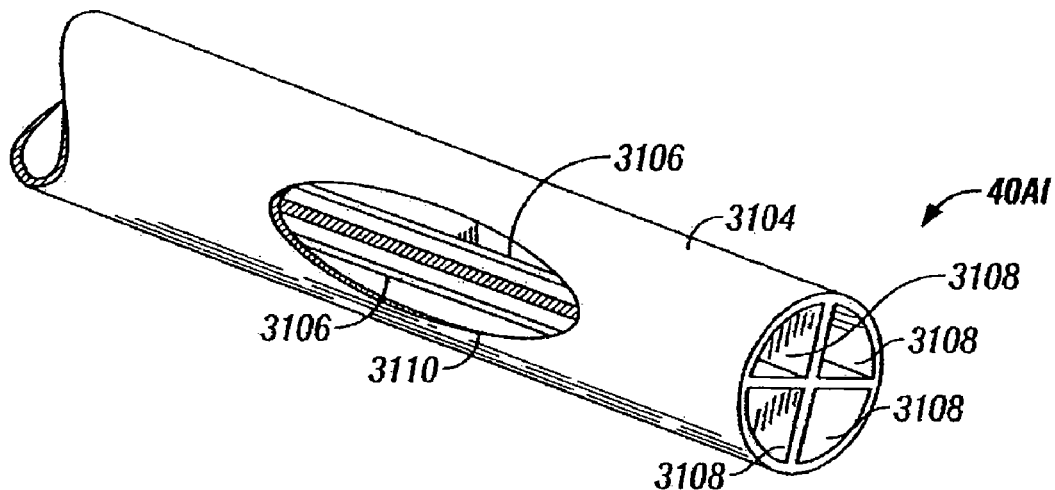
FIG. 51 is a side view of an embodiment of a treatment apparatus having a plurality of lumens containing electrodes for use with the methods of the present invention.
Figure 52:
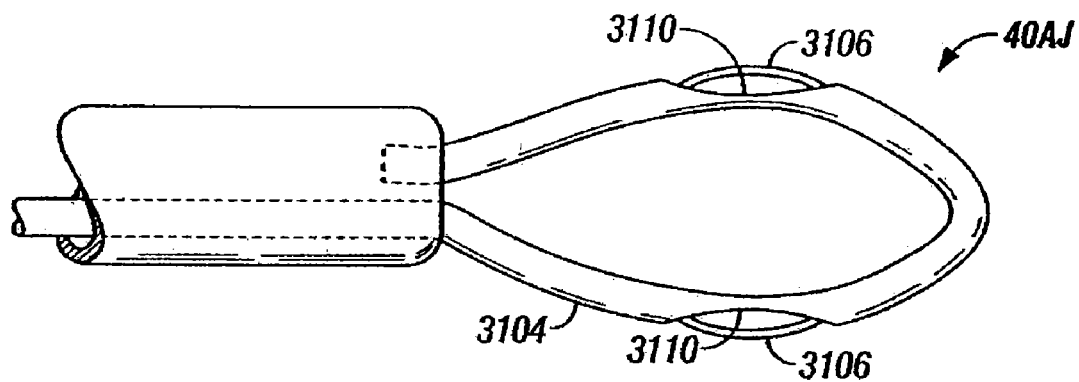
FIG. 52 is a side view of an embodiment of a treatment apparatus having electrodes exposed by cut away sections of a tube for use with the methods of the present invention.

FIGS. 51 and 52 illustrate embodiments of treatment apparatus 40AI, 40AJ in which electrodes 3106 in the form of wires are positioned in one or more lumens 3108 of a catheter 3104. Openings 3110 are formed in the side walls of the catheters 3104 to expose the electrodes 3106. As shown in FIG. 51, the treatment apparatus 40AI has multiple lumens 3108 with electrodes provided in each of the lumens. The side wall of the treatment apparatus 40AI is cut away to expose one or more of the electrodes 3106 through a side wall opening 3110. In FIG. 51, the opening 3110 exposes two electrodes positioned in adjacent lumens. The treatment apparatus 40AI may be provided with a biasing member as discussed above to bring the electrodes 3106 of the treatment apparatus into contact with the airway wall.

The treatment apparatus 40AJ of FIG. 52 includes a catheter 3104 which has been formed into a loop shape to allow the electrode 3106 to be exposed on opposite sides of the device which contact opposite sides of the airway. The resilience of the loop shape causes the electrodes to come into contact with the airway walls.

Figure 53:
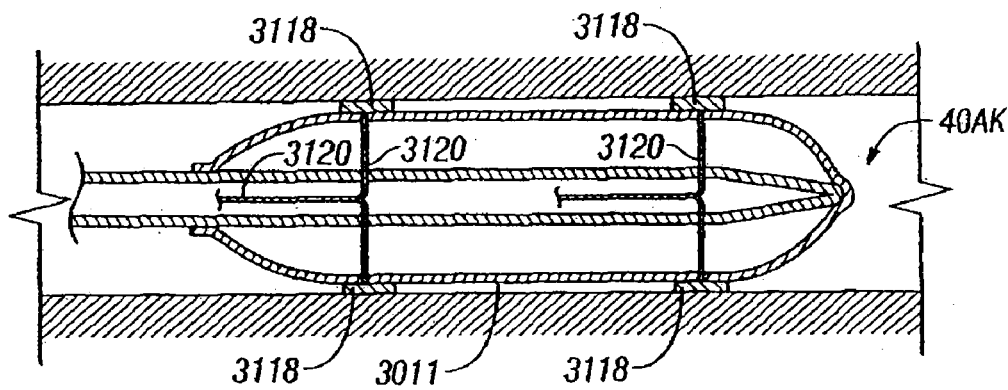
FIG. 53 is a side cross-sectional view of an embodiment of a treatment apparatus with electrodes positioned on an expandable balloon for use with the methods of the present invention.

The treatment apparatus 40AK of FIG. 53 is in the form of a balloon catheter. The treatment apparatus 40AK includes electrodes 3118 positioned on an exterior surface of an inflatable balloon 3116. The electrodes 3118 are electrically connected to the energy source 3032 by the leads 3120 extending through the balloon and through the lumen of the balloon catheter 3114. The balloon 3116 is filled with a fluid such as saline or air to bring the electrodes into contact with the airway wall 3100.

FIG. 54 illustrates an alternative embodiment of a balloon catheter treatment apparatus 40AM in which a fluid within the balloon 3126 is heated by internal electrodes 3128. The electrodes 3128 are illustrated in the shape of coils surrounding the shaft of the catheter 3124, however other electrode shapes may also be used. The electrodes 3128 may be used as resistance heaters by application of an electric current to the electrodes. Alternatively, radio frequency or microwave energy may be applied to the electrodes 3128 to heat a fluid within the balloon 3126. The heat then passes from an exterior of the balloon 3126 to the airway wall. The radio frequency or microwave energy may also be applied indirectly to the airway wall through the fluid and the balloon. In addition, hot fluid may be transmitted to the balloon 3126 from an external heating device for conductive heating of the airway tissue.

FIG. 55 illustrates a treatment apparatus 40AN for delivering heated fluid to the airway walls to heat the airway tissue. The treatment apparatus 40A includes a heating element 3132 provided within a fluid delivery catheter 3134. The fluid passes over the heating element 3132 and out of openings 3136 in the end of the catheter 3134. The openings 3136 are arranged to direct the fluid at the airway walls 3100. The heating element 3132 may be a coiled resistance heating element or any other heating element. The heating element 3132 may be positioned anywhere along the body of the catheter 3134 or may be an external heating device separate from the catheter.

The heating element 3132 may also be replaced with a friction producing heating element which heats fluid passing through the fluid delivery catheter 3134. According to one embodiment of a friction producing heating element, a friction element rotates and contacts a stationary element for purpose of heating the fluid.

FIG. 56 illustrates an alternative embodiment of a treatment apparatus 40AP including a cryoprobe tip 3150 for transferring or removing energy in the form of heat from an airway wall 3100. The cryoprobe tip 3150 is delivered to the treatment site by a cryoprobe shaft 3152. Transfer of energy from the tissue structures of the airway wall can be used in the same manner as the delivery of energy with any of the devices discussed above. The particular configuration of the cryoprobe treatment apparatus 40AP may vary as is known in the art.

Figure 57:
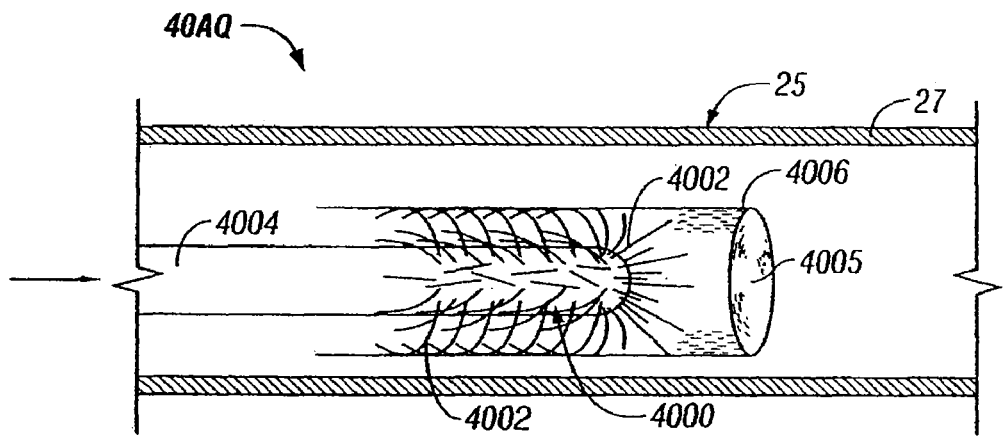
FIG. 57 is a cross-sectional view of an embodiment of a treatment apparatus that includes a brush for with the methods of the present invention.
Figure 58:
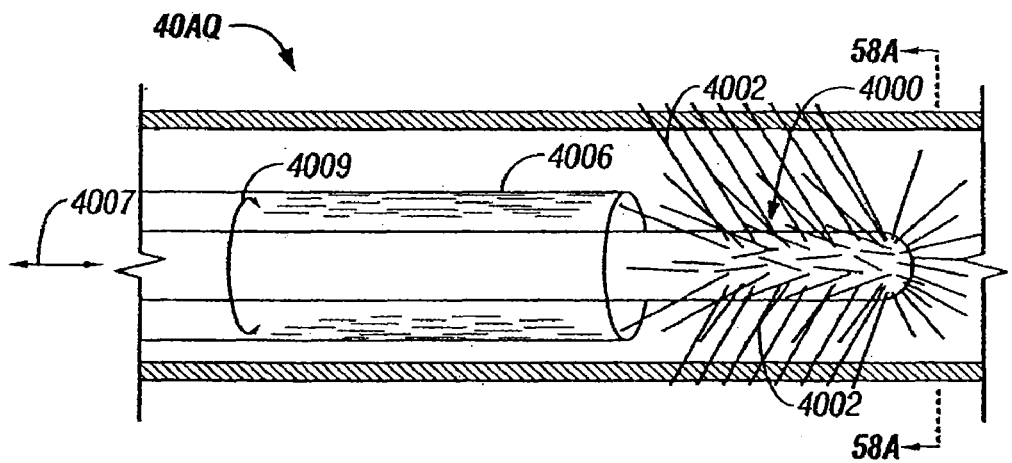
FIG. 58 is a side cross-sectional view of the device illustrated in FIG. 57 after it has treated the airway of a lung.
Figure 58A:
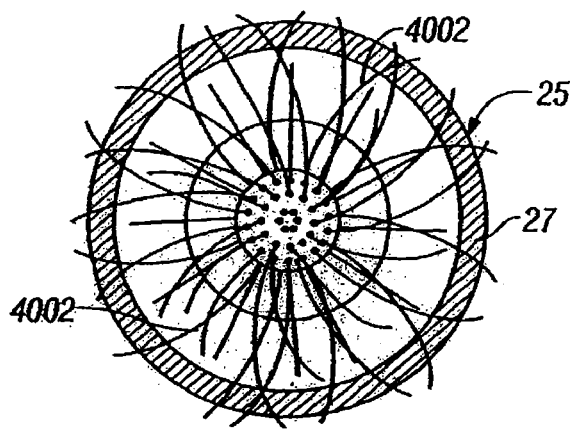
FIG. 58A is a cross-sectional view of the device illustrated in FIG. 58 taken along the line 58A-58A of FIG. 58.

FIGS. 57 and 58 illustrate another embodiment of a treatment apparatus 40AQ that may be used to treat a lung according to the present invention. The treatment apparatus 40AQ, like the previously described treatment apparatus, damages tissue of the airway 25 so as to induce fibrosis and add thickness to the airway wall. The treatment apparatus 40AQ also destroys the airway smooth muscle tone to increase gas exchange. With the treatment apparatus 40AQ, a bristled brush 4000 having a plurality of bristles 4002 is introduced into the airway 25 so as to puncture the airway wall with the bristles 4002. The bristles 4002 may be needles, pins, or other similarly shaped members. The bristles 4002 are located at the distal end of an elongated member 4004. The bristles 4002 extend radially outward from the outer surface of the distal end of the elongated member 4004, and are preferably flexible. The brush 4000 has at least one bristle 4002 that may be manipulated to damage the tissue of the airway 25.

As shown in FIG. 57, the brush 4000 is inserted through a tube-like member or cannula 4006 which has been inserted into the airway 25. Because the outer diameter of the brush 4000 (as measured about the most distal ends or tips of the bristles 4002) is greater than the interior diameter of the cannula 4006, the bristles 4002 bend against the interior surface of the cannula 4006 when the brush 4000 is located within the interior of the cannula 4006.

FIG. 58 illustrates the brush 4000 after it has been pushed through the most distal opening 4005 of the cannula 4006. Hence, as shown in FIG. 58, the brush 4000 is located at least partially outside of the cannula 4006. As also shown by FIG. 58, when the brush 4000 exits the outlet 4005 of the cannula 4006, the bristles 4002 will return radially outward to their original straight configuration, rather than the bent configuration shown in FIG. 57 where the bristles interfere with the interior surface of the cannula 4006. Hence, the bristles 4002 extend radially outward toward the wall of the airway 25 when the distal end of the brush is forced through the opening of the cannula. As shown in FIG. 58, the bristles 4002 have penetrated the wall of the airway 25 to thus cause trauma to the tissue. Once the brush 4000 of the treatment apparatus 40A extends from the outlet 4005 of the cannula 4006, the brush 4000 may be moved along the length of the duct as illustrated by the arrow 4007 in FIG. 58 so as to cause further trauma and damage to the airway 25. Additionally, as also illustrated by the arrow 4009 in FIG. 58, the brush 4000 may be rotated while in the airway 25 so as to cause damage to the airway 25. The brush 4000 may be moved along the select lengths of the airway 25 to damage predetermined portions of the airway, as desired. After the desired damage has been completed, the brush 4000 may be retracted back through the opening 4005 of the cannula 4000 such that undesired damage is not caused to other portions of the airway 25 when the brush 4000 is removed from the airway and eventually the lung.

The bristles 4002 are preferably the flexible pins illustrated in FIG. 58, and are preferably made of a metallic material such as stainless steel. The bristles preferably have a caliber that permits them to be easily bent and resiliently return to their original position after being bent. However, the bristles 4002 may take other forms. For example, the bristles 4002 may be rigid and substantially not elastic such that they are not easily bendable. That is, the bristles may be needle-like members. In this case, the length of each needle-like member must be sufficiently small so that the brush 4000 may travel through the cannula 4006, because the needle-like members will not bend in the cannula 4006 when contacting the interior surface of the cannula 4006. The brush 4000 has needle-like members which may be manipulated in the airway 25 so as to cause trauma to the airway wall.

The bristles 4002 preferably each have a sharp point or tip that will puncture the airway wall to cause damage and thus induce fibrosis and/or destroy smooth muscle tone. However, the tips of the bristles may be blunt such that the bristles will tear or rip the airway, rather than simply puncturing the airway wall. In this case, the tearing action will damage cells of tissue to induce a fibrotic response. Alternatively, the bristles 4002 may be razor-like members having a sharp longitudinal edge that slices the airway 25 to cause damage.

Figure 59:
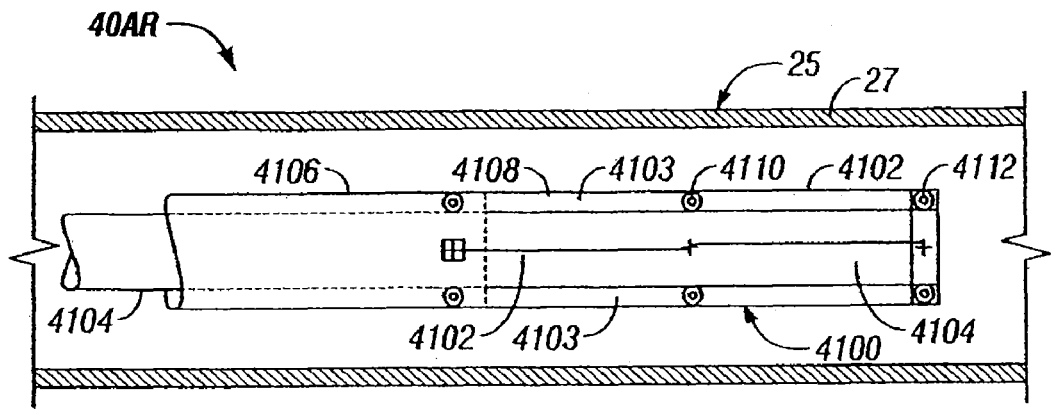
FIG. 59 is a side cross-sectional view of a treatment apparatus that includes a device for cutting or slicing the tissue of an air way of a lung in accordance with methods of the present invention.
Figure 60:
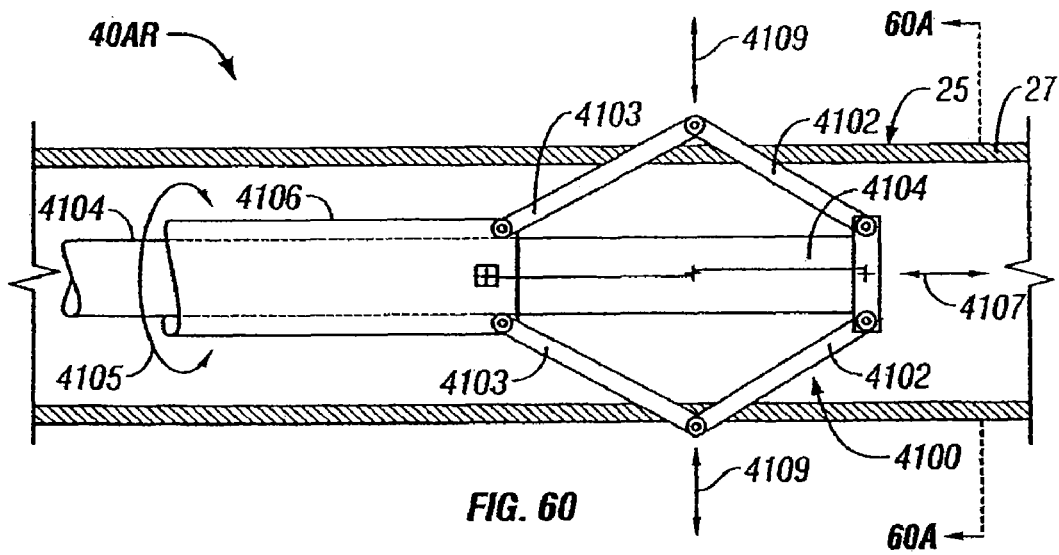
FIG. 60 illustrates a partial side cross-sectional view of the embodiment illustrated in FIG. 9, where the treatment apparatus has treated the tissue of the lung.
Figure 60A:
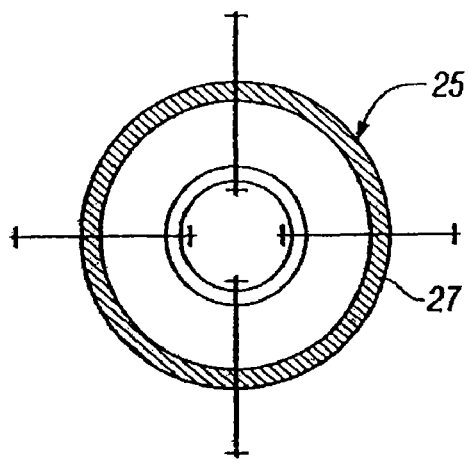
FIG. 60A is a cross-sectional view of the device illustrated in FIG. 60 taken along the line 60A-60A of FIG. 60.

FIGS. 59 and 60 illustrate another embodiment of a treatment apparatus 40AR for use with the method of the present invention. The treatment apparatus 40AR causes damage to the airway 25 by preferably cutting through the airway wall. The treatment apparatus 40AR includes a cutting device 4100 having a plurality of elongated blades 4102, 4103. As shown by the end view in FIG. 60A, the elongated blades 4102, 4103 are circumferentially spaced at four locations along the exterior surface of an inner rod 4104. However, additional blades may be included. For example, the blades may be circumferentially spaced at eight locations along the exterior surface of the inner rod 4104.

The inner rod or tube 4104 is located at least partially inside the interior of an outer tube or cannula 4106. As shown by the arrow 4107 in FIG. 60, the inner tube 4104 is movable within the interior of the outer tube 4106 along the lengthwise direction of the outer tube 4106. As shown in FIGS. 59 and 60, each of the elongated blades 4102 is pivotally connected to the inner tube 4104 by a pivot connection 4112 located at the most distal end of the inner tube 4104 so as to be rotatable about the pivot connection 4112. Each of the elongated blades 4102 located toward the distal end of the inner rod 4104 is also pivotally connected by another pivot connection 4110 to another elongated blade 4103. Hence, the pivot connection 4110 defines a point about which each of the blades 4102, 4103 rotates. The elongated blade 4103 is pivotally connected to the outer tube 4106 by a further pivot blade connection 4108 so as to be rotatable about the pivot connection 4108. Hence, the blades 4102 and 4103 are movable in the direction shown by the arrow 4109 in FIG. 60 when relative motion occurs between the inner tube 4104 and the outer tube 4106, preferably when the inner tube 4104 and/or the outer tube 4106 are moved in the direction of the arrow 4107. For example, when the inner tube 4104 and the outer tube 4106 are moved from the positions illustrated in FIG. 59 to the positions illustrated in FIG. 60, each of the elongated blades 4102 and 4103 will pivot about the pivot connections 4108, 4110, 4112 such that the elongated blades 4102, 4103 move toward the wall of the airway 25 and cut through tissue of the airway to induce fibrosis. The more the most distal end of the inner tube 4104 having the pivot connection 4112 and the most distal end of the outer tube 4106 having the pivot connection 4108 are moved toward each other, the more the blades 4102, 4103 will rotate about the pivot connections 4112, 4110, 4108. In this manner, the elongated blades 4102, 4103 may be caused to cut through the tissue of the airway 25 so as to cause trauma. Preferably, the elongated blades 4102, 4103 will damage tissue 27 such that scar tissue develops to thicken the wall of the airway and thus strengthen the airway. As shown in FIG. 60, the elongated blades 4102, 4103 have cut or sliced through the tissue of the airway.

The elongated blades 4102, 4103 may be repeatedly collapsed and expanded as shown in FIGS. 59 and 60 so as to cause multiple cuts to the airway tissue, as desired. Additionally, the elongated blades 4102, 4103 may be moved in the longitudinal direction of the airway wall while the blades are in the expanded position shown in FIG. 60 so as to further slice the airway tissue. Likewise, the cutting apparatus 4100 may be rotated in the airway 25 as shown by the arrow 4105 in FIG. 60 so as to cut and/or tear the tissue of the airway 25.

The elongated blades 4102, 4103 are preferably thin razor-like elongated members of stainless steel that easily slice through the airway tissue. However, the elongated blades 4102, 4103, may take other configurations. For example, the elongated blades 4102, 4103 may be rods having a serrated surface or surfaces that cut or tear through the airway tissue. Additionally, the elongated blades 4102, 4103 may each include a plurality of pins that function to penetrate or puncture the airway tissue to destroy smooth muscle tone and/or induce fibrosis to strengthen the airway wall and thus improve gas exchange efficiency.

Figure 61:
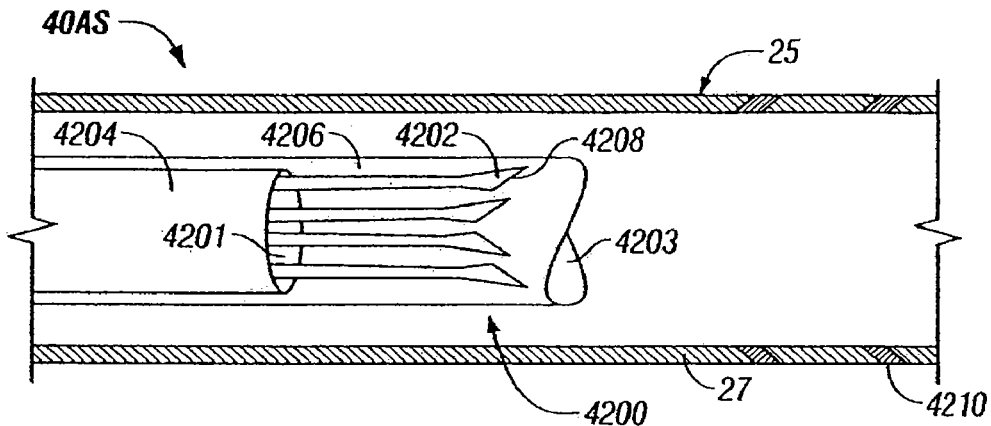
FIG. 61 is a side cross-sectional view of another embodiment of a treatment apparatus, where the treatment apparatus includes a plurality of members for slicing or cutting the air way of a lung in accordance with the methods of the present invention.
Figure 62:
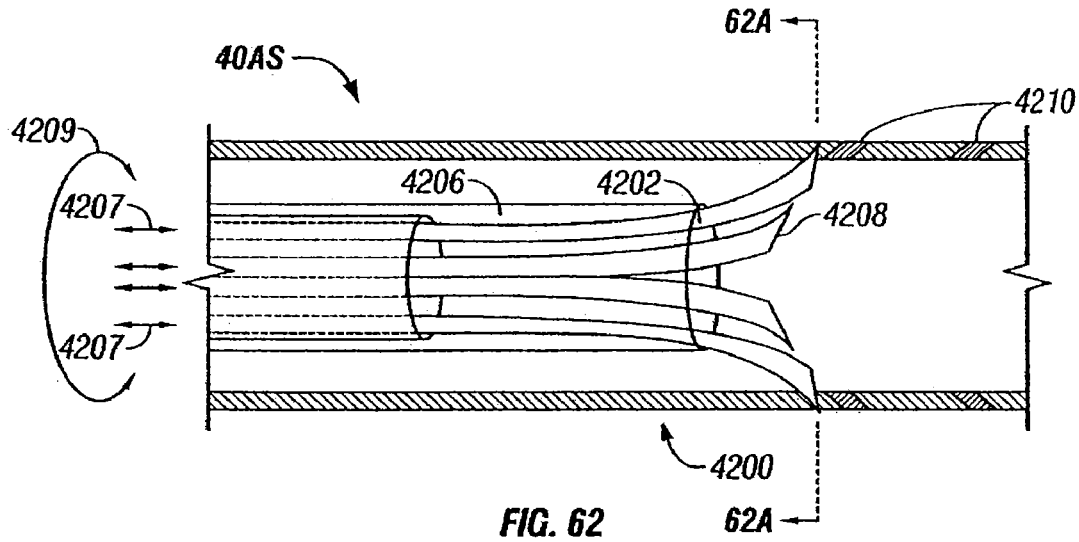
FIG. 62 illustrates the treatment apparatus of FIG. 61 in a deployed position.
Figure 62A:
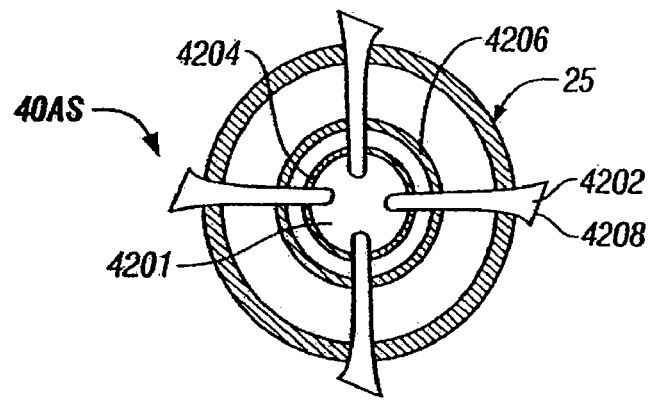
FIG. 62A is a cross-sectional view of the device illustrated in FIG. 62 taken along the line 62A-62A of FIG. 62.

FIGS. 61-62 illustrate a further embodiment of a treatment apparatus 40AS for use with the method of the present invention. The treatment apparatus 40AS includes a slicing device 4200 that slices through the airway tissue to destroy smooth muscle tone and/or damage lung tissue and induce fibrosis to strengthen the airway wall. The slicing device 4200 includes a plurality of elongated slicing members 4202 that each include a razor edge 4208 located at the most distal end of the slicing members. The slicing members 4202 are preferably elongated metallic members that protrude from the an outlet 4201 of an inner tube 4204. The slicing members 4202 are movable in the inner tube 4202 along the lengthwise direction of the inner tube 4204 as shown by the arrows 4207 illustrated in FIG. 62. The inner tube 4204, similar to the previously described embodiments, is located within an outer tube or cannula 4206. The slicing members 4202 may be forced out of an opening 4203 of the outer tube 4206 at the most distal end of the outer tube such that they project outwardly from the end of the outer tube 4206. FIG. 61 illustrates the slicing members 4202 located completely inside of the outer tube 4206, while FIG. 62 illustrates the slicing members 4202 after they have been moved out of the opening 4203 of the outer tube 4206. The slicing members 4202 may be manually forced through the opening 4203 or automatically caused to move through the opening 4203 by a controller (not illustrated).

As illustrated in FIGS. 61 and 62, when the slicing members 4202 are moved out of the opening 4203, they bend or curve away from the longitudinal axis of the outer tube 4206 such that the members slice through the airway tissue of the airway 25. Hence, the slicing members 4202 are preferably biased to bend away from the longitudinal axis of the outer tube 4206. That is, each of the slicing members acts like a spring and moves toward the airway wall after exiting the outlet 4203.

The slicing members 4202 may be attached to the inner tube 4204 such that the slicing members 4202 move with the inner tube 4204 when the inner tube is moved relative to the outer tube 4206. Additionally, the slicing members 402 may not be attached to the inner tube 4204 such that they are movable relative to the inner tube 4204, as well as the outer tube 4206. As shown by the arrow 4209 in FIG. 61, the slicing members 4202 can be rotated relative to the airway 25 during the treatment process so as to slice, cut, or tear through the airway wall to cause further trauma.

Although the embodiment shown in FIGS. 61-62 includes only four slicing members 4202, other numbers of slicing members are contemplated. For example, the treatment apparatus 4AS can slice the airway tissue with 8, 16, 32, 56, or other numbers of slicing members 4202 that are movable relative the airway 25 so as to cause damage to the airway tissue of the lung.

The slicing members 4202 can be moved to repetitively slice through the tissue of the airway 25 so as to define a plurality of sliced areas 4210. In general, the greater the number of sliced areas 4210 made with the treatment apparatus 40AS, the greater the damage of smooth muscle tone and the greater the fibrotic response, which will thicken the airway wall and strengthen the airway wall to thus increase gas exchange.

The slicing members 4202 are preferably thin and elongated members having a razor edge 4208. However, the slicing members 4202 can be other configurations. For example, each of the slicing members 4202 may include a pin point rather than a razor edge. Additionally, each of the slicing members 4202 may include serrations or a razor edge along the elongated edges or sides of the slicing members 4202, which may extend the entire length of the slicing member or only along predetermined portions of the length.

FIGS. 63-65 illustrate further embodiments of treatment apparatus 40AT for use with the present invention. As shown in FIG. 63, the treatment apparatus 40AT includes a balloon 4312 having a plurality of pins 4308 attached to the outer surface of the balloon. The balloon 4312 is similar to the previously described balloons and may be fabricated from like materials. The balloon 4312 is partially located within an inner tube 4304, as well as a containment sheath 4309. The balloon 4312 extends from the outlet end of the inner tube 4304. As shown in FIG. 64, the inner tube 4304 is connected to a fluid supply 4314, which can supply a pressurized gas or fluid to the interior of the tube 4304 and hence the interior of the balloon 4312 to cause the balloon to expand as shown in FIG. 64.

The sheath 4309 that surrounds or encases the balloon 4312 includes a plurality of openings 4302 that extend through the cylindrical wall of the sheath 4309. Hence, the openings 4302 communicate the exterior of the sheath 4309 with the interior of the sheath. The balloon 4312 is attached to the sheath 4309 at the most distal end 4310 of the sheath. The openings 4302 in the sheath 4309 are located at locations on the exterior surface of the sheath 4309 such that when the balloon 4312 is expanded the pins 4308 will travel through the openings 4302 and protrude from the exterior surface of the sheath 4309. That is, the openings 4302 are spaced along the length and the circumference of the sheath 4309 the same distance that the pins 4308 are spaced along the length and circumference of the balloon 4312. Hence, when the balloon 4312 is expanded upon application of pressure by the fluid supply 4314, the pins will move radially toward the airway and extend through the openings 4302. When the balloon 4312 has been fully expanded as shown in FIG. 64, the pins 4308 will protrude through the openings 4302 and will puncture the tissue of the airway 25 so as to destroy smooth muscle tone and/or induce fibrosis and strengthen the airway.

The sheath 4309 is preferably formed of a rigid material, such as hard plastic, so that the location of the openings 4302 relative to the location of the pins 4308 on the balloon 4312 remains relatively constant during the treatment process. The sheath 4309 is preferably attached to the outer tube 4306 such that the sheath 4309 will move when the outer tube 4306 is moved: Hence, after the balloon has been expanded to cause pins 4308 to extend through the openings 4302 and puncture the airway tissue, the sheath 4309, the outer tube 4306, the balloon, and the pins 4308 may be moved in the longitudinal direction of the airway 25 so as to further tear or slice through the airway tissue. Likewise, as shown by the arrow 4307 shown in FIG. 64, the sheath 4309 may be rotated so as to rotate the pins 4308 to cause further damage to the tissue of the airway.

As shown in FIGS. 63 and 64, the pins 4308 are located on diametrically opposite sides of the balloon 4312, as are the openings 4302 of the sheath 4309. However, the balloon 4312 may include further rows and columns of pins 4308 and the sheath may include further rows and columns of openings 4302, as illustrated by the embodiment of the treatment apparatus 40AT illustrated in FIG. 65. As shown in FIG. 65, the balloon 4312 includes eight rows of pins 4308 equally spaced along the length and circumference of the balloon 4312. Hence, the sheath 4309 also includes correspondingly located openings 4302 that the pins 4308 may protrude through when the balloon 4312 is expanded. Other numbers of pins 4308 and openings 4302 are also contemplated.

The balloons of the embodiments illustrated in FIGS. 63-65 can be repeatedly expanded and contracted so as to cause multiple punctures to the airway tissue to destroy the airway smooth muscle tone and induce fibrosis and hence stiffen the wall of the airway. Additionally, the pins 4308 can be other configurations. For example, a plurality of razors, knives, or blunt members can be attached to the balloon such that the airway tissue is sliced, cut, or torn when the balloon is expanded.

Figure 66:
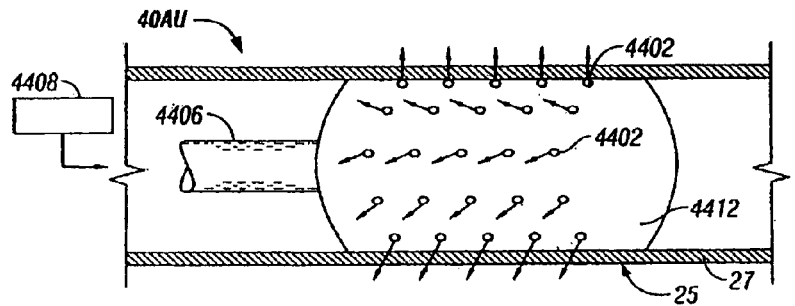
FIGS. 66-70 illustrate embodiments of treatment apparatus that deliver a fluid to the airway to treat the lungs in accordance with the methods of the present invention.

FIG. 66 illustrates another embodiment of a treatment apparatus 40AU that may be used according to the present invention. The treatment apparatus 40AU includes a balloon 4412, which is illustrated in its expanded state in FIG. 66. The balloon 4412 includes a plurality of openings 4402 that communicate the exterior of the balloon with the interior of the balloon. The openings 4402 are a plurality of small holes that extend through the wall of the balloon 4412. The balloon 4412 is attached to the end of a tube or cannula 4406. The interior of the balloon 4412 may be filled with a liquid or gas from the fluid supply 4408. Hence, the fluid supply 4408 is in communication with the interior of the balloon 4412 through the tube 4406. The balloon may be expanded as shown in FIG. 66 by pressurizing the interior of the balloon 4412 with a liquid or gas from the supply 4408. The liquid or gas supplied from the supply 4408 will exit the balloon 4412 through the openings 4402 located in the balloon. The expanded balloon 4412 contacts with the airway wall. Hence, when the fluid exits the balloon 4412 through the openings 4402, it will contact the tissue of the airway 25. The fluid that exits the balloon 4412 may be a heated liquid or gas, similar to the above-described embodiments that destroy cells of the airway tissue by the application of heat. The fluid is preferably a biocompatible liquid, such as liquid saline or air. Additionally, the fluid delivered by the supply 4408 may be cold liquid or gas that destroys the airway tissue by removing heat from the airway tissue when it passes through the openings 4402 of the balloon 4412. In a preferred embodiment of the treatment apparatus 40AU, the liquid or gas supplied by the supply 4408 is cooled to a temperature that destroys airway smooth muscle tone and/or damage airway tissue to induce a fibrotic response to strengthen the airway 25. The liquid or gas delivered by the treatment apparatus 40AU can also destroy tissue cells by chemically reacting with the tissue. For example, the treatment apparatus 40AU can deliver an acid to the airway tissue to cause trauma to the tissue.

Although the expanded balloon 4412 illustrated in FIG. 66 contacts the wall of the airway 25, the balloon 4412 can be smaller than the airway 25 such that it does not contact the airway wall when expanded.

Figure 67:
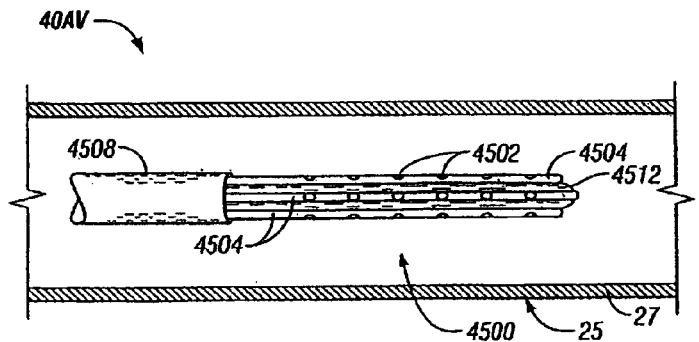
Figure 68:
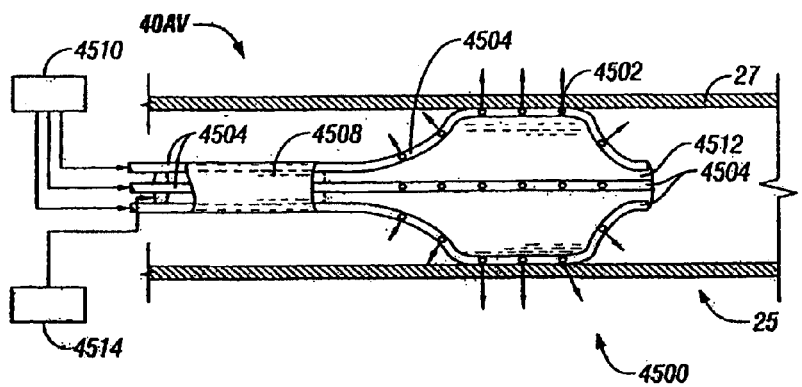

FIGS. 67 and 68 illustrate another embodiment of a treatment apparatus 40A that can be used to perform the present method of the invention. The treatment apparatus 40AV, like the apparatus 40AU illustrated in FIG. 66, includes a balloon 4512. The balloon 4512 is illustrated in its collapsed condition in FIG. 67, and is illustrated in its expanded condition in FIG. 68. As shown in FIGS. 67 and 68, the balloon 4512 includes a plurality of tubes 4504 attached to the exterior surface of the balloon 4512. The interior of the balloon 4512 is not in communication with the interior of the tubes 4504. The plurality of tubes 4504 are preferably circumferentially spaced about the exterior cylindrical surface of the balloon 4512. Each of the tubes 4504 extends along the longitudinal length of the balloon 4512 and through the interior of a tube or cannula 4508. Like the embodiment illustrated in FIG. 66, the balloon 4512 may be inflated by a fluid supply 4514 which supplies a gas or liquid to the interior of the balloon 4512 to cause it to expand to the position illustrated in FIG. 68. However, unlike the embodiment illustrated in FIG. 66, the expansion of the balloon 4512 does not cause a liquid or gas to be delivered to the wall of the airway 25. Rather, a separate fluid supply 4510 delivers a liquid or gas to the interior of each of the tubes 4504.

The liquid or gas delivered by the fluid supply 4510 travels through the interior of the elongated tubes 4504 and out of a plurality of openings 4502 spaced along the length of each of the tubes 4504. The openings 4502 are equidistantly spaced along the length of the tube 4504. Hence, after the balloon is expanded by pressure from the supply 4514, the supply 4510 may supply a liquid or gas to the interior of the tubes 4504 and out of the openings 4502 such that the liquid or gas from the supply 4510 contacts the airway tissue. As with the embodiment described above in reference to FIG. 66, the liquid or gas supplied from the supply 4510 will damage the airway tissue. The fluid or gas delivered through the holes 4502 damages tissue 27 to induce fibrosis and thicken the wall of the airway 25 so as to strengthen the airway wall and increase the gas exchange efficiency of the lung. The fluid or gas can also destroy the smooth muscle tone to increase gas exchange.

Figure 69:
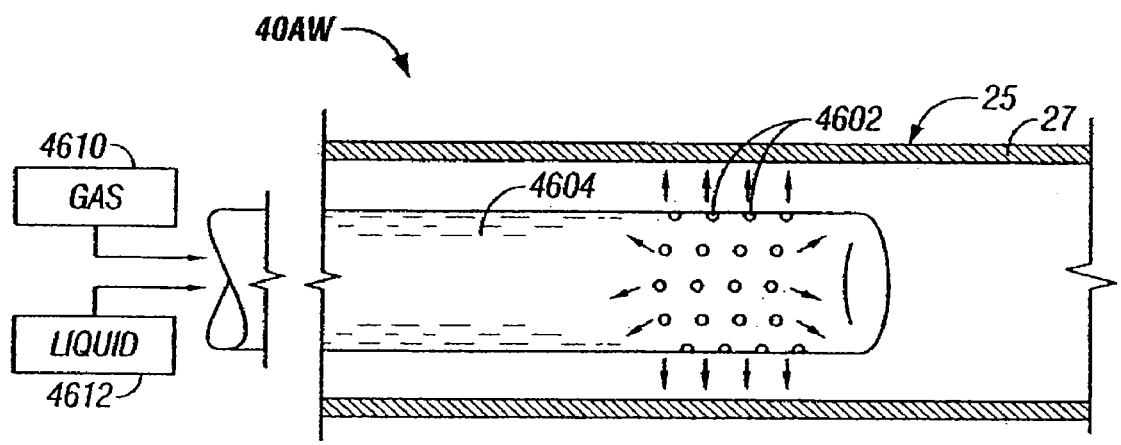

FIG. 69 illustrates an additional embodiment of a treatment apparatus 40AW for use with the methods of the present invention. The treatment apparatus 40AW includes a tube or cannula 4604 having a plurality of holes 4602 located at a most distal end of the tube 4604. The plurality of holes 4602 form a plurality of columns and rows about the circumference of the tube 4604, as illustrated in FIG. 69. The holes 4602 deliver a fluid, such as that described above in reference to FIGS. 66-68 to the tissue of the airway 25 to damage cells and induce fibrosis. As shown in FIG. 69, a gas supply 4610 and/or a liquid supply 4612 may deliver a fluid to the interior of the tube 4604, through the holes 4602, and to the tissue of the airway 25. In this manner, a gas and/or a fluid will destroy smooth muscle tone and/or damage tissue to induce fibrosis and increase the gas exchange efficiency of the lung.

FIG. 70 illustrates a further embodiment of a treatment apparatus 40AX for use with the methods according to the present invention. The treatment apparatus 40AX, like the embodiments illustrated in FIGS. 66-69, delivers a liquid or a gas to the airway 25 so as to damage of the airway tissue. In the embodiment illustrated in FIG. 70, an inner tube 4702 is located within an outer tube 4704. The inner tube 4702 may be connected to a gas supply or a liquid supply 4710. Likewise, the outer tube 4704 may be connected to a gas supply or liquid supply 4712. The fluid delivered to the interior of the inner tube 4702 from the supply 4710 exits the outlet 4708 at the distal end of the inner tube 4702. The fluid delivered from the supply 4712 exits the outlet 4706 at the most distal end of the outer tube 4704. Because there are two separate tubes 4702, 4704, and two separate supplies 4710, 4712, two separate liquids, two separate gases, or a combination of liquids and gases may be delivered to the airway tissue to cause trauma to destroy smooth muscle tone and/or cause fibrosis and strengthen the airway 25. For example, two liquids or gases may be combined at the outlets 4706, 4708 to cause a chemical reaction that damages the cells of the airway tissue to induce fibrosis.

Figure 71:
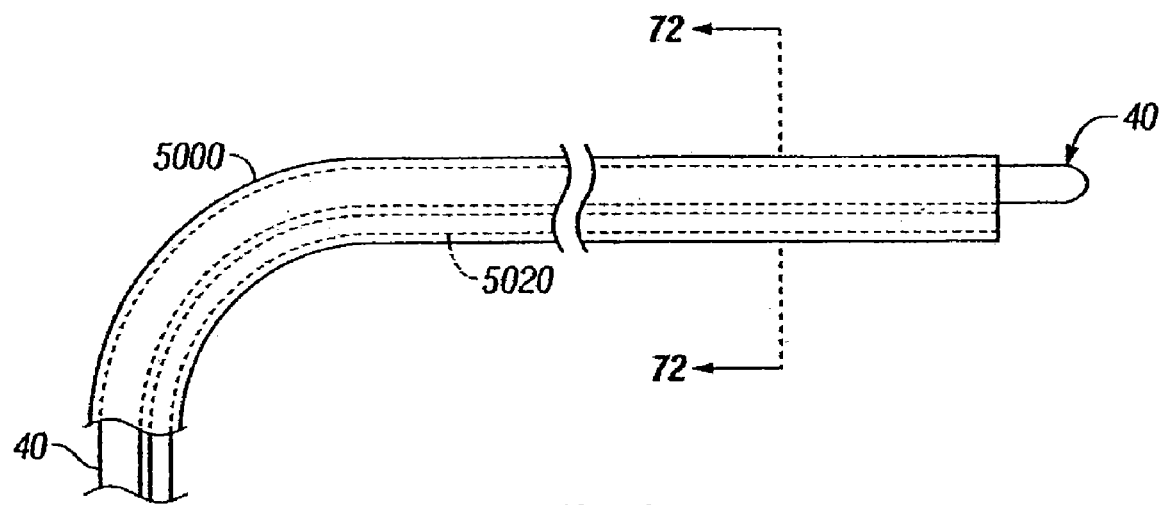
FIG. 71 is a side view of a bronchoscope that may be used to deploy the above-illustrated treatment apparatus when practicing the present invention.
Figure 72:
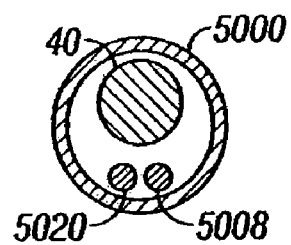
FIG. 72 is a cross-sectional view of the device illustrated in FIG. 71 taken along the line 72-72 of FIG. 71.

FIGS. 71 and 72 illustrate a bronchoscope, such as described earlier, that may be used with each of the above-described treatment apparatus 40. The bronchoscope 5000 has a treatment apparatus 40 slidably positioned within a lumen of the bronchoscope. The bronchoscope also includes an image-transmitting fiber 5008 and illuminating fiber 5020. Any conventional bronchoscope with an appropriately sized and directed working lumen may be employed. The image transmitting fiber collects light from the distal end of the treating apparatus and directs the light to a viewing apparatus (not shown) for displaying an image of the air passage. The bronchoscope may have a panning system which enables the tip to be moved in different directions. In treating a particular site, excessive fluid is first removed from the obstructed air passage by conventional means such as with suction. Thereafter, the bronchoscope as illustrated in FIGS. 71 and 72 is advanced from the person's nasal or oral cavity, and through the trachea, main stem bronchus, and into an air passage. The treatment apparatus 40 is advanced forward from the bronchoscope such that the treatment apparatus may be used to destroy airway smooth muscle tone and/or cause damage to airway tissue to induce fibrosis and strengthen an airway of the lung. This procedure is applied to a sufficient number of obstructed air passages until the physician determines that the treatment is finished. As is apparent, the procedure can be completed in one treatment or multiple treatments. The bronchoscope and the treatment apparatus 40 are then removed from the patient.

The principles, preferred embodiments and modes of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims be embraced thereby.

The invention claimed is:

1. A method of treating an airway in an asthmatic lung of a patient, comprising:
   inserting an elongated shaft into the airway, wherein the elongated shaft has a distal end, and wherein an energy transfer device is at the distal end of the elongated shaft;
   delivering microwave energy to tissue structures of an airway wall at a treatment site via the energy transfer device, whereby the microwave energy causes the airway to undergo a transformation effective to reduce asthma symptoms.

2. The method of claim 1, further comprising:
   (a) terminating delivery of microwave energy to the treatment site;
   (b) moving the energy transfer device proximally to a new treatment site along the airway;
   (c) delivering microwave energy to tissue structures of the airway wall at the new treatment site; and
   repeating acts a-c along the airway.

* * * * *

UNITED STATES PATENT AND TRADEMARK OFFICE
CERTIFICATE OF CORRECTION

PATENT NO.         : 7,770,584 B2
APPLICATION NO.    : 12/328596
DATED              : August 10, 2010
INVENTOR(S)        : Christopher J. Danek et al.

It is certified that error appears in the above-identified patent and that said Letters Patent is hereby corrected as shown below:

On the Title page, in Item (63), in column 1, under "Related U.S. Application Data" line 8, after "11/117,905," insert -- filed on Apr. 29, 2005, --.

On the Title page, in Item (63), in column 1, under "Related U.S. Application Data" line 20-21, after "09/999,851," insert -- filed on Oct. 25, 2001, --.

On page 4, in column 2, in Item (56), under "Other Publications" line 6, delete "156s-159s," and insert -- 516s-519s, --, therefor.

On page 4, in column 2, in Item (56), under "Other Publications" line 13, delete "Lobectomym" and insert -- Lobectomy --, therefor.

On page 4, in column 2, in Item (56), under "Other Publications" line 25, delete "perisstent" and insert -- persistent --, therefor.

In column 6, line 39, delete "perisstent" and insert -- persistent --, therefor.

In column 9, line 30, delete "alviolar" and insert -- alveolar --, therefor.

In column 9, line 33, delete "alviolar" and insert -- alveolar --, therefor.

In column 12, line 16, delete "seconds to" and insert -- second to --, therefor.

In column 14, line 40, delete "be" and insert -- by -- therefor.

In column 33, line 10, delete "the an" and insert -- an --, therefor.

Signed and Sealed this
Twenty-fifth Day of January, 2011

David J. Kappos
*Director of the United States Patent and Trademark Office*